United States Patent
Peterson et al.

(10) Patent No.: US 8,329,639 B2
(45) Date of Patent: *Dec. 11, 2012

(54) MUC1 BASED GLYCOLIPOPEPTIDE VACCINE WITH ADJUVANT

(75) Inventors: Scott Peterson, Woodinville, WA (US); Linda Pestano, Tucson, AZ (US); Jeffrey Millard, Seattle, WA (US); Diana F. Hausman, Seattle, WA (US); Sandy Koppenol, Lake Forest Park, WA (US); Robert Kirkman, Yarrow Point, WA (US)

(73) Assignee: Oncothyreon Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/553,061

(22) Filed: Jul. 19, 2012

(65) Prior Publication Data

US 2012/0282329 A1    Nov. 8, 2012

Related U.S. Application Data

(63) Continuation of application No. 13/403,679, filed on Feb. 23, 2012.

(60) Provisional application No. 61/470,449, filed on Mar. 31, 2011, provisional application No. 61/446,332, filed on Feb. 24, 2011.

(51) Int. Cl.
*A61K 38/00* (2006.01)
*A61P 31/00* (2006.01)
*C07K 14/00* (2006.01)

(52) U.S. Cl. ...... 514/1.1; 514/19.1; 514/19.2; 514/19.3; 514/19.4; 514/19.5; 530/300; 530/324

(58) Field of Classification Search .......... None
See application file for complete search history.

(56) References Cited

U.S. PATENT DOCUMENTS

| | | |
|---|---|---|
| 3,930,024 A | 12/1975 | Creger |
| 4,235,871 A | 11/1980 | Papahadjopoulos et al. |
| 4,464,383 A | 8/1984 | Yamamoto |
| 4,501,728 A | 2/1985 | Geho et al. |
| 4,719,202 A | 1/1988 | Boeckel et al. |
| 4,837,028 A | 6/1989 | Allen |
| 4,868,155 A | 9/1989 | Durette et al. |
| 4,912,094 A | 3/1990 | Myers et al. |
| 5,019,369 A | 5/1991 | Presant et al. |
| 5,019,383 A | 5/1991 | Hopp |
| 5,041,427 A | 8/1991 | Takayama et al. |
| 5,191,072 A | 3/1993 | Hasegawa et al. |
| 5,580,563 A | 12/1996 | Tam |
| 5,744,144 A | 4/1998 | Finn et al. |
| 5,837,249 A | 11/1998 | Heber-Katz et al. |
| 5,840,839 A | 11/1998 | Wang et al. |
| 5,871,746 A | 2/1999 | Boutillon et al. |
| 5,910,306 A | 6/1999 | Alving et al. |
| 5,993,823 A | 11/1999 | Boutillon et al. |
| 6,013,779 A | 1/2000 | Wong et al. |
| 6,015,564 A | 1/2000 | Boutillon et al. |
| 6,090,406 A | 7/2000 | Popescu et al. |
| 6,113,918 A | 9/2000 | Johnson et al. |
| 6,136,790 A | 10/2000 | Toepper et al. |
| 6,316,421 B1 | 11/2001 | Nantz et al. |
| 6,344,203 B1 | 2/2002 | Sandrin et al. |
| 6,600,012 B1 | 7/2003 | Agrawal et al. |
| 6,683,052 B1 | 1/2004 | Thiam et al. |
| 6,699,846 B2 | 3/2004 | Elliott et al. |
| 6,764,840 B2 | 7/2004 | Johnson et al. |
| 7,820,627 B2 | 10/2010 | Jiang |
| 8,097,593 B1 | 1/2012 | Jiang |
| 2002/0051813 A1 | 5/2002 | Boni et al. |
| 2002/0132771 A1 | 9/2002 | Madiyalakan |
| 2003/0157160 A1 | 8/2003 | Budzynski |
| 2003/0235610 A1 | 12/2003 | McLean et al. |
| 2005/0112184 A1 | 5/2005 | John et al. |
| 2006/0069238 A1 | 3/2006 | Koganty |
| 2007/0014844 A1 | 1/2007 | Longenecker |
| 2008/0131495 A1 | 6/2008 | Longenecker |
| 2012/0034294 A1 | 2/2012 | DuPuit et al. |

FOREIGN PATENT DOCUMENTS

| | | |
|---|---|---|
| DE | 906808 | 3/1954 |
| EP | 614215 | 7/1947 |
| EP | 0093851 | 11/1983 |
| EP | 0203676 | 12/1986 |
| EP | 0230893 | 8/1987 |
| EP | 0491628 | 6/1992 |
| EP | 0122151 | 2/1999 |
| EP | 0945461 | 9/1999 |
| EP | 1065212 | 1/2001 |
| EP | 1182210 | 2/2002 |
| FR | 2776926 A1 | 10/1999 |
| JP | 58-10592 | 1/1983 |
| JP | 63-139186 | 6/1988 |
| JP | 2001-510440 | 7/2001 |
| JP | 2008-285459 | 11/2008 |
| WO | WO-86-05687 | 10/1986 |
| WO | WO-93-21211 | 10/1993 |
| WO | WO-95-01966 | 1/1995 |
| WO | WO-95-27505 | 10/1995 |
| WO | WO-96-40236 | 12/1996 |

(Continued)

OTHER PUBLICATIONS

PCT/US2012/026385 International Search Report mailed Jun. 6, 2012.

Albrecht et al. "Development of anti-MUC1 di-scFvs for molecular targeting of epithelial cancers, such as breast and prostate cancers." *Q J Nucl Med Mol Imaging*, 2007, 51:304-314.

Butts et al. "Updated survival analysis in patients with stage IIIB or IV non-small-cell lung cancer receiving BLP25 liposome vaccine (L-BLP25); phase IIB randomized, multicenter, open-label trial." *Journal of Cancer Research and Clinical Oncology*, Jul. 2011, 137(9): 1337-1342.

(Continued)

*Primary Examiner* — Peter J Reddig

(74) *Attorney, Agent, or Firm* — Wilson, Sonsini, Goodrich & Rosati

(57) ABSTRACT

Provided herein are liposomal glycolipopeptidic vaccine formulations comprising an adjuvant and an immunogen for immunotherapy and/or treatment of cancer.

8 Claims, 9 Drawing Sheets

FOREIGN PATENT DOCUMENTS

| | | |
|---|---|---|
| WO | WO-97-34921 A1 | 9/1997 |
| WO | WO-97-38010 | 10/1997 |
| WO | WO-98-50527 | 11/1998 |
| WO | WO-01-12217 | 2/2001 |
| WO | WO-01-18035 | 3/2001 |
| WO | WO-01-36433 | 5/2001 |
| WO | WO-01-70265 | 9/2001 |
| WO | WO-01-79243 | 10/2001 |
| WO | WO-02-43699 | 6/2002 |
| WO | WO-02-076485 | 10/2002 |
| WO | WO-03-066649 | 8/2003 |
| WO | WO-03-089574 A2 | 10/2003 |
| WO | WO-03-089574 A3 | 10/2003 |
| WO | WO-03-094850 | 11/2003 |
| WO | WO-2005-112546 | 12/2005 |
| WO | WO-2010-078045 | 7/2010 |

OTHER PUBLICATIONS

Kutuzova et al., "Diphosphoryl Lipid A from *Rhodobacter sphaeroides* Blocks the Binding and Internalization of Lipopolysaccharide in RAW 264.7 Cells," J Imm. 167:482-489 (2001).
Machy et al., "Liposomes in Cell Biology and Pharmacology", 4 pages, John Libbey.
U.S. Appl. No. 13/403,679, filed Feb. 23, 2012, Peterson et al.
"About the Albert B. Sabin Vaccine Institute." *Cancer Immunol Immunotherapy* 52(Suppl. 1):S1-S38 (2003).
Aguilera et al., "Novel Disaccharide Inhibitors of Human Glioma Cell Division," *J. Med Chem*, 1998, 41:4599-4606.
Alving. "Lipopolysaccharide, Lipid A, and Liposomes Containing Lipid A as Immunologic Adjuvants." *Immunobiol.*, 1993, 187(3-5):430-446.
Armspach et al., "Boron-rich metallodendrimers-mix and-match assembly of multifunctional metallosupramolecules," *Chem Comm* 1996, 15:1823-1824.
Apostolopoulos et al., "Induction of HLA-A2-Restricted CTLs to the Mucin 1 Human Breast Cancer Antigen," *J Immunol* 1997, 159:5211-5218.
Bakker-Woudenberg et al. "Liposomes as Carriers of Antimicrobial Agents or Immunomodulatory Agents in the Treatment of Infections." *Eur. J. Clin. Microbiol. Infect. Dis.*, 1993, vol. 12, Supplement 1, pp. 61-67, European Society of Clinical Microbiology & Infectious Diseases.
Bartels et al. "Adoptive Cellular Immunotherapy of Cancer in Mice Using Allogenic T-Cells." *An Oncology Journal for Surgeons*, 1996, 13(1):67-73, Lippincott-Raven Publishers.
Beilstein Abstract, Registry #4885466 (underlying reference 1992).
Beilstein Abstract, Registry #1776862 (underlying reference 1952).
Beilstein Abstract, Registry #1777272 (underlying reference 1953).
Beilstein Abstract, Registry #2299756 (underlying reference 1971).
Beilstein Abstract, Registry #2450963 (underlying reference 1979).
Beilstein Abstract, Registry #2478491 (underlying reference 1979).
Beilstein Abstract, Registry #4386563 (underlying reference 1981).
Beilstein Abstract, Registry #4438100 (underlying reference 1981).
Beilstein Abstract, Registry #4866378 (underlying reference 1992).
Beilstein Abstract, Registry #3310799 (underlying reference 1937).
Beilstein Abstract, Registry #3433270 (underlying reference 1937).
Beilstein Abstract, Registry #7349279 (underlying reference 1988).
Beilstein Abstract, Registry #7349664 (underlying reference 1988).
Beilstein Abstract, Registry #299061 (underlying reference 1950).
Beilstein Abstract, Registry #6129710 (underlying reference 1966).
Beilstein Abstract, Registry #6129784 (underlying reference 1966).
Beilstein Abstract, Registry #1817997,entry date Jun. 29, 1989.
Beilstein Abstract, Registry #1894672,entry date Jun. 29, 1989.
Beilstein Abstract, Registry #2271917,entry date Jun. 29, 1989.
Beilstein Abstract, Registry #1842361,entry date Jun. 29, 1989.
Beilstein Abstract, Registry #2289689,entry date Jun. 29, 1989.
Beilstein Abstract, Registry #2301356,entry date Jun. 29, 1989.
Beilstein Abstract, Registry #4360897,entry date Dec. 2, 1991.
Beilstein Abstract, Registry #7682492,entry date Jul. 31, 1997.
Beilstein Abstract, Registry #7682309,entiy date Jul. 31, 1997.
Beilstein Abstract, Registry #7684107,entry date Jul. 31, 1997.
Beilstein Abstract, Registry #7683736,entry date Jul. 31, 1997.
Beilsten Abstract XP-002337686 for Beilstein registry #8730629, entry date Apr. 26, 2001.
Benmohamed et al. "High Immunogenicity in Chimpanzees of Peptides and Lipopeptides Derived from Four New Plasmodium Falciparum Pre-Erythrocytic Molecules." *Vaccine*, 2000, 18:2843-2855.
Benmohamed et al. "Lipopeptide Immunization Without Adjuvant Induces Potent and Long-Lasting B, T Helper, and Cytotoxic T Lymphocyte Responses Against a Malaria Liver Stage Antigent in Mice and Chimpanzees." *Eur. J. Immunol.*, 1997, 27:1242-1253, VCH Verlagsgesellschaft mbH, D-69451, Weinheim.
Brossart et al., "Identification of HLA-A2-Restricted T-Cell Epitopes Derived From the MUC1 Tumor Antigen for Broadly Applicable Vaccine Therapies," *Blood* 1999, 93(12):4309-4317.
Burchell et al., "Effect of Modification of Carbohydrate Side Chains on the Reactivity of Antibodies with Core-Protein Epitopes of the MUC1 Gene Product," *Epith Cell Biol* 1993, 2:155-162.
Butts et al., "Randomized Phase IIB Trial of BLP25 Liposome Vaccine in Stage IIIB and IV Non-Small Cell Lung Cancer," *J Clin Onc* 2005, 23(27):6674-6681.
Butts et al., "A multicenter phase IIB randomized study of liposomal MUC1 vaccine for immunotherapy of non-small cell lung cancer (NSCLC): L-BLP25 non-small cell cancer study group," *Ann Onc* 2004, 15(Suppl.3):1112 (Abstract).
Carmon et al., "Novel Breast-Tumor-Associated MUC1-Derived Peptides: Characterization in $D^{b-}$/-X β2 Microglobulin (β2m) Null Mice Transgenic for a Chimeric HLA-A2. 1/$D^b$ Microglobulin Single Chain," Int J Cancer 85:391-397 (2000).
Charon et al., "Chemical synthesis and Immunological Activities of Glycolipids Structurally Related to Lipid A," Biochem 24:2736-2742 (1985).
Cheng et al., "Molecular Design of Liquid-Crystalline Block Molecules: Semifluorinated pentaerythritol Tetrabenzoates Exhibiting Lamellar, Columnar, and Cubic Mesophases," Angew Chem Int Ed 39(3):592-595 (2000).
Christ et al., "E5531, a Pure Endotoxin Antagonist of High Potency," Science 268:80-83 (1995).
Denton et al., "Sequential Order of T and B Cell Epitope Affects Immunogenicity But Not Antibody Recognition of the B Cell Epitope," Peptide Res 7(5):258-264 (1994).
Diez-Barra et al., Chemical Abstract. "Solvent-free phase transfer catalysis. Improvements on serine O-alkylation," Database accession No. 127:220955(1997) (English Abstract).
Donnerstag et al., "A Structurally and Biogenetically Interesting Moenomycin Antibiotic," Tetrahedron 51(7):1931-1940 (1995).
Dunn et al., "Versatile Methods for the Synthesis of Differentially Functionalized Pentaerythritol Amine Derivatives," J Org Chem 55:6368-6373 (1990).
El-Abadla et al., "Moenomycin A: The Role of the Methyl Group in the Moenuronamide Unit and a General Discussion of Structure-Activity Relationships," Tetrahedron 55:699-722 (1999).
Engelmann et al., "Identification and Topology of Variant Sequences within Individual Repeat Domains of the Human Epithelial Tumor Mucin MUC1," J Biol Chem 276(30):27764-27769 (2001).
Farcy et al., "A Pentaerythritol-Based Molecular Scaffold for Solid-Phase Combinatorial Chemistry," Org Ltrs 3(26):4299-4301 (2001).
Fehlhaber et al., "Moenomycin A: A Structural Revision and New Structure-Activity Relations," Tetrahedron 46(5):1557-1568 (1990).
Ferse et al., "Acceptor Site Recognition of Transglycosylase Inhibitors A B-D-glucopyranosyl-(1-2)-alpha-D-glucopyranuronamide-derived Moenomycin Analogue," Tetrahedron 55:3749-3766 (1999).
Flinn et al., "Oral absorption studies of lipidic conjugates of thyrotropin releasing hormone (TRH)-1 and luteinizing hormone-releasing hormone (LHRH)," Intl J Pharmaceutics 137(1):33-39 (1996).
Fujishima et al., "New synthetic immunomodulators combining a 4-O-phosphono-D-glucos-amine derivative related to bacterial lipid A with 1-deoxy-N-acetylmuramoyl dipeptide analogs," Carbo Res 167:317-324 (1987).
Fung et al., "Specific Immunosuppressive Activity of Epiglycanin A Mucin-Like Glyeoprotein Secreted by a Murine Mammary Adenocarcinoma TA3-HA." *Cancer Research* 1991, 51(4):1170-1176.

Gahery-Segard et al. "Muitiepitopic B- and T-Cell Responses Induced in Humans by a HumanImmunodeficiency Virus Type 1 Lipopeptide Vaccine." *Journal of Virology*, Feb. 2000, 74(4): 1694-1703, American Society for Microbiology.

Gendler et al., "A Highly Immunogenic Region of a Human Polymorphic Epithelial Mucin Expressed by Carcinoma is Made Up of Tandem Repeats," J Biol Chem 263(26):12820-12823 (1988).

Goldman et al., "Differential Antibacterial Activity of Moenmycin Analogues on Gram-Positive Bacteria," Bioorg. Med Chem Ltrs 10:2251-2254 (2000).

Grohmann et al. "Immunogenicity of tumor peptides: importance of peptide length and stability of peptide/MHC class II complex." *Cancer Immunol Immunother*, 1999, 48:195-203.

Gupta et al. "Adjuvants—A Balance Between Toxicity and Adjuvanticity." *Vaccine*, 1993, vol. 11, Issue 3, pp. 293-306, Butterworth-Heinemann, Ltd.

Guan et al. "Liposomal Formulations of Synthetic MUC1 Peptides: Effects of Encapsulation versus Surface Display of Peptides on Immune Responses." *Bioconjugate Chem.*, 1998, 9: 451-458.

Hanessian et al., "Synthesis of clustered D-GalNAc (Tn) and D-GALB(1-3)GalNAc (T) antigenic motifs using a pentaerythritol scaffold," Can J Chem 74:1738-1747 (1996).

Hanisch et al., "MUC1: the polymorphic appearance of a human mucin," Glycobiol 10(5):439-449 (2000).

Hanski et al., "Altered Glycosylation of the MUC-1 Protein Core Contributes to the Colon Carcinoma-associated Increase of Mucin-bound Sialyl-Lewis Expression," Cancer Research 53:4082-4088 (1993).

Hebler-Klintz et al., "The First Moenoycin Antibiotic Without the Methyl-Branched Uronic Acid Consituent," Tetrahedron 49(35):7667-7678 (1993).

Heukamp et al., "Identification of Three Non-VNTR MUC1-Derived HLA-A*0201—Restricted T-Cell Epitopes that Induce Protective Anti-Tumor Immunity in HLA-A2/$K^b$ Transgenic Mice," Int J Cancer 91:385-392 (2001).

Hiltbold et al., "Naturally Processed Class II Epitope from the Tumor Antigen MUC1 Primes Human CD4+ T Cells," Cancer Res 58:5066-5070 (1998).

Hohgardt et al., "Synthesis of Two Structural Analogues of the Smallest Antibiotically Active Degradation Product of Moenomycin A," Tetrahedron 44(18):5771-5790 (1988).

Imoto et al., "Chemical Structure of *Escherichia coli* Lipid A," Tetrahedron Ltrs 26(7):907-908 (1985).

Imoto et al., "Total Synthesis of *Escherichia coli* Lipid A," Tetrahedron Ltrs. 26(12):1545-1548 (1985).

Jahn et al. "Microfluidic Directed Formation of Liposomes of Controlled Size." *Langmuir*, Apr. 2007, 23(11):6289-6293.

Jiang et al., "Novel lipid A mimetics derived from pentaerythritol: synthesis and their potent agonist activity," Tetrahedron 58:8833-8842 (2002).

Jiang et al., "Synthetic Vaccines: The Role of Adjuvants in Immune Targeting," Curr Med Chem 10:1423-1439 (2003).

Karanikas et al., "Antibody and T cell Responses of Patients with Adenocarcinoma Immunized with Mannan-MUC1 Fusion Protein," J Clin Invest 100:2783-2792 (1997).

Karsten et al., Cancer Res 5:82541-2549 (1998).

Keil et al., "Towards the Development of Antitumor Vaccines: A Synthetic Conjugate of a Tumor-Associated MUC1 Glycopeptide Antigen and a Tetanus Toxin Epitope," Ange Chem Int Ed 40(2):366-369 (2001).

Kim et al, "Liposomes as Carriers of Cancer Chemotherapy," *Drugs*, Oct. 1993, 46(4): 618-638, Adis International Limited.

Kirschenbaum et al., "MUC1 expression in prostate carcinoma: correlation with clinical grade and stage," Molecular Urology 3:163-167 (1999).

Kiso et al., "Synthesis of 2-Deoxy-4-O-Phosphono-3-O-Tetradecanoyl-2-[(3R)-And (3S)-3-Tetradecanoyloxytetradecanamido]-D]Glucose: A Diastereoisomeric Pair of 4-O-Phosphono-D-Glucosamine Derivatives (GLA-27) Related to Bacterial Lipid A," Carbo Res 148:221-234 (1986).

Kotani et al., "Immunobiological Activities of Synthetic Lipid A Analogs with Low Endotoxicity," Infection and Immunity 54(3):673-682 (1986).

Kotani et al., "Low Endotoxic Activities of Synthetic *Salmonella*-Type Lipid A with an Additional Acyloxyacyl Group on the 2-Amino Group of B(1-6)Glucosamine Disaccharide 1,4'-Bisphosphate," Infection and Immunity 52(3):872-884 (1986).

Kreuter, Jörg. "Colloidal Drug Delivery Systems." *Drugs and Pharmaceutical Sciences*, 1994, vol. 66, pp. 4 pages, Marcel Dekker, Inc.

Kudryashov et al., "Toward optimized carbohydrate-based anticancer vaccines: Epitope clustering, carrier structure, and adjuvant all influence antibody responses to Lewis[y] conjugates in mice," PNAS 98(6):3264-3269 (2001).

Kutuzova et al., "Diphosphoryl Lipid A from *Rhodobacter sphaeroides*Blocks the Binding and Internalization of Lipopolysaccharide in RAW 264.7 Cells," J Imm. 167:482-489 (2001).

Kuzdzal et al., "Dendrimer Electrokinetic Capillary Chromatography: Unimolecular Micellar Behaviour of Carboxylic Acid Terminated Cascade Macromolecules," J Chem Soc Chem Commun. 18:2139-2140 (1994).

Lien et al., "A Novel Synthetic Acyclic Lipid A-Like Agonist Activates Cells via the Lipopolysaccharide/Toll-like Receptor 4 Signaling Pathway," J Biol Chem 276(3):1873-1880 (2001).

Lindhorst et al., "Cluster Mannosides as Inhibitors of Type 1 Fimbriae-Mediated Adhesion of *Escherichia coli*: Pentaerythritol Derivatives as Scaffolds," Eur J Org Chem 2000(11):2027-2034 (2000).

Lopes et al., "Immunoexpression of MUC1 in prostate adenocarcinoma," Virchows Arch 435:330 (1999).

Machy et al., "Liposomes in Cell Biology and Pharmacology", 4 pages, John Libbey, 1987.

MacLean et al., "Prognostic Significance of Preimmunotherapy Serum CA27.29 (MUC-1) Mucin Level After Active Specific Immunotherapy of Metastatic Adenocarcinoma Patients," J Immunotherapy 20(1):70-78 (1997).

Martin et al., "Enzymatic Synthesis of a Modified Phospholipid and Its Evaluation as a Substrate for *B. cereus* Phospholipase C," Bioorg. Med Chem Ltrs. 8:593-596 (1998).

Martinon et al., "Immunization of Mice with Lipopeptides Bypasses the Prerequisite for Adjuvant," J Immunol 149(10):3416-3422 (1992).

Mehta et al. "L-BLP25 Vaccine plus Letrozole Induces a TH1 Immune Response and has Additive Antitumor Activity in MUC-1 Expressing Mammary Tumors in Mice." *Clin Cancer Res.*, Mar. 20, 2012, 5 pages.

Metten et al., "The First Enzymatic Degradation Products of the Antibiotic Moenomycin A," Tetrahedron 48(39):8401-8418 (1992).

Meylan et al., "Atom/Fragment Contribution Method for Estimating Octanol-Water Partition Coefficients," J Pharm Sci 84(10:83-92 (1995).

Miller et al., "Vaccination of Rhesus Monkeys with Synthetic Peptide in a Fusogenicproteoliposome Elicits Simian Immunodeficiency Virus-Specific CD8+ Cytotoxic T Lymphocytes," J Exp Med 176:1739-1744 (1992).

Moller et al., "NMR-based determination of the binding epitope and conformationatl analysis of MUC-1 glycopeptides and peptides bound to the breast cancer-selective monoclonal antibody SM3," Eur J Biochem 269:1444-1455 (2002).

Moller et al., "Moenomycin A-Structure-Activity Relations Synthesis of the D-Galacturonamide Analogue of the Smallest Antibiotically Active Degradation Product of MoenomycinA," Tetrahedron 49(8):1635-1648 (1993).

Mondelli et al. "Significance of the Immune Response to a Major, Conformational B-Cell Epitope on the Hepatitis C Virus NS3 Region Defined by a Human Monoclonal Antibody." *Journal of Virology*, Aug. 1994, pp. 4829-4836.

Morse, Michael A. "Technology Evaluation: BLP-25, Biomira Inc." *Current Opinion in Molecular Therapeutics*, 2001, 3(1):102-105.

Mortara et al., "Selection of Virus Variants and Emergence of Virus Escape Mutants after Immunization with an Epitope Vaccine," J Virol 72(2):1403-1410 (1998).

Mountain, "Revisions in the International System for Staging Lung Cancer," Chest 111:1710-1717 (1997).

Neurath et al.. "Antibodies to Hepatitis B Surface Antigen (HbsAg) Elicited by Immunization with a Synthetic Peptide Covalently Linked to Liposomes." *Journal of General Virology*, 1984, 65:1009-1014.

Ng et al., "Prognostic significance of increased immunodetectable MUC-1 in prostate cancer," Proceeding of the American Association for Cancer Research 38:542 (1997.

North and Butts, "Vaccination with BLP25 liposome vaccine to treat non-small cell lung and prostate cancers," Expert Rev Vaccines 4(3):249-257 (2005).

North et al., "Randomized Phase IIB trial of BLP25 Liposome Vaccine in Stage IIIB and IV Non-Small Cell Lung Cancer," J Clin Onc 23(27):6674-6681 (2005).

Ostro et al. "Use of Liposomes as Injectable-Drug Delivery Systems." *American Journal of Hospital Pharmacy*, Aug. 1989, 46(8):1576-1587.

Palmer et al., "Phase I Study of the BLP25 (MUC1 Peptide) Liposomal Vaccine for Active Specific Immunotherapy in Stage IIIB/IV Non-Small-Cell Lung Cancer," Clin Lunc Cancer 3(1):49-57 (2001).

Palmer et al., Annals of Oncology 11 (Suppl4):42 (2000) (Abstract).

Pantuck et al. "Phase I Trial of Antigen-Specific Gene Therapy Using a Recombinant Vaccinia Virus Encoding MUC-1 and IL-2 in MUC-1-Positive Patients with Advanced Prostate Cancer." J. Immunother, 2004, 27(3):240-253.

Papadopoulos et al., "Tumor Angiogenesis is Associated with MUC1 Over expression and Loss of Prostate-specific Antigen Expression in Prostate Cancer," Clin Cancer Res 7:1533-1538 (2001).

Petrakou et al., "Epitope Mapping of Anti-MUC1 Mucin Protein Core Monoclonal Antibodies," Tumor Biol 19(Suppl.1):21-29 (1998).

Pihl et al., "Mucinous Colorectal Carcinoma: Immunopathology and Prognosis," Pathology 12:439-447 (1980).

Price et al., "Summary Report on the ISOBM TD-4 Workshop: Analysis of 56 Monoclonal Antibodies against the MUC1 Mucin," Tumor Biol 19(Suppl.1):1-20, (1998).

Ranganathan et al., "Self-Assembling, Cystine-Derived, Fused Nanotubes Based on Spirane Architecture: Design, Synthesis, and Crystal Structure of Cystinospiranes," J Am Chem Soc 123 (24):5619-5624 (2001).

Range et al., "A Chemoenzymatic Approach towards Moenomycin Structural Analogues," Tetrahedron 53(5):1695-1706 (1997).

Reddish et al., "Pre-Immunotherapy Serum CA27, 29 (MUC-1) Mucin Level and CD69+ Lmphocytes Correlate with Effects of Theratope Sialyl-TN-KLH Cancer Vaccine in Active Specific Immunotherapy." *Cancer Immunology and Immunotherapy* 1996, 42(5):303-309.

Reichel et al., "Synthetic carbohydrates-based vaccines: synthesis of an L-glycero-D-manno-heptose antigen-T-epitope-lipopeptide conjugate," Chem Comm Need Volume:2087-2088 (1997).

Ribi et al., "Preparation and Antitumor Activity of Nontoxic Lipid A," Cancer Immunol Immunother 12:91-96 (1982).

Riedel et al., "Synthesis and Transglycosylase-Inhibiting Properties of a Disaccharide Analogue of Moenomycin A Lacking Substitution at C-4 of Unit F," Tetrahedron 55:1921-1936 (1999).

Rietschel et al., "Bacterial Endotoxic Lipopolysaccharides," Mol Biochem Cell Biol 1:3-41 (1992).

Rietschel et al., "Bacterial Endotoxin: Chemical Constitution, Biological Recognition, Host Response, and Immunological Detoxification," Curr Top Microbiol Immunol 216:39-81 (1996).

Rietschel et al., "Concepts of the Chemical Structure of Lipd A," Rev. Inf. Dis. 6(4):432-438 (1984).

Rietschel et al., "Structure and conformation of the lipid A component of lipopolysaccharides," Handbook of Endotoxin 1, Chapter 5, pp. 187-220 (1984).

Ritzeler et al., "Synthesis of a Trisaccharide Analogue of Moenomycin A12 Implications of New Moenmoycin Structure-Activity Relationships," Tetrahedron 53(5):1675-1694 (1997).

Samuel, "PLGA Nanosphere Delivery of Peptides and Lipopeptides to Dentritic Cells." *Cancer Immunol Immunotherapy*, 2002, 52(Suppl):S15.

Sangha et al., "L-BLP25: A peptide vaccine strategy in non-small cell lung cancer," Clin Cancer Res 13(15):4652s-4654s (2007).

Sato et al., "A Novel Synthetic Lipid A Analog with Low Endotoxicity, DT-5461, Prevents Lethal Endotoxemia," Infection and Immunity 63(8):2859-2866 (1995).

Sauzet et al., "Long-lasting anti-viral cytotoxic T lymphocytes induced in vivo with chimeric-multirestricted lipopeptides," Vaccine 13(14):1339-1345 (1995).

Scher et al., "Post-therapy Serum Prostate-Specific Antigen Level and Survival in Patients with Androgen-Independent Prostate Cancer," J National Cancer Institute 91(3):244-251 (1999).

Scherkenbeck et al., "Structures of Some Moenomycin Antibiotics-Inhibitors of Peptidoglycan Biosynthesis," Tetrahedron 49(15):3091-3100 (1993).

Scherphof et al. "Uptake and Intracellular Processing of Targeted and Nontargeted Liposomes by Rat Kupffer Cells In Vivo and In Vitro." *Annals New York Academy of Sciences*, 1985, pp. 369-385.

Schmidt et al., "Synthesis of Glycolipid Clusters with Pentaerythritol Cores and Different Ethyleneoxy-Spaced Mannose Residues as Terminal Carbohydrates," Eur J Org Chem 2002(4):669-674 (2002).

Scholfield et al., "MUC1 mucin in urological malignancy," BJU Intl 91:560-566 (2002).

Schromm et al., "Biological activities of lipopolysaccharides are determined by the shape of their lipid A portion," Eur J Biochem 267:2008-2013 (2000).

Schut et al. "MUC1 expression, splice variant and short form transcription (MUC1/Z, MUC1/Y) in prostate cell lines and tissue," *BJU International*, 2003, 91(3):278-283.

Seth et al. "Evaluation of a Lipopeptide Immunogen as a Therapeutic in HIV Type 1-Seropositive Individuals." *Aids Research and Human Retroviruses*, 2000, 16(4):337-343, Mary Ann Liebert, Inc.

Seydel et al., "Intrinsic conformation of lipid A is responsible for agonistic and antagonistic activity," Eur J Biochem 267:3032-3039 (2000).

Soares et al., "Three Different Vaccines Based on the 140-Amino Acid MUC1 Peptide with Seven Tandemly Repeated Tumor-Specific Epitopes Elicit Distinct Immune Effector Mechanisms in Wild-Type Versus MUC1-Transgenic Mice with Different Potential for Tumor Rejection," J Immunol 166:6555-6563 (2001).

Springer, "T and Tn, General Carcinoma Autoantigens," Science 224:1198-1206 (1984).

Strain et al., "Location of Polar Substituents and Fatty Acyl Chains on Lipid A Precursors from a 3-Deoxy-D-manno-octulosonic Acid-deficient Mutant of *Salmonella typhimurium*," J Biol Chem 260(30):16089-16098 (1985).

Stryer, Conformation and Dynamics, $2^{nd}$ ed, W.H. Freemand and Co., New York, p. 74, chapter 4, part 1, 1981.

Sugiura et al. "Prognostic Value of Pleural Effusion in Patients with Non-Small Cell Lung Cancer." *Clinical Cancer Research*, 1997, vol. 3:47-50.

Takada et al., "Structure-Function Relationships of Lipid A," Mol. Biochem. Cell Biol 1(5):107-134 (1992).

Takada et al., "Structural Requirements of Lipid A for Endotoxicity and Other Biological Activities," CRC Microbiol 16(6):477-523 (1989).

Takayama et al., Separation and Characterization of Toxic and Nontoxic Forms of Lipid A, Rev Infectious Diseases 6(4):439-443 (1984).

Taylor-Papadimitriou et al., "Molecular aspects of mucin," Cancer Rev 11-12:11-24 (1988).

Timmerman, Luke. "Oncothyreon Marches on With 'Son of Stimuvax' Cancer Vaccine." www.Xconomy.com [online], Apr. 10, 2012 [retrieved on Apr. 12, 2012]. Retrieved from the Internet: http://www.xconomy.com/seattle/2012/04/10/oncothyreon-marches-on-with-son-of-stimuvax-cancer-vaccine/.

Toepter et al., "Synthesis of Novel Mimetics of the Sialyl Lewis X Determinant," Tetrahedron Ltrs. 36(50):9161-9164 (1995).

Toyokuni et al., "Synthetic Vaccines: Synthesis of a Dimeric Tn Antigen-Lipopeptide Conjugate that Elicits Immune Responses against Tn-Expressing Glycoproteins," J Am Chem Soc 116:395-396 (1994).

Tsunoda et al. "Lipopeptide Particles as the Immunologically Active Component of CTL Inducing Vaccines." *Vaccine*, 1999, 17:675-685.

Ulrich et al., Abstract Only, "Monophosphoryl lipid A as an adjuvant. Past experiences and new directions," Pharm Biotechnol 6:495-524 (1995).

Vitiello et al. "Development of a Lipopeptide-based Therapeutic Vaccine to Treat Chronic HBV Infection." *The Journal of Clinical Investigation*, Jan. 1995, pp. 341-349, The American Society for Clinical Investigation, Inc.

Von Mensdorff-Pouilly et al., Abstract Only, "Human MUC1 mucin: a multifaceted glycoprotein," Int J Biol Markers 15(4):343-356 (2000).

Von Mensdorff-Pouilly et al., "Reactivity of Natural and Induced Human Antibodies to MUC1 Mucin with MUC1 Peptides and N-Acetylgalactosamine (GalNAc) Peptides," Int J Cancer 86:702-712 (2000).

Von Mensdorff-Pouilly et al., "Survival in Early Breast Cancer Patients is Favorably Influenced by a Natural Humoral Immune Response to Polymorphic Epithelial Mucin," J Clin Oncol 18(3):574-583 (2000).

Wassaf et al. "Lipsomes as Carriers for Vaccines." *Immunomethods*, 1994, 4:217-222.

Welzel et al., "Moenomycin A: Further Structural Studies and Preparation of Simple Derivatives," Tetrahedron 39(9):1583-1591 (1983).

Welzel et al., "Moenomycin A: Minimum Structural Requirements for Biological Activity," Tetrahedron 43(3):585-598 (1987).

Welzel et al., "Preliminary Communication. Stepwise degradation of oenomycin A," Carbo Res 126:C1-C5 (1984).

Werner et al., "Immunostimulating agents: what next? A review of their present and potential medical applications," Eur J Biochem 242:1-19 (1996).

Wilkinson et al, "Synthesis and in Vitro T-Cell Immunogenicity of Conjugates with Dual Specificity: Attachment of Epitope Peptides of 16 and 38 kDa Proteins from *Mycobacterium tuberculosis* to Branched Polypeptide." *Bioconjugate Chem.*, 1998, 9:539-547.

Worl et al., "Synthesis of New Liquid Phase Carriers for Use in Large Scale Oligonucleotide Synthesis in Solution," Tetrahedron 55:2941-2956 (1999).

Zeng et al., "Synthesis of a New Template with a Built-in Adjuvant and its Use in Constructing Peptide Vaccine Candidates Through Polyoxime Chemistry.." *J Peptide Science*, 1996, 2:86-72.

EP03721571 Search Report dated Feb. 28, 2006.
EP06022033.2 Search Report mailed Feb. 12, 2008.
EP05769609.8 Office Action mailed Jun. 1, 2011.
EP06808953.1 Search Report and Opinion mailed Jul. 16, 2008.
TW094110256 Search Report mailed Mar. 29, 2011.
PCT/US03/10750 Search Report mailed Jul. 20, 2005.
PCT/IB02/02188 Search Report mailed Dec. 16, 2002.
PCT/IB02/02188 IPRP mailed Jul. 18, 2003.
PCT/IB06/02771 Search Report mailed Feb. 27, 2007.
PCT/IB06/02771 IPRP and Written Opinion mailed Jan. 10, 2008.
PCT/IB05/02479 Search Report mailed Jan. 27, 2006.
PCT/IB05/02479 IPRP and Written Opinion mailed Oct. 4, 2006.
EP10191602.1 Search Report and Opinion mailed Jul. 27, 2011.

B.

C.

A.

B.

A.

B.

C.

A.

B.

SEQUENCE LISTING

<160> NUMBER OF SEQ ID NOS: 21

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Ser Ala Pro Asp Thr Arg Pro Ala Pro Gly Ser Thr Ala Pro Pro
1               5                   10                  15

Ala His Gly Val
            20

<210> SEQ ID NO 2
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Thr-GalNAc-alpha-1
<220> FEATURE:
<221> NAME/KEY: MOD_RES
<222> LOCATION: (12)..(12)
<223> OTHER INFORMATION: Ser-GalNAc-alpha-1
<220> FEATURE:
<221> NAME/KEY: MOD_RES
<222> LOCATION: (13)..(13)
<223> OTHER INFORMATION: Thr-GalNAc-alpha-1
<220> FEATURE:
<221> NAME/KEY: MOD_RES
<222> LOCATION: (26)..(26)
<223> OTHER INFORMATION: Thr-GalNAc-alpha-1
<220> FEATURE:
<221> NAME/KEY: MOD_RES
<222> LOCATION: (32)..(32)
<223> OTHER INFORMATION: Ser-GalNAc-alpha-1
<220> FEATURE:
<221> NAME/KEY: MOD_RES
<222> LOCATION: (33)..(33)
<223> OTHER INFORMATION: Thr-GalNAc-alpha-1
<220> FEATURE:
<221> NAME/KEY: MOD_RES
<222> LOCATION: (41)..(42)
<223> OTHER INFORMATION: C14 lipid covalently attached to a Ser residue

<400> SEQUENCE: 2

Thr Ser Ala Pro Asp Thr Arg Pro Ala Pro Gly Ser Thr Ala Pro Pro
1               5                   10                  15

Ala His Gly Val Thr Ser Ala Pro Asp Thr Arg Pro Ala Pro Gly Ser
            20                  25                  30

Thr Ala Pro Pro Ala His Gly Val Ser Ser Leu
            35                  40

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)

```
<223> OTHER INFORMATION: Asp or Glu
<220> FEATURE:
<221> NAME/KEY: MOD_RES
<222> LOCATION: (6)..(6)
<223> OTHER INFORMATION: Thr or Ser
<220> FEATURE:
<221> NAME/KEY: MOD_RES
<222> LOCATION: (16)..(16)
<223> OTHER INFORMATION: Pro, Ala, Gln or Thr

<400> SEQUENCE: 3

Thr Ser Ala Pro Xaa Xaa Arg Pro Ala Pro Gly Ser Thr Ala Pro Xaa
1               5                   10                  15

Ala His Gly Val
            20

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Ala Pro Asp Thr Arg Pro
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Asp Thr Arg Pro
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Pro Ala Pro Gly Ser
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Pro Ala His Gly Val Thr
1               5

<210> SEQ ID NO 8
<211> LENGTH: 5
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 8

Pro Asp Thr Arg Pro
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Pro Asp Thr Arg Pro Ala Pro Gly Ser
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Pro Asp Thr Arg Pro
1               5

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Val Thr Ser Ala Pro Asp Thr Arg Pro Ala Pro Gly Ser Thr Ala
1               5                   10                  15

Pro Pro Ala His
            20

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Arg Pro Ala Pro Gly Ser Thr Ala Pro Pro Ala His Gly Val Thr
1               5                   10                  15

Ser Ala Pro Asp
            20

<210> SEQ ID NO 13
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Thr Arg
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Thr Arg Pro
1

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Ala Pro Asp Thr Arg Pro
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Ser Ala Pro Asp Thr Arg Pro Ala
1               5

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Val Thr Ser Ala Pro Asp Thr Arg Pro Ala Pro Gly Ser Thr Ala
1               5                   10                  15

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cancer-associated carbohydrate epitope modified
      Thr
<220> FEATURE:
<221> NAME/KEY: MOD_RES
<222> LOCATION: (2)..(2)
<223> OTHER INFORMATION: Cancer-associated carbohydrate epitope modified
      Ser
<220> FEATURE:
<221> NAME/KEY: MOD_RES

```
<222> LOCATION: (6)..(6)
<223> OTHER INFORMATION: Cancer-associated carbohydrate epitope modified
      Thr
<220> FEATURE:
<221> NAME/KEY: MOD_RES
<222> LOCATION: (12)..(12)
<223> OTHER INFORMATION: Cancer-associated carbohydrate epitope modified
      Ser
<220> FEATURE:
<221> NAME/KEY: MOD_RES
<222> LOCATION: (13)..(13)
<223> OTHER INFORMATION: Cancer-associated carbohydrate epitope modified
      Thr

<400> SEQUENCE: 18

Thr Ser Ala Pro Asp Thr Arg Pro Ala Pro Gly Ser Thr Ala Pro Pro
1               5                   10                  15

Ala His Gly Val
            20

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Cancer-associated carbohydrate epitope modified
      Thr
<220> FEATURE:
<221> NAME/KEY: MOD_RES
<222> LOCATION: (12)..(12)
<223> OTHER INFORMATION: Cancer-associated carbohydrate epitope modified
      Ser
<220> FEATURE:
<221> NAME/KEY: MOD_RES
<222> LOCATION: (13)..(13)
<223> OTHER INFORMATION: Cancer-associated carbohydrate epitope modified
      Thr

<400> SEQUENCE: 19

Thr Ser Ala Pro Asp Thr Arg Pro Ala Pro Gly Ser Thr Ala Pro Pro
1               5                   10                  15

Ala His Gly Val
            20

<210> SEQ ID NO 20
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(36)
<223> OTHER INFORMATION: Lipidated-Ser

<400> SEQUENCE: 20

Cys Thr Arg Pro Asn Asn Asn Thr Arg Lys Ser Ile Arg Ile Gln Arg
1               5                   10                  15

Gly Pro Gly Arg Ala Phe Val Thr Ile Gly Lys Ile Gly Asn Met Arg
            20                  25                  30

Gln Ala Ser Ser Leu
        35

<210> SEQ ID NO 21
```

```
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Thr Ala Pro Pro Ala His Gly Val Thr Ser Ala Pro Asp Thr Arg
1               5                   10                  15

Pro Ala Pro Gly Ser Thr Ala Pro Pro Ala Lys Gly
            20                  25
```

MUC1 BASED GLYCOLIPOPEPTIDE VACCINE WITH ADJUVANT

CROSS-REFERENCE

This continuation application claims priority to U.S. application Ser. No. 13/403,679, filed Feb. 23, 2012, which claims the benefit of U.S. Provisional Application No. 61/446,332, filed Feb. 24, 2011 and U.S. Provisional Application No. 61/470,449, filed Mar. 31, 2011, each of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jun. 29, 2012, is named 34395-826-301-SeqLst.txt and is 7,839 bytes in size.

BACKGROUND OF THE INVENTION

Cancer immunotherapy directs the immune system to recognize tumor-associated antigens and attack cancer cells.

SUMMARY OF THE INVENTION

Provided herein are immunogenic vaccine formulations that harness the immune system for treatment of malignancies. In some embodiments, the immunotherapeutic formulations described herein elicit antigen-specific B-cell and/or T-cell responses. In some embodiments, the vaccine formulations described herein comprise synthetic antigens that elicit an immune response which recognizes tumor-associated antigens and attacks cancer cells. The immunogenic vaccine formulations described herein augment the efficacy of existing cancer treatment regimens.

Provided herein are liposomal vaccine formulations comprising:

(a) a peptide comprising at least two copies of a core tandem repeat:

```
                            (SEQ ID NO: 1)
TSAPDTRPAPGSTAPPAHGV,
``` or a sequence at least 85% identical to SEQ ID NO: 1, or linear permutations thereof;
  wherein
    S and T are independently, at each occurrence, optionally substituted with a cancer-associated carbohydrate epitope Te;

(b) a lipopeptide covalently attached to (a) having the formula:

$$H_2N\text{-}(aa_1)^*(aa_2)^*(aa_3)\text{-}OH$$

wherein
    $aa_1$ is independently, at each occurrence, selected from S, T, K, R or C;
    $aa_2$ is independently, at each occurrence, selected from S, T, K, R or C;
    $aa_3$ is independently, at each occurrence, selected from L or G;
    * independently, at each occurrence, represents a lipid covalently attached to an amino acid residue;

(c) an adjuvant of Formula I:

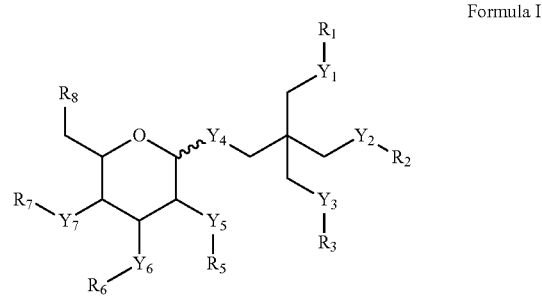

Formula I wherein at least one of $R_1$, $R_2$, $R_3$, $R_5$, $R_6$, and $R_7$ is a strongly lipophilic group selected from the group consisting of (i)

(ii)
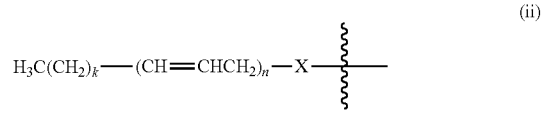

(iii)
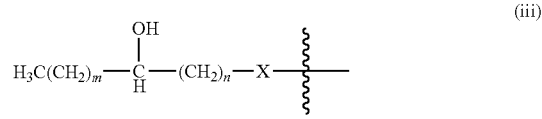

(iv)
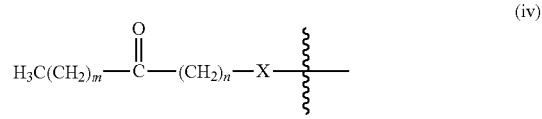

(v)
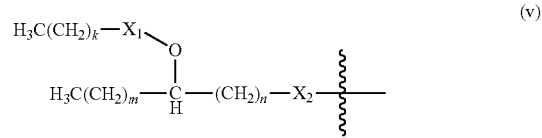

(vi)
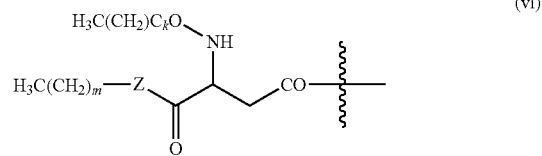

(vii)
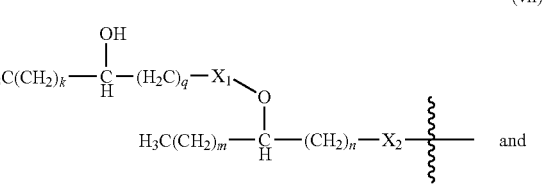

and (viii)
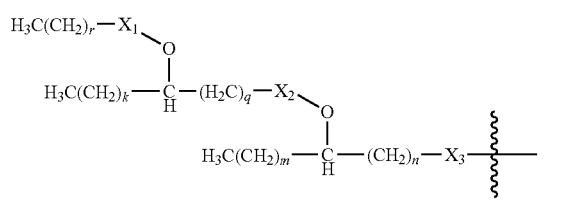

wherein X, $X_1$, $X_2$, and $X_3$ are independently —CO— or —$CH_2$—;

Z is —NH— or —O—;

k, m, and r are independently an integer of 0 to 30 inclusive, n and q are independently an integer of 0 to 6 inclusive;

wherein $Y_4$ is a spacer selected from the group consisting of —O—, —S—, and —NH— wherein, at least one of $Y_1R_1$, $Y_2R_2$, $Y_3R_3$, $Y_5R_5$, $Y_6R_6$ and $Y_7R_7$ is a monovalent phosphate equivalent (MPE), wherein each monovalent phosphate equivalent is, independently,
(a) —R'—C(O)OH where R' is a substituted or unsubstituted alkyl group of 1-4 carbons, or
(b) selected independently from the group consisting of —OB(OH)OR, —OP(O)(OH)OR, —OS(O)(O)(OH)OR, and —OP(=O)(OH)—O—P(=O)(OH)OR,
where R is hydrogen, or a substituted or unsubstituted alkyl group of 1-4 carbons,
and if R is a substituted alkyl group, the substitutions are —OH or —$NH_2$, wherein $R_8$ is selected from the group consisting of H, OH, $OR_9$, a moiety which in combination with $Y_8$ forms a monovalent phosphate equivalent as previously defined, and a group (i)-(viii) as defined above; wherein $R_9$ is an alkyl or acyl group of 1 to 10 carbon length; and wherein the glycosidic linkage is α or β;

or a pharmaceutically acceptable salt thereof;

or an adjuvant of Formula II:

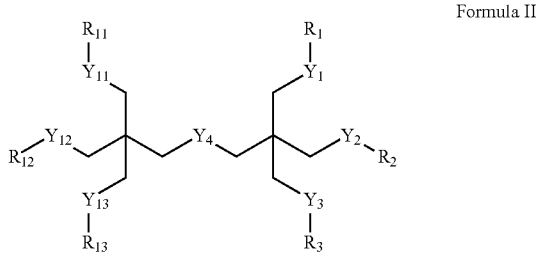

Formula II wherein at least one of $R_1$, $R_2$, $R_3$, $R_{11}$, $R_{12}$ and $R_{13}$ is a strongly lipophilic group selected from the group consisting of (i)-(viii) above;

wherein $Y_4$ is a spacer selected from the group consisting of —O—, —S—, and —NH— and wherein at least one of $Y_1R_1$, $Y_2R_2$, $Y_3R_3$, $Y_{11}R_{11}$, $Y_{12}R_{12}$ and $Y_{13}R_{13}$ is independently a monovalent phosphate equivalent as previously defined;

wherein the following limitations apply to both (I) and (II) above:

$Y_1$, $Y_2$, $Y_3$, $Y_5$, $Y_6$, $Y_7$, $Y_{11}$, $Y_{12}$ and $Y_{13}$ are spacers independently selected from the group consisting of —O—, —S—, and —NH—;

$R_1$, $R_2$, $R_3$, $R_5$, $R_6$, $R_7$, $R_{11}$, $R_{12}$ and $R_{13}$ are independently hydrogen,
a moiety which with the commonly numbered Y group forms monovalent phosphate equivalent as previously defined, or
a strongly lipophilic group selected from the group consisting of (i)-(viii) above; the strongly lipophilic groups of said compound collectively provide at least two major carbon chains, and
the major carbon chains of said strongly lipophilic groups collectively provide at least 30 carbon atoms;

or a pharmaceutically salt thereof; and (d) one or more carrier lipids.

In some embodiments, the formulation is a lyophilized powder, a dried thin-film or a dried powder. In some embodiments, the formulation is a lyophilized powder. In some embodiments, the vaccine formulation is a suspension in water, an emulsion, or a suspension in oil. In some embodiments, the formulation is a suspension in water. In some embodiments, the formulation further comprises tert-butanol.

In some embodiments, the core tandem repeat sequence has at least 90% homology with the sequence in (a). In some embodiments, the core tandem repeat sequence has at least 95% homology with the sequence in (a).

In some embodiments, the carrier lipid is selected from dimyristoyl phosphatidylglycerol (DMPG), dipalmitoyl phosphatidylcholine (DPPC), phosphatidylcholine (PC; lecithin), phosphatidic acid (PA), phosphatidylglycerol (PG), phosphatidylethanolamine (PE), phosphatidylserine (PS). Other suitable phospholipids further include distearoylphosphatidylcholine (DSPC), dimyristoylphosphatidylcholine (DMPC), dipalmitoylphosphatidyglycerol (DPPG), distearoylphosphatidyglycerol (DSPG), dipalmitoylphosphatidic acid (DPPA); dimyristoylphosphatidic acid (DMPA), distearoylphosphatidic acid (DSPA), dipalmitoylphosphatidylserine (DPPS), dimyristoylphosphatidylserine (DMPS), distearoylphosphatidylserine (DSPS), dipalmitoylphosphatidyethanolamine (DPPE), dimyristoylphosphatidylethanolamine (DMPE), distearoylphosphatidylethanolamine (DSPE), or a pharmaceutically acceptable salt thereof, or combination thereof.

In some embodiments, the carrier lipid is selected from dimyristoyl phosphatidylglycerol (DMPG), dipalmitoyl phosphatidylcholine (DPPC), or a pharmaceutically acceptable salt thereof, or combination thereof.

In some embodiments, the formulations further comprise cholesterol.

In some embodiments, the lipid covalently attached to an amino acid residue is independently, at each occurrence, selected from myristoyl, palmitoyl, lauryl, stearoyl, decanoyl, and octanoyl chains, or a combination thereof. In some embodiments, the lipid covalently attached to the amino acid residue is independently, at each occurrence, a myristoyl chain.

In some embodiments, (b) is attached to the carboxy terminus of (a). In some embodiments, (b) is attached to the amino terminus of (a).

In some embodiments, (a)+(b) and (c) are in a weight (a)+(b): weight(c) ratio of from about 1:10 to about 10:1. In some embodiments, (a)+(b) and (c) are in a weight (a)+(b): weight(c) ratio of from about 1:5 to about 5:1. In some embodiments, (a)+(b) and (c) are in a weight (a)+(b): weight (c) ratio of from about 1:2 to about 2:1.

In some embodiments, Te is, independently at each occurrence, selected from

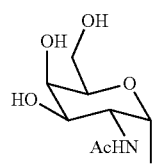

Tn

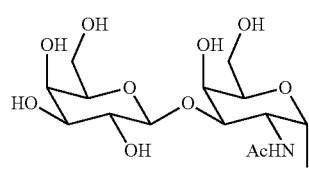

TF

-continued

STn
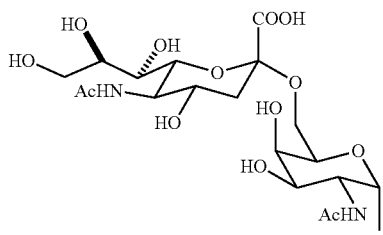

STF
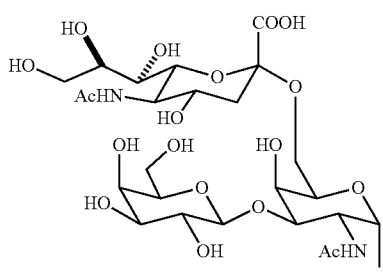

Tn′
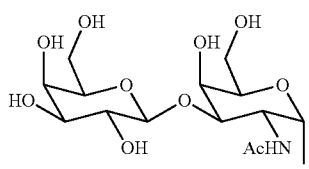

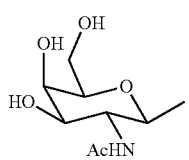

TF′
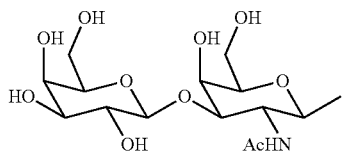

STn′
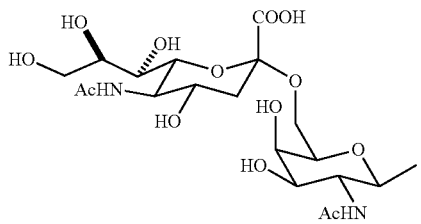

STF′
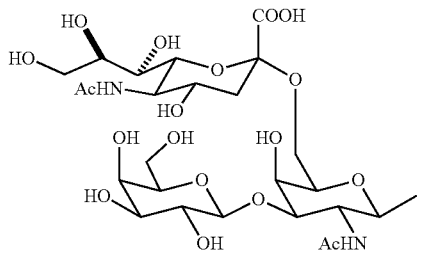

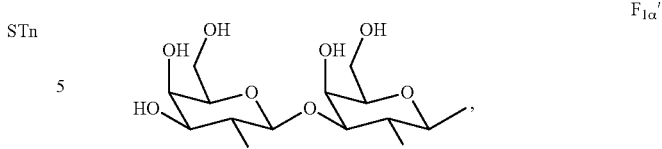

and a T-hapten.

In some embodiments, Te is, independently at each occurrence, selected from

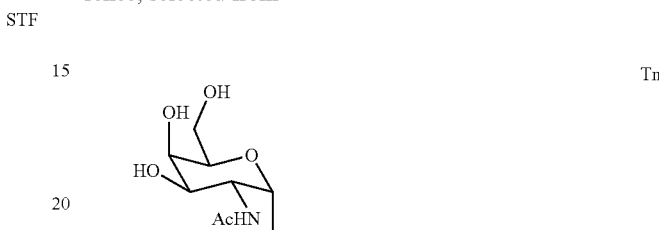

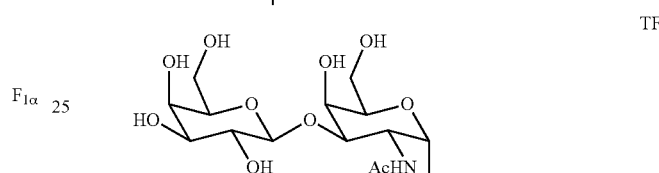

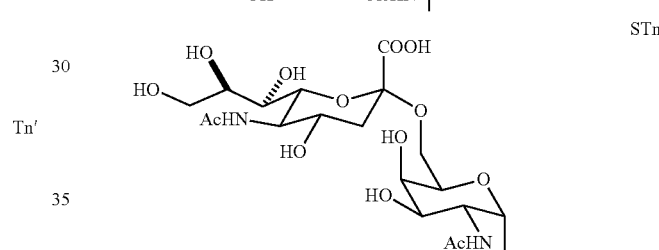

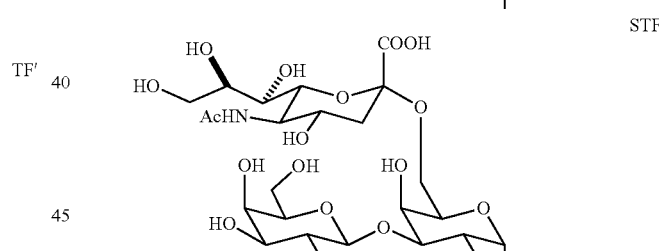

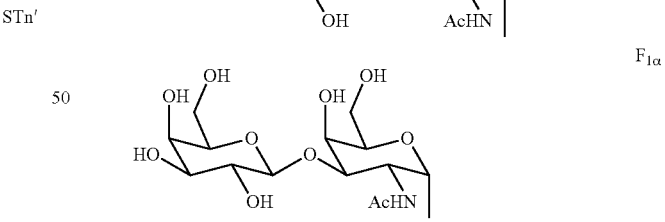

and a T-hapten.

In some embodiments, the peptide is substituted with at least one cancer-associated carbohydrate Te. In some embodiments, the peptide is substituted with at least two Te. In some embodiments, the peptide is substituted with at least three Te. In some embodiments, the peptide is substituted with at least four Te. In some embodiments, the peptide is substituted with at least five Te. In some embodiments, the peptide is substituted with at least five Te. In some embodiments, the peptide is substituted with at least six Te. In some embodiments, the peptide is substituted with at least seven Te.

In some embodiments, the peptide is substituted with at least eight Te. In some embodiments, the peptide is substituted with at least nine Te. In some embodiments, the peptide is substituted with at least ten Te.

In some embodiments, the adjuvant is of Formula I, or is a pharmaceutically acceptable salt thereof. In some embodiments, the adjuvant is of Formula II, or is a pharmaceutically acceptable salt thereof.

In some embodiments, $Y_4$ is —S—. In some embodiments, $Y_4$ is —NH—. In some embodiments, $Y_4$ is —O—.

In some embodiments, at least one strongly lipophilic group satisfies (i) and for at least one such group, k is an integer 4-30. In some embodiments, at least one strongly lipophilic group satisfies (ii), and for at least one such group, and 2k+3n is an integer 4-30. In some embodiments, at least one strongly lipophilic group satisfies (iii), and for at least one such group, and m+n+1 is 4-30. In some embodiments, at least one strongly lipophilic group satisfies (iv), and for at least one such group, m+n+1 is 4-30. In some embodiments, at least one strongly lipophilic group satisfies (v), and for at least one such group, m+n+k+1 is 4-30. In some embodiments, at least one strongly lipophilic group satisfies (vi), and for at least one such group, k+m+2 is 4-30. In some embodiments, at least one strongly lipophilic group satisfies (vii), and for at least one such group, k+q+m+n is 4-30. In some embodiments, at least one strongly lipophilic group satisfies (viii), and for at least one such group, r+k+q+m+n is 5-30.

In some embodiments, $Y_1, Y_2, Y_3, Y_4, Y_5, Y_6, Y_7, Y_{11}, Y_{12}$ and $Y_{13}$ are independently —O— or —NH—. In some embodiments, $Y_1, Y_2, Y_3, Y_4, Y_5, Y_6$ and $Y_7$, are independently —O— or —NH—. In some embodiments, $Y_1, Y_2, Y_3, Y_4, Y_{11}, Y_{12}, Y_{13}$ are independently —O— or —NH—.

In some embodiments, $Y_4$ is —O—. In some embodiments, each monophosphate equivalent is —OP(O)(OH)(OH).

In some embodiments, an adjuvant of Formula I is a compound, wherein
$Y_4$ is —O—;
$Y_1, Y_2,$ and $Y_7$ are —O—;
$Y_3, Y_5$ and $Y_6$ are independently —O— or —NH—;
$R_1, R_3, R_5$ and $R_6$ are independently hydrogen or a strongly lipophilic group selected from (i)-(viii);
at least one of $R_1, R_3, R_5,$ and $R_6$ is not hydrogen;
$R_2$ and $R_7$ are independently selected from the group consisting of H, —P(O)(OH)$_2$, —SO$_3$H, —P(O)(OH)(OCH$_2$CH$_2$NH$_2$), and —CH$_2$COOH; and
$R_8$ is selected from the group consisting of H, OH, OSO$_3$H, and OR$_9$, wherein $R_9$ is an alkyl or acyl group of 1 to 10 carbon length.

In some embodiments an adjuvant of Formula I is a compound, wherein
$Y_4$ is —O—;
$Y_2$ and $Y_{12}$ are —O-p;
$Y_1, Y_3, Y_{11},$ and $Y_{13}$ are independently chosen from the group consisting of —O—, —NH— and —S—;
$R_1, R_3, R_{11},$ and $R_{13}$ are independently hydrogen, or a strongly lipophilic group selected from (i)-(viii);
at least one of $R_1, R_3, R_5,$ and $R_6$ is not hydrogen; and
$R_2$ and $R_{12}$ are independently selected from the group consisting of H, —P(O)(OH)$_2$, —P(O)(OH)(OCH$_2$CH$_2$NH$_2$), and —CH$_2$COOH.

In some embodiments, $R_1, R_3, R_5$ and $R_6$ are independently hydrogen or a strongly lipophilic group elected from the group consisting of (i)-(viii), at least one $R_1, R_3, R_5$ and $R_6$ is not hydrogen, and $R_2$ and $R_7$ are independently selected from the group consisting of H, —P(O)(OH)$_2$, —SO$_3$H, —, —P(O)(OH)(OCH$_2$CH$_2$NH$_2$), and —CH$_2$COOH; and $R_8$ is selected from the group consisting of H, OH, OSO$_3$H, and OR$_9$ wherein $R_9$ is an alkyl or acyl group of 1 to 10 carbon length.

In some embodiments, $R_1, R_3, R_{11},$ and $R_{13}$ are independently hydrogen, or a strongly lipophilic group selected from (i)-(viii); at least one of $R_1, R_3, R_5,$ and $R_6$ is not hydrogen; and $R_2$ and $R_{17}$ are independently selected from the group consisting of H, —P(O)(OH)$_2$, —P(O)(OH)(OCH$_2$CH$_2$NH$_2$), and —CH$_2$COOH.

In some embodiments of Formula I, each monophosphate equivalent is —OP(O)(OH)(OH). In some embodiments of Formula II, each monophosphate equivalent is —OP(O)(OH)(OH).

In some embodiments, the strongly lipophilic groups of said compound collectively provide at least three major carbon chains, and wherein the major carbon chains of said strongly lipophilic groups collectively provide at least 40 carbon atoms, said adjuvant having immunostimulatory activity. In some embodiments, the strongly lipophilic groups of said compound collectively provide at least four major carbon chains and wherein the major carbon chains collectively provide at least 50 carbon atoms, said adjuvant having immunostimulatory activity. In some embodiments, the strongly lipophilic groups collectively provide six major carbon chains. In some embodiments, each major carbon chain is characterized by 10, 12, 14, 16, 18 or 20 carbon atoms in said chain.

In some embodiments, at least one strongly lipophilic group is one of the structures set forth below:

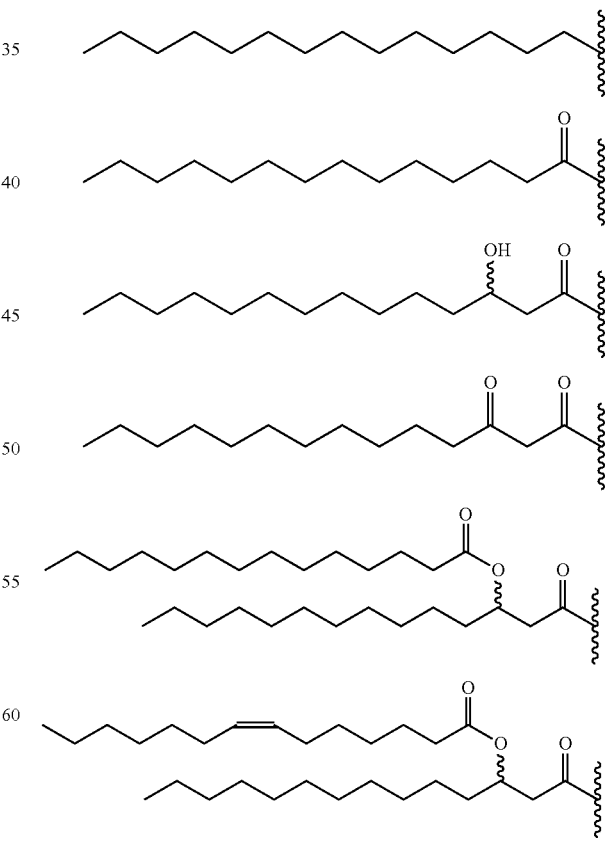

In some embodiments, the at least one strongly lipophilic group comprises an R enantiomer. In some embodiments, the at least one strongly lipophilic group comprises an S enantiomer. In some embodiments, the at least one strongly lipophilic group is a racemate. In some embodiments, the at least one strongly lipophilic group comprises an RR, an RS, an SR or an SS diastereomer. All racemates, enantiomers or diastereomers are contemplated as being within the scope of embodiments presented herein. In some embodiments, the at least one strongly lipophilic group is one of the structures set forth below:

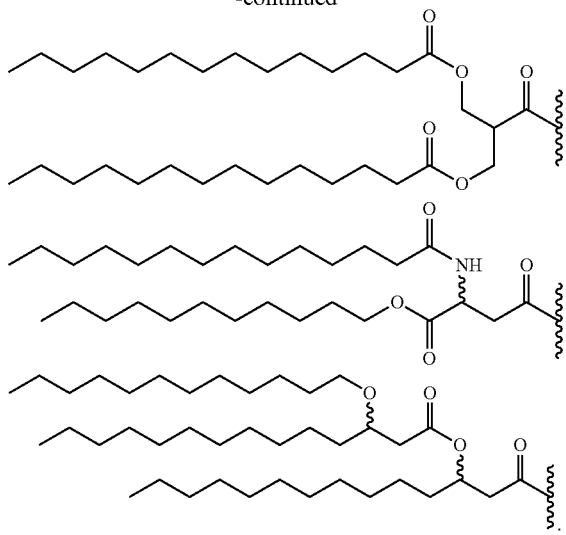

In some embodiments, the at least one strongly lipophilic group is one of the structures set forth below:

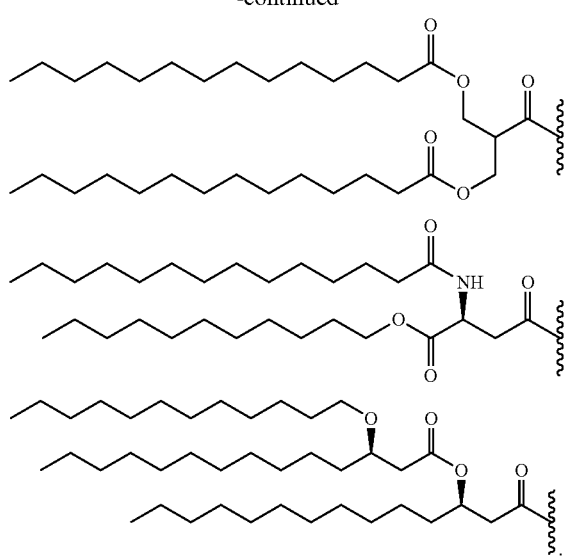

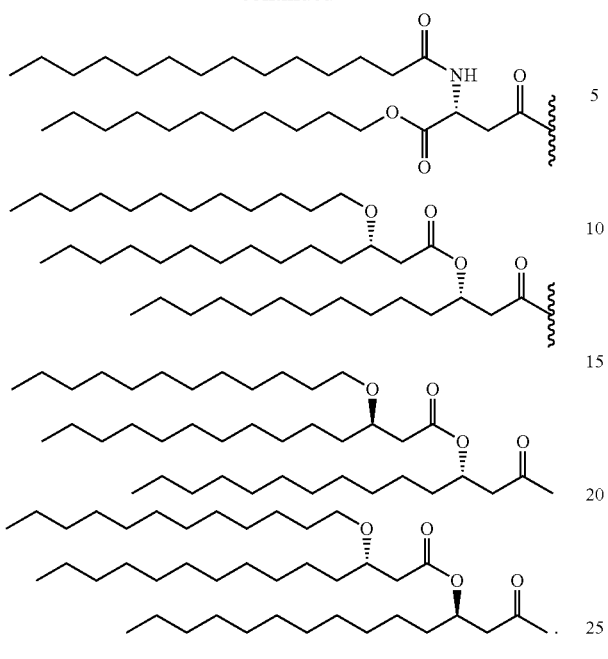

In some embodiments, an adjuvant of Formula I is a PET lipid A analog. In some embodiments, an adjuvant of Formula I has the following structure:

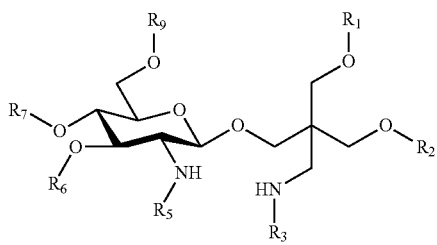

wherein $R_1$, $R_3$, $R_5$ and $R_6$ are independently hydrogen or a lipophilic group selected from the group consisting of

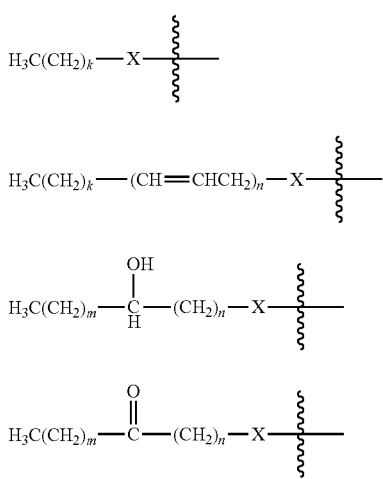

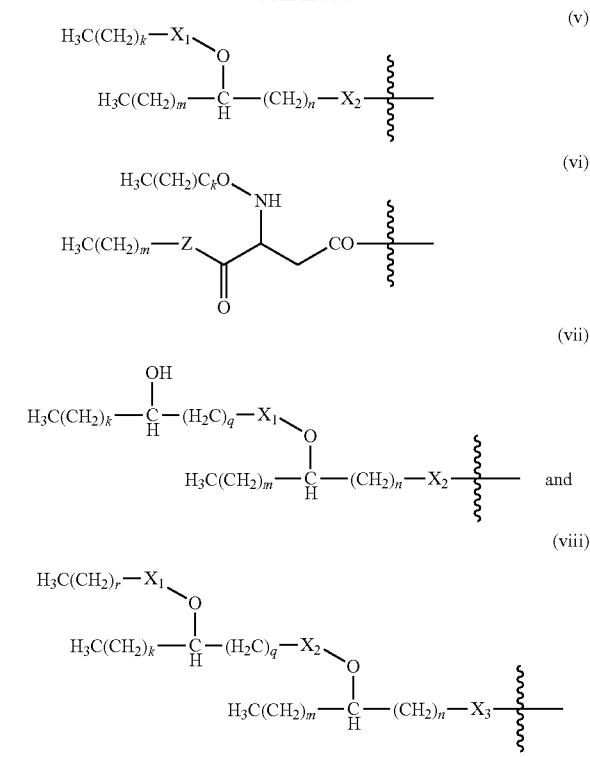

wherein X, $X_1$, $X_2$, and $X_3$ are independently —CO— or —CH$_2$—;

Z is —NH— or —O—;

k, m, and r are independently an integer of 0 to 30 inclusive, n and q are independently an integer of 0 to 6 inclusive;

at least one of $R_1$, $R_3$, $R_5$ and $R_6$ is not hydrogen;

$R_2$ and $R_7$ are independently selected from the group consisting of —P(O)(OH)$_2$, —SO$_3$H, —P(O)(OH)(OCH$_2$CH$_2$NH$_2$), and —CH$_2$COOH; and $R_9$ is H, or an alkyl or acyl group of 1 to 10 carbon length.

In some embodiments, $R_1$ and $R_9$ are hydrogen; $R_2$ is a hydrogen or the phosphono group —P(O)(OH)$_2$; $R_7$ is the phosphono group —P(O)(OH)$_2$; and $R_3$, $R_5$ and $R_6$ are the same or different acyl groups of the following structure

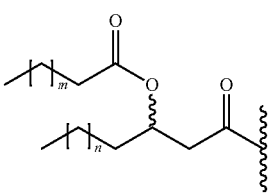

wherein m and n are independently chosen from an integer between 6 to 10 inclusive.

In some embodiments, $R_3$, $R_5$ and $R_6$ are identical.

In some embodiments, an adjuvant has one of the structures set forth below:

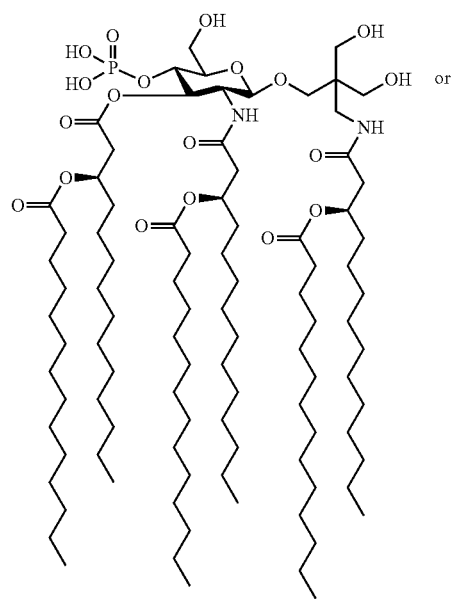
or
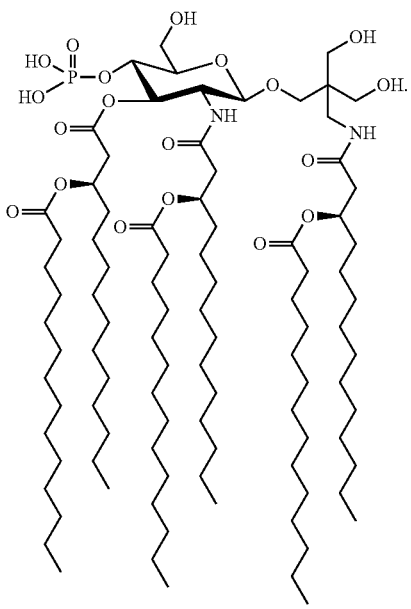
In some embodiments, an adjuvant has one of the structures set forth below:
In some embodiments, an adjuvant has the following structure
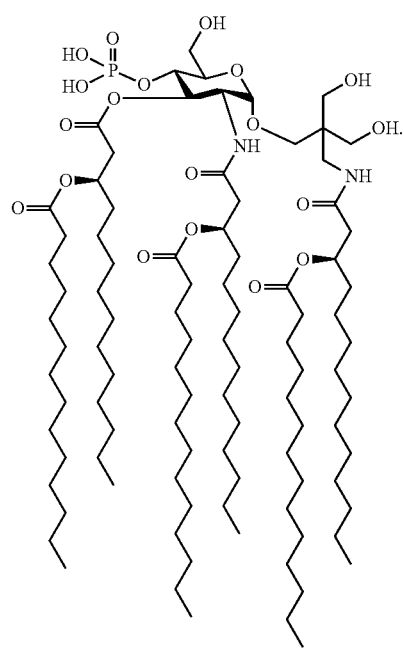
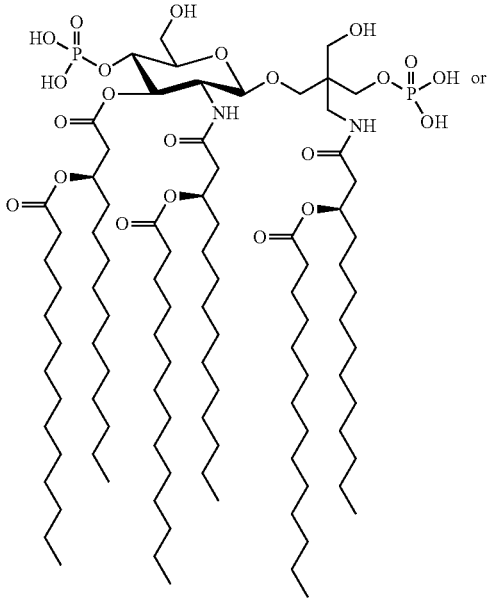
or In some embodiments, an adjuvant has the following structure

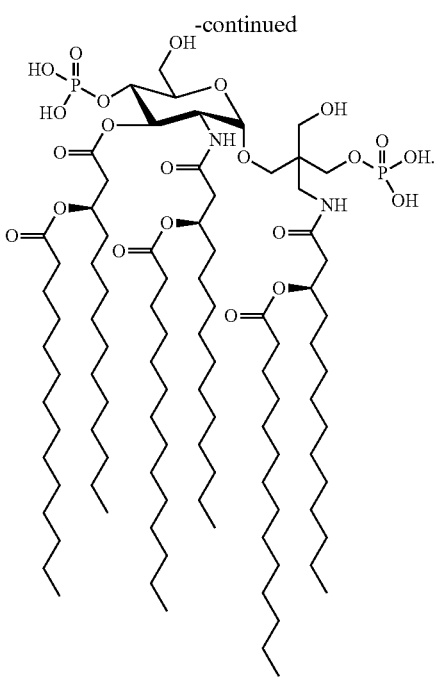

In some embodiments, an adjuvant has the following structure:

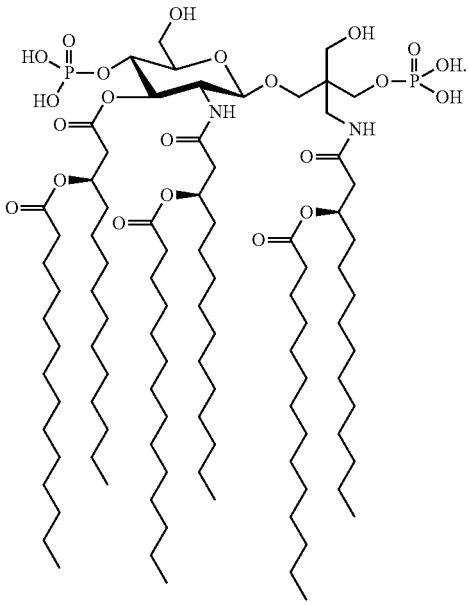

In some embodiments, an adjuvant has the following structure:

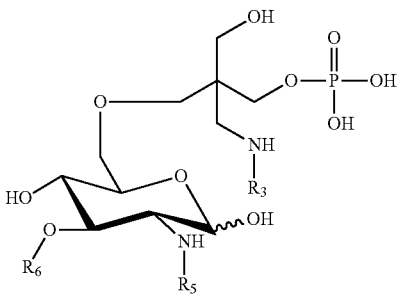

wherein $R_3$, $R_5$ and $R_6$ are the same or different substitution group(s) of the following structure

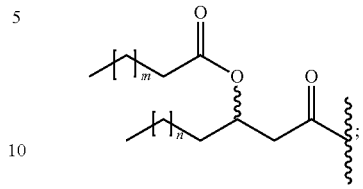

wherein m and n are independently chosen from an integer between 6 to 10 inclusive.

In some of the above embodiments, the adjuvant is a triethylamine salt, a triethanolamine salt or an ammonium salt. In some of the above embodiments, the adjuvant is a triethylamine salt. In some of the above embodiments, the adjuvant is a triethylamine salt of a PET lipid A analog.

In some of the embodiments described above, a comprises H₂N-TSAPDT(Tn)RPAPGS(Tn)T(Tn)APPAHGVTSAPDT(Tn)RPAPGS(Tn)T(Tn)APPAHGVS*S*L-OH (SEQ ID NO: 2), wherein Tn represents GalNAcα1.

In some of the embodiments described above, a liposomal vaccine formulation comprises:
(a) a peptide comprising at least two copies of a core tandem repeat:

SEQ ID NO: 18
T(Te)S(Te)APDT(Te)RPAPGS(Te)T(Te)APPAHGV, or a sequence at least 85% identical to SEQ ID NO: 18, or linear permutations thereof;
wherein
Te represents a cancer-associated carbohydrate epitope;
(b) a lipopeptide covalently attached to (a) having the formula:

H₂N—S*S*L-OH wherein
* independently, at each occurrence, represents a lipid covalently attached to a Serine residue.

In some embodiments described above, a vaccine formulation comprises:
(a) a peptide comprising at least two copies of a core tandem repeat:

SEQ ID NO: 19
TSAPDT(Te)RPAPGS(Te)T(Te)APPAHGV, or a sequence at least 85% identical to SEQ ID NO: 19, or linear permutations thereof;
wherein
Te represents a cancer-associated carbohydrate epitope;
(b) a lipopeptide covalently attached to (a) having the formula:

H₂N—S*S*L-OH wherein
* independently, at each occurrence, represents a lipid covalently attached to a Serine residue.

In some embodiments, the formulation comprises between 2-10 tandem repeats of the core tandem repeat sequence of SEQ ID NO: 18 or SEQ ID NO: 19. In some embodiments, the formulation comprises between 2-5 tandem repeats of the core tandem repeat sequence of SEQ ID NO: 18 or SEQ ID NO: 19. In some embodiments, the formulation comprises 2 tandem repeats of the core tandem repeat sequence of SEQ ID NO: 18 or SEQ ID NO: 19.

In some of such embodiments, the formulation is a lyophilized powder, a dried thin-film or a dried powder. In some of such embodiments, the formulation is a lyophilized powder. In some of such embodiments, the vaccine formulation is a suspension in water, an emulsion, or a suspension in oil. In some embodiments, the formulation is a suspension in water. In some of such embodiments, the formulation further comprises tert-butanol.

In some of such embodiments, the core tandem repeat sequence has at least 90% homology with the sequence in (a) as described in any of the embodiments described above or herein. In some of such embodiments, the core tandem repeat sequence has at least 95% homology with the sequence in (a) as described in any of the embodiments described above or herein.

In some of such embodiments, the carrier lipid is selected from dimyristoyl phosphatidylglycerol (DMPG), dipalmitoyl phosphatidylcholine (DPPC), phosphatidylcholine (PC; lecithin), phosphatidic acid (PA), phosphatidylglycerol (PG), phosphatidylethanolamine (PE), phosphatidylserine (PS). Other suitable phospholipids further include distearoylphosphatidylcholine (DSPC), dimyristoylphosphatidylcholine (DMPC), dipalmitoylphosphatidyglycerol (DPPG), distearoylphosphatidyglycerol (DSPG), dipalmitoylphosphatidic acid (DIVA); dimyristoylphosphatidic acid (DMPA), distearoylphosphatidic acid (DSPA), dipalmitoylphosphatidylserine (DPPS), dimyristoylphosphatidylserine (DMPS), distearoylphosphatidylserine (DSPS), dipalmitoylphosphatidyethanolamine (DPPE), dimyristoylphosphatidylethanolamine (DMPE), distearoylphosphatidylethanolamine (DSPE), or a pharmaceutically acceptable salt thereof, or combination thereof.

In some of such embodiments, the carrier lipid is selected from dimyristoyl phosphatidylglycerol (DMPG), dipalmitoyl phosphatidylcholine (DPPC), or a pharmaceutically acceptable salt thereof, or combination thereof.

In some of such embodiments, the lipid covalently attached to an amino acid residue is independently, at each occurrence, selected from myristoyl, palmitoyl, lauryl, stearoyl, decanoyl, and octanoyl chains, or a combination thereof.

In some of such embodiments, the formulation further comprises cholesterol.

In some of such embodiments, the lipid covalently attached to the Serine residue is independently, at each occurrence, a myristoyl chain.

In some of such embodiments, (b) is attached to the carboxy terminus of (a). In some of such embodiments, (b) is attached to the amino terminus of (a).

In some of such embodiments, (a)+(b) and (c) are in a weight (a)+(b): weight(c) ratio of from about 1:10 to about 10:1. In some of such embodiments, (a)+(b) and (c) are in a weight (a)+(b): weight(c) ratio of from about 1:5 to about 5:1. In some of such embodiments, (a)+(b) and (c) are in a weight (a)+(b): weight(c) ratio of from about 1:2 to about 2:1.

In some embodiments, Te is Tn, wherein Tn represents GalNAcα1.

In some embodiments, provided herein are liposomal vaccine formulations comprising:
(a) a glycolipopeptide of structure:

SEQ ID NO: 2
H$_2$N-TSAPDT(Tn)RPAPGS(Tn)T(Tn)APPAHGVTSAPDT(Tn)RPAPGS(Tn)T(Tn)APPAHGVS*S*L-OH wherein
Tn represents GalNAcα1; and
* represents, independently at each occurrence, a C14 lipid covalently attached to a Serine residue;
(b) an adjuvant of structure:

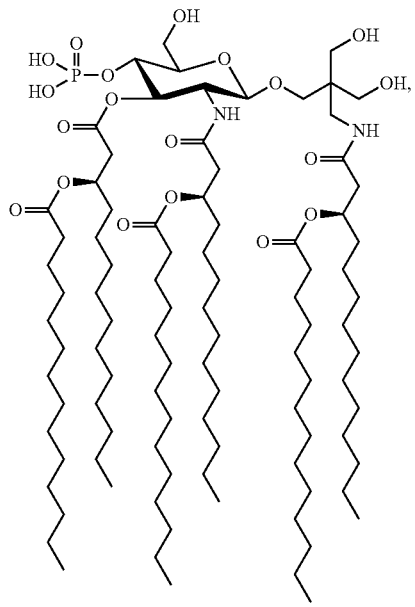

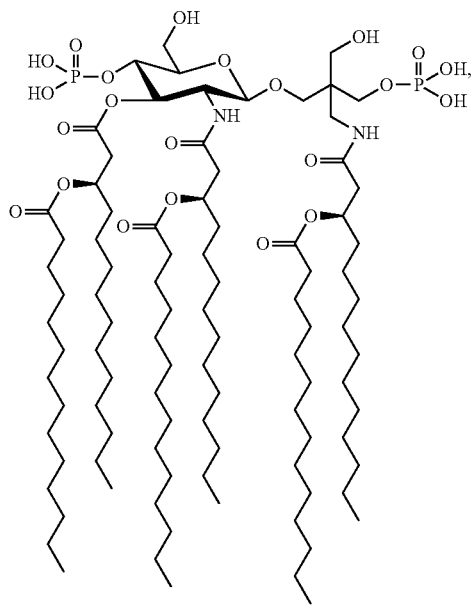

-continued

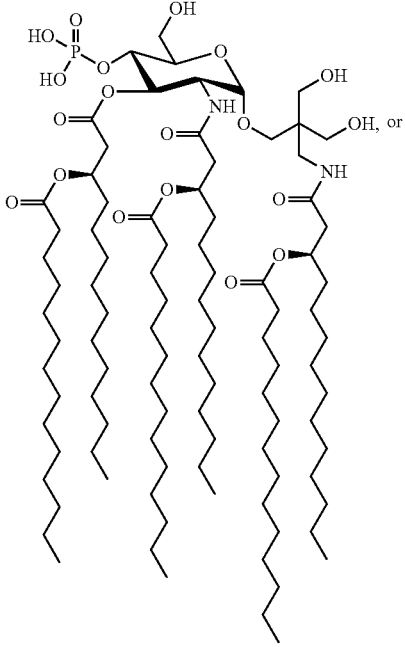

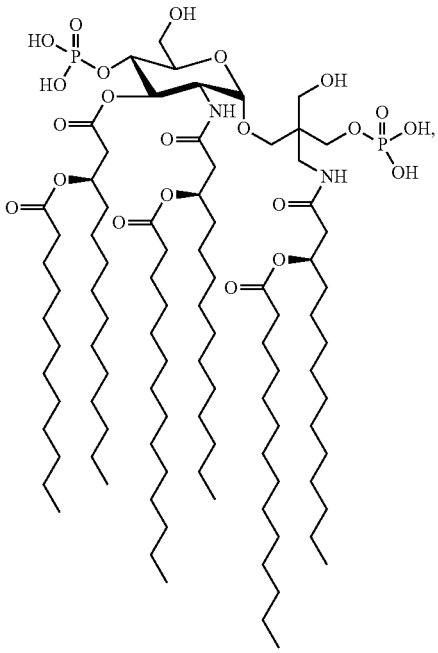

or a pharmaceutically acceptable salt thereof; and (c) a carrier lipid.

In some embodiments, the C14 lipid is a myristoyl chain.
In some embodiments, the adjuvant is

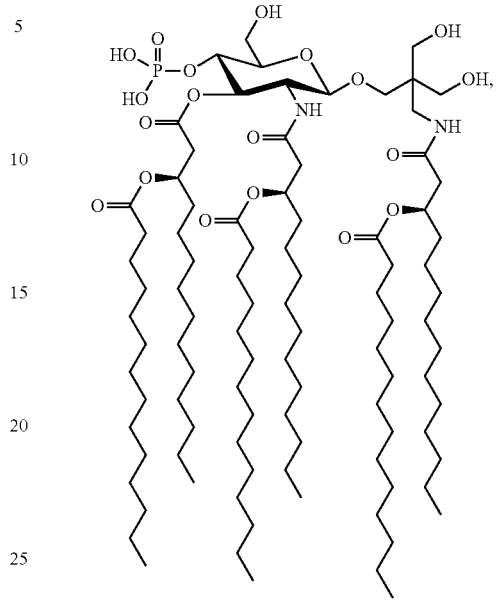

or pharmaceutically acceptable salt thereof.

In some embodiments, the pharmaceutically acceptable salt is a triethylamine salt.

In some embodiments, the carrier lipid is selected from DMPG, DPPC or a pharmaceutically acceptable salt thereof, or combination thereof. In some embodiments, the liposomal vaccine formulation further comprises cholesterol.

In any of the embodiments described above, the formulation comprises one or more MUC1 epitopes. In any of the embodiments described above, the liposomes have a diameter population distribution of 90% (d90)≦about 0.25 μm. In any of the embodiments described above, the liposomes have a diameter population distribution of 90% (d90)≦about 0.22 μm. In any of the embodiments described above, the liposomes have a diameter population distribution of 90% (d90) ≦about 0.20 μm.

In another aspect, provided herein are liposomal vaccine formulations comprising:

(a) a peptide comprising at least two copies of a core tandem repeat:

```
                                         (SEQ ID NO: 1)
              TSAPDTRPAPGSTAPPAHGV,
``` or a sequence at least 85% identical to SEQ ID NO: 1, or linear permutations thereof;
  wherein
    S and T are independently, at each occurrence, optionally substituted with a cancer-associated carbohydrate epitope Te;
(b) a lipopeptide covalently attached to (a) having the formula:

$H_2N$-$(aa_1)$*$(aa_2)$*$(aa_3)$-OH wherein
    $aa_1$ is independently, at each occurrence, selected from S, T, K, R or C;
    $aa_2$ is independently, at each occurrence, selected from S, T, K, R or C;
    $aa_3$ is independently, at each occurrence, selected from L or G;

* independently, at each occurrence, represents a lipid covalently attached to an amino acid residue;

(c) an adjuvant; and (d) one or more carrier lipids.

In some embodiments, the adjuvant is selected from CpG oligodeoxynucleotides (ODN), saponin, a TLR-9 agonist, or a Lipid A analog, or a pharmaceutically acceptable salt thereof, or combination thereof.

In some embodiments, the Lipid A analog is an adjuvant of Formula I:

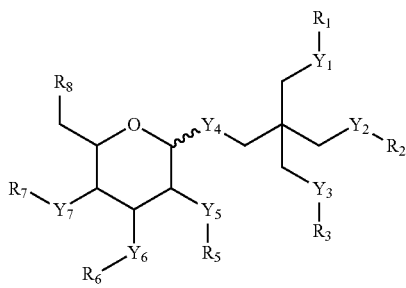

Formula I wherein at least one of $R_1$, $R_2$, $R_3$, $R_5$, $R_6$, and $R_7$ is a strongly lipophilic group selected from the group consisting of

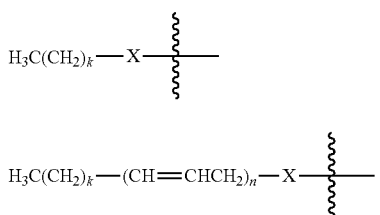 (i)

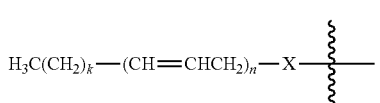 (ii)

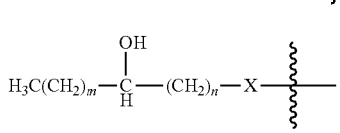 (iii)

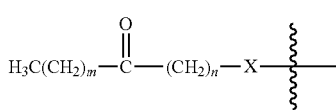 (iv)

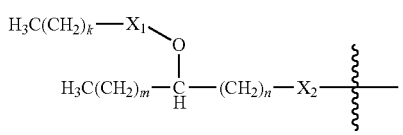 (v)

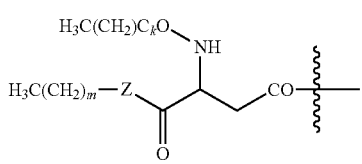 (vi)

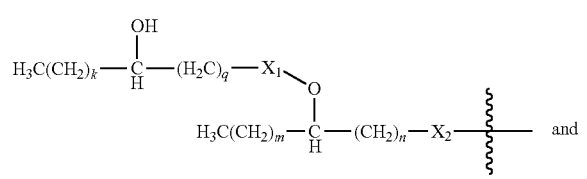 (vii)

and

-continued

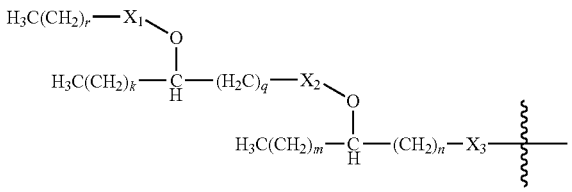 (viii)

wherein X, $X_1$, $X_2$, and $X_3$ are independently —CO— or —CH$_2$—;

Z is —NH— or —O;

k, m, and r are independently an integer of 0 to 30 inclusive, n and q are independently an integer of 0 to 6 inclusive;

wherein $Y_4$ is a spacer selected from the group consisting of —O—, —S—, and —NH— wherein, at least one of $Y_1R_1$, $Y_2R_2$, $Y_3R_3$, $Y_5R_5$, $Y_6R_6$ and $Y_7R_7$ is a monovalent phosphate equivalent (MPE), wherein each monovalent phosphate equivalent is, independently, (a) —R'—C(O)OH, where R' is a substituted or unsubstituted alkyl group of 1-4 carbons, or (b) selected independently from the group consisting of —OB(OH)OR, —OP(O)(OH)OR, —OS(O)(O)(OH)OR, and —OP(=O)(OH)—O—P(=O)(OH)OR, where R is hydrogen, or a substituted or unsubstituted alkyl group of 1-4 carbons, and if R is a substituted alkyl group, the substitutions are —OH or —NH$_2$, wherein $R_8$ is selected from the group consisting of H, OH, OR$_9$, a moiety which in combination with $Y_8$ forms a monovalent phosphate equivalent as previously defined, and a group (i)-(viii) as defined above; wherein $R_9$ is an alkyl or acyl group of 1 to 10 carbon length; and wherein the glycosidic linkage is α or β;

or a pharmaceutically acceptable salt thereof;

or an adjuvant of Formula II:

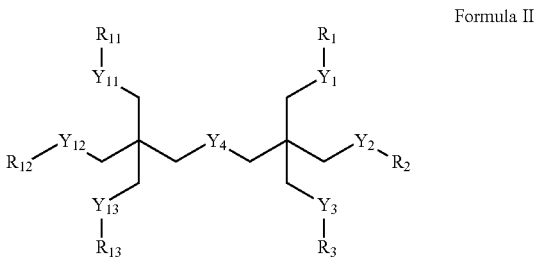

Formula II wherein at least one of $R_1$, $R_2$, $R_3$, $R_{11}$, $R_{12}$ and $R_{13}$ is a strongly lipophilic group selected from the group consisting of (i)-(viii) above;

wherein $Y_4$ is a spacer selected from the group consisting of —O—, —S—, and —NH— and wherein at least one of $Y_1R_1$, $Y_2R_2$, $Y_3R_3$, $Y_{11}R_{11}$, $Y_pR_{12}$ and $Y_{13}R_{13}$ is independently a monovalent phosphate equivalent as previously defined;

wherein the following limitations apply to both (I) and (II) above:

$Y_1$, $Y_2$, $Y_3$, $Y_5$, $Y_6$, $Y_7$, $Y_{11}$, $Y_{12}$, and $Y_{13}$ are spacers independently selected from the group consisting of —O—, —S—, and —NH—;

$R_1$, $R_2$, $R_3$, $R_5$, $R_6$, $R_7$, $R_{11}$, $R_{12}$ and $R_{13}$ are independently hydrogen, a moiety which with the commonly numbered Y group forms monovalent phosphate equivalent as previously defined, or a strongly lipophilic group selected from the group consisting of (i)-(viii) above; the strongly lipophilic groups of said compound collectively provide at least two major carbon chains, and the major carbon chains of said strongly lipophilic groups collectively provide at least 30 carbon atoms;

or a pharmaceutically salt thereof;

In some of such embodiments, the formulation is a lyophilized powder, a dried thin-film or a dried powder. In some embodiments, the formulation is a lyophilized powder. In some of such embodiments, the vaccine formulation is a suspension in water, an emulsion, or a suspension in oil. In some embodiments, the formulation is a suspension in water. In some of such embodiments, the formulation further comprises tert-butanol.

In some of such embodiments, the core tandem repeat sequence has at least 90% homology with the sequence in (a) as described in any of the embodiments described above or herein. In some of such embodiments, the core tandem repeat sequence has at least 95% homology with the sequence in (a) as described in any of the embodiments described above or herein:

In some of such embodiments, the carrier lipid is selected from dimyristoyl phosphatidylglycerol (DMPG), dipalmitoyl phosphatidylcholine (DPPC), phosphatidylcholine (PC; lecithin), phosphatidic acid (PA), phosphatidylglycerol (PG), phosphatidylethanolamine (PE), phosphatidylserine (PS). Other suitable phospholipids further include distearoylphosphatidylcholine (DSPC), dimyristoylphosphatidylcholine (DMPC), dipalmitoylphosphatidyglycerol (DPPG), distearoylphosphatidyglycerol (DSPG), dipalmitoylphosphatidic acid (DPPA); dimyristoylphosphatidic acid (DMPA), distearoylphosphatidic acid (DSPA), dipalmitoylphosphatidylserine (DPPS), dimyristoylphosphatidylserine (DMPS), distearoylphosphatidylserine (DSPS), dipalmitoylphosphatidyethanolamine (DPPE), dimyristoylphosphatidylethanolamine (DMPE), distearoylphosphatidylethanolamine (DSPE), or a pharmaceutically acceptable salt thereof, or combination thereof.

In some of such embodiments, the carrier lipid is selected from dimyristoyl phosphatidylglycerol (DMPG), dipalmitoyl phosphatidylcholine (DPPC), or a pharmaceutically acceptable salt thereof, or combination thereof.

In some of such embodiments, the formulation further comprises cholesterol.

In some of such embodiments, the lipid covalently attached to an amino acid residue is independently, at each occurrence, selected from myristoyl, palmitoyl, lauryl, stearoyl, decanoyl, and octanoyl chains, or a combination thereof. In some of such embodiments, the lipid covalently attached to the amino acid residue is independently, at each occurrence, a myristoyl chain.

In some of such embodiments, (b) is attached to the carboxy terminus of (a). In some of such embodiments, (b) is attached to the amino terminus of (a).

In some of such embodiments, (a)+(b) and (c) are in a weight (a)+(b): weight(c) ratio of from about 1:10 to about 10:1. In some of such embodiments, (a)+(b) and (c) are in a weight (a)+(b): weight(c) ratio of from about 1:5 to about 5:1. In some of such embodiments, (a)+(b) and (c) are in a weight (a)+(b): weight(c) ratio of from about 1:2 to about 2:1.

In some of such embodiments, Te is, independently at each occurrence, selected from

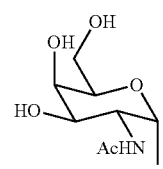
Tn

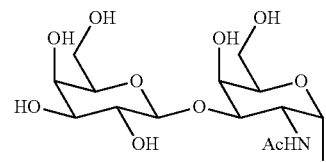
TF

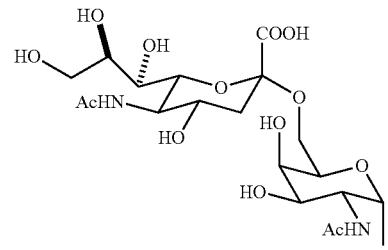
STn

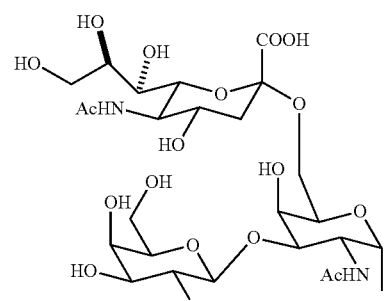
STF

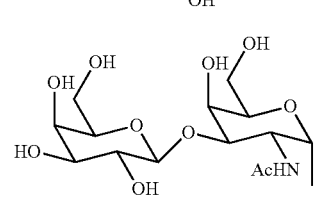
F1a

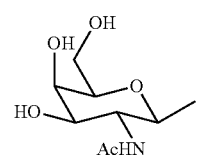
Tn'

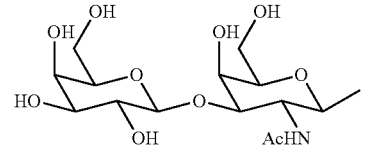
TF'

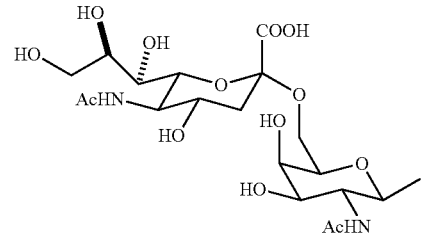
STn'

-continued

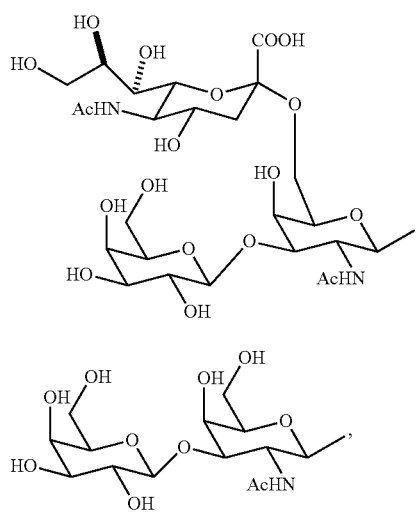

STF'

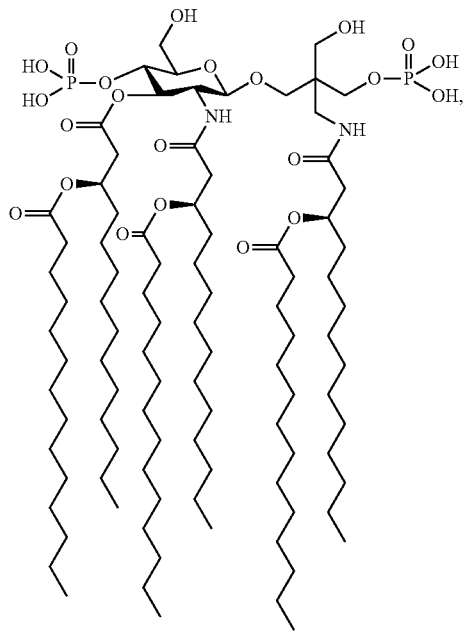

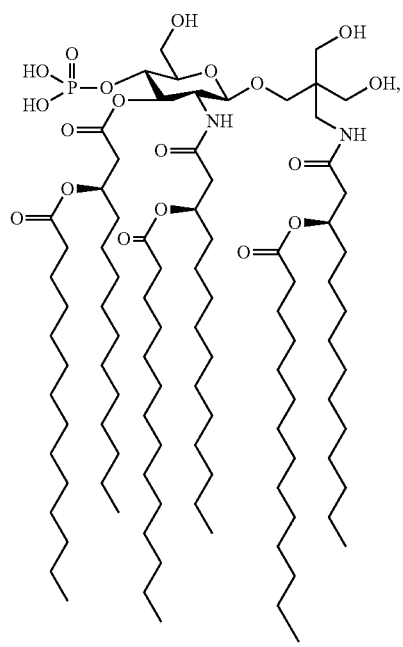

$F_{1a}{}'$ and a T-hapten.

In some of such embodiments, Te is Tn. In some of such embodiments, Te is Tn'. In some of such embodiments, Te is STn. In some of such embodiments, Te is STn'. In some of such embodiments, Te is TF. In some of such embodiments, Te is TF'. In some of such embodiments, Te is STF. In some of such embodiments, Te is STF'. In some of such embodiments, Te is $F_{1\alpha}$. In some of such embodiments, Te is $F_{1\alpha}{}'$. In some of such embodiments, Te is T-hapten. In some of such embodiments, Te is T-hapten'. In some me of such embodiments, Te is, independently at each occurrence, selected from Tn, Tn', STn and STn'. In some of such embodiments, Te is, independently at each occurrence, selected from Tn and STn.

In some of such embodiments, the adjuvant is selected from a compound of Formula I, saponin, CpG ODN, and a TLR-9 agonist, or pharmaceutically acceptable salt thereof, or a combination thereof.

In some of such embodiments, the adjuvant is selected from

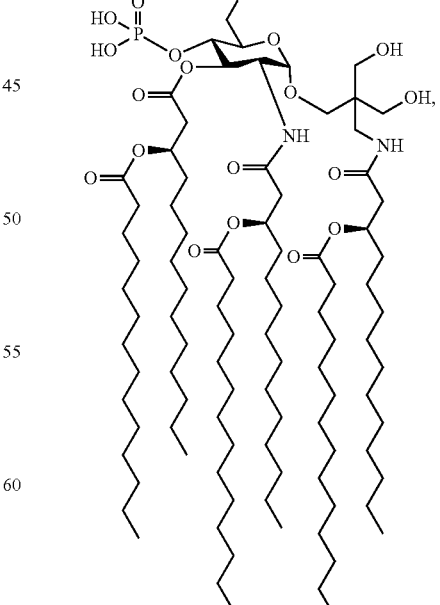

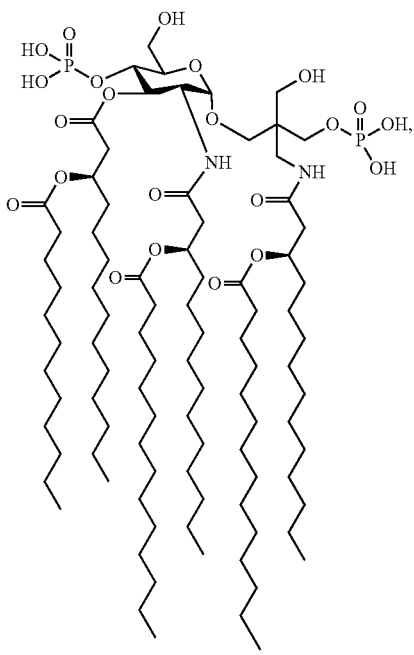

saponin, CpG ODN, and a TLR-9 agonist, or pharmaceutically acceptable salt thereof, or a combination thereof.

In some of such embodiments, a vaccine formulation comprises
(a) a peptide comprising at least two copies of a core tandem repeat:

SEQ ID NO: 18
T(Te)S(Te)APDT(Te)RPAPGS(Te)T(Te)APPAHGV, or a sequence at least 85% identical to SEQ ID NO: 18, or linear permutations thereof;
wherein
Te represents a cancer-associated carbohydrate epitope;
(b) a lipopeptide covalently attached to (a) having the formula:

H₂N—S*S*L-OH wherein
* independently, at each occurrence, represents a lipid covalently attached to a Serine residue.

In some of such embodiments, a vaccine formulation comprises:

(a) a peptide comprising at least two copies of a core tandem repeat:

SEQ ID NO: 19
TSAPDT(Te)RPAPGS(Te)T(Te)APPAHGV, or a sequence at least 85% identical to SEQ ID NO: 19, or linear permutations thereof;

wherein

Te represents a cancer-associated carbohydrate epitope;

(b) a lipopeptide covalently attached to (a) having the formula:

H₂N—S*S*L-OH wherein

* independently, at each occurrence, represents a lipid covalently attached to a Serine residue.

In some of such embodiments, a liposomal vaccine formulation comprises:

(a) a glycolipopeptide of structure:

SEQ ID NO: 2
H₂N-TSAPDT(Tn)RPAPGS(Tn)T(Tn)APPAHGVTSAPDT(Tn)RPAPGS(Tn)T(Tn)APPAHGVS*S*L-OH wherein
Tn represents GalNAcα1; and
* represents, independently at each occurrence, a C14 lipid covalently attached to a Serine residue.

Provided herein are methods for treating an individual suffering from or suspected to be suffering from a cancer that expresses a MUC1 tumor-associated antigen comprising administering to the individual in need thereof, for a period of time, a liposomal vaccine formulation described above.

In some embodiments, the cancer is breast cancer, parotid gland cancer, gastric cancer, esophageal cancer, head and neck cancer, gall bladder cancer, hepatocellular cancer, thyroid cancer, endometrial cancer, multiple myeloma, acute myelogenous leukemia, acute/chronic lymphoblastic leukemia, hairy-cell leukemia, follicular lymphoma, multiple myeloma, plasmacytoma, diffuse large B-cell lymphoma, pancreatic cancer, colon cancer, prostate cancer, ovarian cancer, adenocarcinoma of the lung, squamous cell lung cancer, small cell lung cancer, non-small cell lung cancer, renal cancer, urinary bladder cancer, or urinary tract cancer.

In some embodiments, the methods described above further comprise measuring an immune response in the individual. In some embodiments, measuring the immune response in the treated individual comprises measuring T-cell proliferation in the individual.

In some embodiments, the period of time is selected from at least about 5 days, at least about 1 week, at least about 2 weeks, at least about 4 weeks, at least about 8 weeks, at least about 16 weeks, at least about 20 weeks, at least about 24 weeks, at least about 28 weeks, at least about 32 weeks, at least about 36 weeks, at least about 40 weeks, at least about 44 weeks, at least about 48 weeks, at least about 52 weeks, at least about 60 weeks, at least about 68 weeks, at least about 72 weeks, at least about 80 weeks, at least about 88 weeks, at least about 96 weeks, and at least about 104 weeks.

In some embodiments, the vaccine composition is administered by an intramuscular, intravenous, subcutaneous, intranodal, intratumoral, intraperitoneal or intradermal injection. In some embodiments, the vaccine composition is administered by subcutaneous injection. In some embodiments, the vaccine composition is administered via a pump. In some embodiments, the vaccine composition is administered via an implanted pump (e.g., via an Alzet® osmotic pump).

In some embodiments, the individual is treated with cyclophosphamide, daclizumab or imatinib prior to treatment with a vaccine formulation described above.

Also provided herein are methods for inducing and/or sustaining a cellular and humoral immune response in an individual comprising administering to an individual, for a period of time, a liposomal vaccine formulation described above. In some embodiments, the methods described above further comprise measuring T-cell proliferation in the individual. In other embodiments, the methods described above comprise measuring antibody production in the individual.

Also provided herein are methods for treating a disease, disorder or condition associated with hypoglycosylated MUC1 in an individual comprising administering to an individual having hypoglycosylated MUC1, for a period of time, a liposomal vaccine formulation described above. In some embodiments, the hypoglycosylated MUC1 in the individual is associated with a cancer. In other embodiments, the liposomal vaccine formulation described above induces and/or sustains an immune response specific to hypoglycosylated MUC1 in the individual. In some instances, the immune response is a cellular immune response. In other instances, the immune response is a humoral immune response.

Incorporation by Reference

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
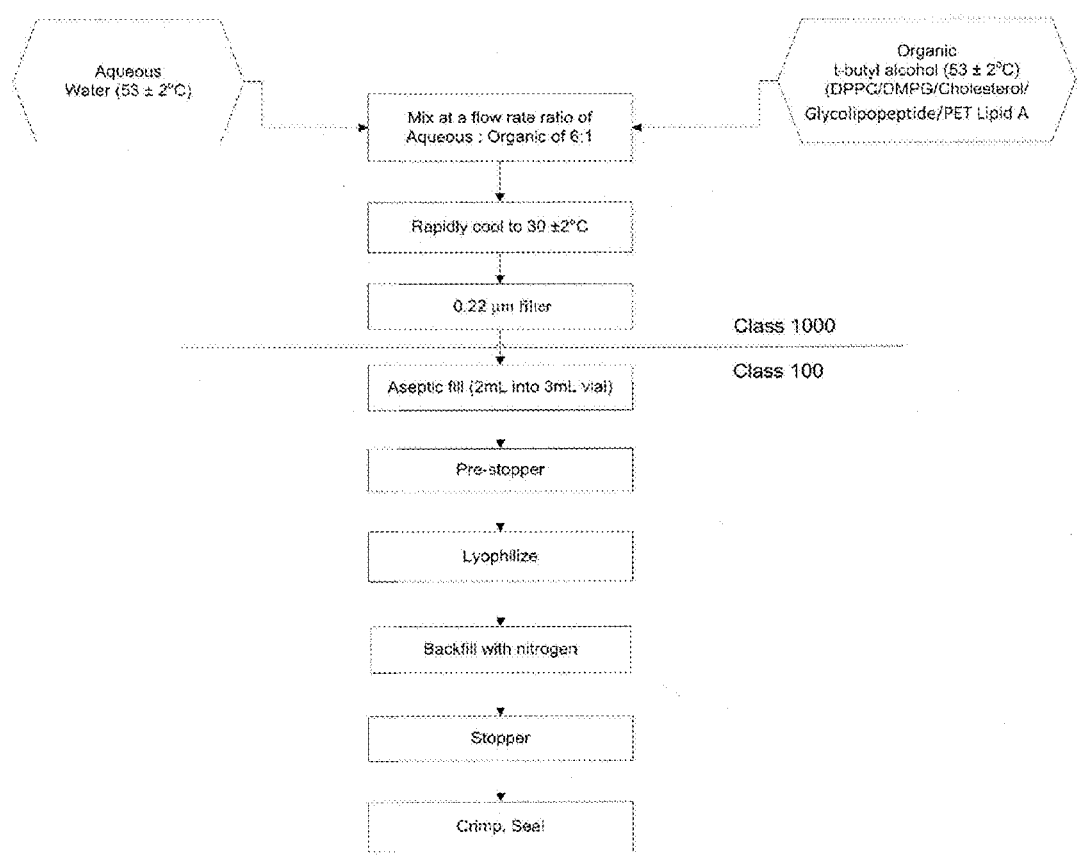
FIG. 1 illustrates a process for synthesis of a liposomal vaccine formulation.

There are many clinically useful therapies for treatment of cancer. In some instances, a drawback of conventional cancer treatment is that the treatment is non-specific, affecting healthy cells as well as cancer cells, resulting in toxic side effects.

MUC1 mucin is a high molecular weight glycoprotein which is expressed in normal cells as well as cancer cells. However, tumor associated mucin often carries altered patterns of glycosylation. In many cancers, MUC1 is overexpressed and/or under or aberrantly glycosylated. The aberrant glycosylation of MUC1 in cancer tissues results in exposure of core peptide epitopes to the immune system. These characteristics render tumor-associated mucins antigenically distinct from normal cell counterpart mucins. Accordingly, provided herein are immunogenic vaccine formulations that induce a cellular and/or humoral immune response targeting MUC1 antigens expressed in tumors and/or cancer tissues.

In some embodiments, the immunogenic formulations described herein elicit antigen-specific B-cell and/or T-cell responses that recognize tumor-associated antigens and attack cancer cells. In some of such embodiments, cancer cells are attacked selectively, thereby reducing the potential for toxic side effects. In other embodiments, the immunogenic formulations described herein induce B-cells to produce antibodies against cancer antigens. Accordingly, an immunotherapy approach comprising the use of liposomal vaccine formulations described herein has the potential to augment the efficacy of existing cancer therapies. In some embodiments, administration of the liposomal vaccine formulations provided herein increases life span and/or improves the quality of life of individuals undergoing treatment with the vaccines described herein.

MUC1 Mucins

Mucins are glycoproteins characterized by high molecular weight (>1,000,000 daltons) and extensive glycosylation (often over 80%). The human MUC1 gene product is strongly expressed on many human cancer cells including and not limited to breast, pancreatic and certain ovarian cancer cells. Although the MUC1 encoded mucins expressed on various cancers contain the same tandem repeat core peptide sequence, glycosylation differences exist. Because of underglycosylation in cancer cells, MUC1 molecules on cancer cells express epitopes which are not expressed on normal epithelial cells. MUC1 mucin consists of an integral membrane protein with extracellular, transmembrane and cytoplasmic domains. The antigenic components of MUC1 reside in the extracellular domain of MUC1 which comprises a glycoprotein consisting of tandem repeats of a 20-mer amino acid unit of SEQ ID NO: 1 as described below.

The amino acid sequence of Human MUC1 is available in the SWISS-PROT database as P15941. The number of repeats is highly polymorphic. It varies from 21 to 125 in the northern European population. The most frequent alleles contains 41 and 85 repeats. For Mouse MUC1, see SWISS-PROT Q02496.

MUC1 is a polymorphic antigen characterized by a variable number of perfect and imperfect repeats of the following core 20-mer sequence:

```
                                           (SEQ ID NO: 1)
1 2 3 4 5 6 7 8 9 10  11 12 13 14 15 16 17 18 19 20
T S A P D T R P A P    G  S  T  A  P  P  A  H  G  V
```

The tandemly repeated icosapeptide underlies polymorphism at three positions, as shown by brackets: TSAP[D/E][T/S]RPAPGSTAP[P/A/Q/T]AHGV (SEQ ID NO: 3). The common polymorphisms are the coordinated double mutation DT->ES and the single replacements P->A, P->Q and P->T. The most frequent replacement DT>ES occurs in up to 50% of the repeats.

Contemplated within the scope of embodiments presented herein are vaccines comprising glycolipopeptides which comprise at least one native B and/or T cell epitope of MUC1, or at least one mutant epitope substantially identical to such a native epitope. In some embodiments, the glycopeptides optionally comprise additional MUC1 sequences which are not part of an epitope.

In some embodiments, a glycopeptide suitable for a liposomal vaccine formulation described herein comprises a B cell epitope or a T cell epitope of MUC1 (which, in each case, may be a natural epitope or an allowed mutant thereof), or a combination thereof. In some embodiments, these epitopes are identical, overlapping, or distinct. In some embodiments, T and B cell epitopes of an antigen overlap. For example, in the case of MUC1, SAPDTRP, SEQ ID NO: 4 (i.e., amino acids 2-8 of SEQ ID NO:1) is a T-cell epitope, while PDTRP, SEQ ID NO: 5 (i.e., amino acids 4-8 of SEQ ID NO:1) is a B-cell epitope.

The glycosylation sites on an immunogen present in a vaccine formulation described herein are optionally one or more of (1) sites actually glycosylated in the MUC1-derived tumor glycoprotein, (2) sites that are glycosylatable but not actually glycosylated in that tumor glycoprotein, and/or (3) sites foreign to a tumor glycoprotein. None, one, some or all of the glycosylation sites normally glycosylated in the MUC1-derived tumor glycoprotein are glycosylated in an immunogen present in a vaccine formulation provided herein.

Immunogens suitable for vaccine formulations described herein comprise two or more copies of the aforementioned complete repeat sequences or a linear permutation thereof.

Each MUC1 epitope in question optionally corresponds to one or more epitopes of the variable tandem repeat region, or to an epitope outside that region. Epitopes in the tandem repeat region include, for example, RPAPGS SEQ ID NO: 6 (i.e., amino acids 7-12 of SEQ ID NO:1), PPAHGVT, SEQ ID NO: 7 (i.e., amino acids 15-20, and 1 of SEQ ID NO:1) and PDTRP, SEQ IF NO; 8 (i.e., amino acids 4-8 of SEQ ID NO:1). The sequence PDTRPAPGS SEQ ID NO:9 (i.e., amino acids 4-12 of SEQ ID NO:1) includes two overlapping epitopes. The PDTRP sequence SEQ ID NO: 10, forms the tip of a protruding knob exposed to solvents and forming a stable type II beta-turn.

Also contemplated within the scope of embodiments presented herein are glycolipopeptides comprising at least one 20 amino acid sequence (a core tandem repeat) which differs solely by one or more conservative substitutions and/or a single nonconservative substitution from a tandem repeat of MUC1, and comprises an epitope of the variable tandem repeat region of MUC1 (either identically, or an allowed mutant).

In a subset of these embodiments, the glycolipopeptide comprises a plurality of nonoverlapping core tandem repeats, such as two (for a total of 40 amino acids), three (for a total of 60 amino acids), four, five, six, seven or eight. These core tandem repeats may, but need not be, identical to each other. In contrast, the natural human MUC1 mucin, the number of repeats is typically 21-125.

Also contemplated within the scope of embodiments presented herein are vaccine formulations wherein the peptide portion of the glycolipopeptide optionally comprises additional amino acid subsequences. Such subsequences comprise additional epitopes, including MUC1 variable tandem repeat region epitopes (falling short of a core tandem repeat), MUC1 epitopes from outside that region, or epitopes of other cancer antigens.

Accordingly, provided herein are vaccine formulations comprising MUC1 glycolipopeptides. In some embodiments, such synthetic MUC1 glycolipopeptides comprise one or more copies of a core tandem repeating peptide of SEQ ID NO: 1 that mimic MUC1 peptide epitopes present on cancer cells. Provided herein, in some embodiments, are MUC1 glycolipopeptides comprising a peptide comprising at least two copies of a core tandem repeat:

```
                                           (SEQ ID NO: 1)
                  TSAPDTRPAPGSTAPPAHGV
``` or a sequence substantially identical to SEQ ID NO: 1, or linear permutation thereof;
wherein
S and T are independently, at each occurrence, optionally substituted with a cancer-associated carbohydrate epitope Te.

Since there are multiple repeats of this sequence, the starting point shown is arbitrary, and the "linear permutations" for the tandem repeats vary. For example, in one embodiment, a tandem repeating unit starts at amino acid 19 of SEQ ID NO: 1 and cycles through the entire peptide sequence of SEQ ID NO: 1 to provide a core tandem repeat of sequence GVTSAPDTRPAPGSTAPPAH (SEQ ID NO: 11). In another exemplary embodiment, a tandem repeating unit merely starts at amino acid 6 of SEQ ID NO: 1 and cycles through the entire peptide sequence of SEQ ID NO: 1 to provide a core tandem repeat of sequence TRPAPGSTAPPAHGVTSAPD (SEQ ID NO: 12). Other analogous "linear permutations" are also contemplated as being within the scope of embodiments presented herein.

In some embodiments, a liposomal formulation described herein comprises between 1 and 30 copies of a core tandem repeat of SEQ ID NO: 1 or a sequence substantially identical to SEQ ID NO: 1, or linear permutation thereof. In some embodiments, a liposomal formulation described herein comprises between 1 and 20 copies of a core tandem repeat of SEQ ID NO: 1, a sequence substantially identical to SEQ ID NO: 1, or linear permutation thereof. In some embodiments, a liposomal formulation described herein comprises between 1 and 10 copies of a core tandem repeat of SEQ ID NO 1, a sequence substantially identical to SEQ ID NO: 1, or linear permutation thereof. In some embodiments, a liposomal formulation described herein comprises between 1 and 5 copies of a core tandem repeat of SEQ ID NO: 1, a sequence substantially identical to SEQ ID NO: 1, or linear permutation thereof. In some embodiments, a liposomal formulation described herein comprises 2 copies of a core tandem repeat of SEQ ID NO: 1, a sequence substantially identical to SEQ ID NO: 1, or linear permutation thereof. In some embodiments, a liposomal formulation described herein comprises 3 copies of a core tandem repeat of SEQ ID NO: 1, a sequence substantially identical to SEQ ID NO: 1, or linear permutation thereof. In some embodiments, a liposomal formulation described herein comprises 4 copies of a core tandem repeat of SEQ ID NO: 1, a sequence substantially identical to SEQ ID NO: 1, or linear permutation thereof. In some embodiments, a liposomal formulation described herein comprises 5 copies of a core tandem repeat of SEQ ID NO: 1, a sequence substantially identical to SEQ ID NO: 1, or linear permutation thereof. In some embodiments, a liposomal formulation described herein comprises 6 copies of a core tandem repeat of SEQ ID NO: 1, a sequence substantially identical to SEQ ID NO: 1, or linear permutation thereof. In some embodiments, a liposomal formulation described herein comprises 7 copies of a core tandem repeat of SEQ ID NO: 1, a sequence substantially identical to SEQ ID NO: 1, or linear permutation thereof. In some embodiments, a liposomal formulation described herein comprises 8 copies of a core tandem repeat of SEQ ID NO: 1, a sequence substantially identical to SEQ ID NO: 1, or linear permutation thereof. In some embodiments, a liposomal formulation described herein comprises 9 copies of a core tandem repeat of SEQ ID NO: 1, a sequence substantially identical to SEQ ID NO: 1, or linear permutation thereof. In some embodiments, a liposomal formulation described herein comprises 10 copies of a core tandem repeat of SEQ ID NO: 1, a sequence substantially identical to SEQ ID NO: 1, or linear permutation thereof. In any of the above embodiments, the one or more copies of a core tandem repeat of SEQ ID NO: 1 is glycosylated as described herein.

As used herein, "sequence substantially identical to SEQ ID NO: 1" means that, in one embodiment, a sequence is at least 80% identical to SEQ ID NO: 1. In other embodiments, "sequence substantially identical to SEQ ID NO: 1" means that, a sequence is at least 85% identical to SEQ ID NO: 1. In other embodiments, "sequence substantially identical to SEQ ID NO: 1" means that, a sequence is at least 90% identical to SEQ ID NO: 1. In other embodiments, "sequence substantially identical to SEQ ID NO: 1" means that, a sequence is at least 95% identical to SEQ ID NO: 1.

MUC1 Core Repeat Variants

In some embodiments, the vaccine formulation described herein incorporate immunologically active homologues or variants of MUC1 core repeats (e.g., variants of SEQ ID NO: 1). Accordingly, the embodiments presented herein encompass the use of a MUC1 core repeat peptide having a sequence that is similar to, but not identical to, the amino acid sequence depicted in SEQ ID NO: 1. Thus, also contemplated within the scope of embodiments provided herein is the use of a MUC1 core repeat that has a sequence identity of 99%, 98%, 97%, 96%, 95%, 94%, 93%, 92%, 91%, 90%, 89%, 88%, 87%, 86%, 85%, 84%, 83%, 82%, 81%, or 80% compared to the sequence of SEQ ID NO. 1, and which is immunologically active.

In some embodiments, a MUC1 core repeat protein is optionally modified to contain conservative variations so as to change non-critical residues or residues in non-critical regions. Amino acids that are not critical are identified by methods known in the art, such as site-directed mutagenesis, crystallization, nuclear magnetic resonance, photoaffinity labeling, or alanine-scanning mutagenesis (Cunningham et al., Science, 244:1081-1085 (1989); Smith et al., J. Mol. Biol., 224:899-904 (1992); de Vos et al., Science, 255:306-312 (1992)). Modified proteins are tested for activity or ability to induce an immune response via methods such as protease binding to substrate, cleavage, in vitro activity, or in vivo activity.

In some embodiments, a MUC1 core repeat variant incorporates 1, 2, 3, 4, or 5 amino acid substitutions that improve MUC1 core repeat stability or with a different hydrophobic amino acid that improves MUC1 core repeat stability against oxidation, or with a different amino acid that improves MUC1 core repeat stability against protease. Thus, a "variant" MUC1 core repeat polypeptide differs in amino acid sequence from the sequence represented in SEQ ID NO: 1 by one or more substitutions, deletions, insertions, inversions, truncations, modifications, or a combination thereof. Such a variant optionally contains amino acid substitutions that substitute a given amino acid with another amino acid of similar characteristics. Conservative substitutions include, among the aliphatic amino acids, interchange of alanine, valine, leucine, and isoleucine; interchange of the hydroxyl residues serine and threonine, exchange of the acidic residues aspartate and glutamate, substitution between the amide residues asparagine and glutamine, exchange of the basic residues lysine and arginine, and replacements among the aromatic residues phenylalanine and tyrosine. See Bowie et al., Science, 247:1306-1310 (1990).

The core tandem repeat region is optionally modified, as described in detail below, in ways in which the variant retains the characteristic of T-cell activation.

In some embodiments, a MUC1 variant is a fragment of the MUC1 protein. In some embodiments, MUC1 variants include proteolytic cleavage-resistant MUC1 fragments or MUC1 fragments containing one or more non-natural amino acids, such as D-amino acids. Such derivatives would have the benefit of increased circulating half-life, while retaining the beneficial T-cell specificity.

In another embodiment, a MUC1 variant includes a portion of the extracellular tandem repeat region of MUC1, with the amino acid sequence DTR, SEQ ID NO: 13, (Asp-Thr-Arg), DTRP, SEQ ID NO: 14, (Asp-Thr-Arg-Pro), SAPDTRP, SEQ ID NO: 15, (Ser-Ala-Pro-Asp-Thr-Arg-Pro), or TSAP-DTRPA, SEQ ID NO: 16. Other MUC1 derivatives consist essentially of one truncated peptide core repeat of the MUC1 mucin, for example, GVTSAPDTRPAPGSTA, SEQ ID NO: 17. Of course this truncated core sequence is permuted and/or otherwise altered as described above.

MUC1 Core Repeat Modifications

MUC1 core repeat variants encompass derivatives or analogs in which (i) an amino acid is substituted with an amino acid residue that is not one encoded by the genetic code, (ii) the mature polypeptide is fused with another compound such as polyethylene glycol, or (iii) additional amino acids are fused to the MUC1 polypeptide, such as a leader or secretory sequence or a sequence for purification of the polypeptide.

Typical modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Modifications are made anywhere in a MUC1 core repeat polypeptide, including the peptide backbone, the amino acid side-chains, and the amino or carboxyl termini. Certain common peptide modifications that are useful for modification of MUC1 core repeat include glycosylation, lipid attachment, sulfation, gamma-carboxylation of glutamic acid residues, hydroxylation, blockage of the amino or carboxyl group in a polypeptide, or both, by a covalent modification, and ADP-ribosylation.

Moreover, one or more amino acids of the core sequence is altered, in a conservative manner such that the requisite T-cell-activating activity is maintained. Typical substitutions are made among the following groups of amino acids: (a) G, A, V, L and I; (b) G and P; (c) S, C, T, M; (d) F, Y, and W; (e) H, K and R; and (f) D, E, N, and Q. Other substitutions include the following groups: (i) S and T; (ii) P and G; a (iii) A, V, L and I.

Also contemplated within the scope of embodiments provided herein are modifications of the core repeat polypeptide wherein the polypeptide is joined to another polypeptide with which it is not normally associated (e.g., Glutathione S-transferase (GST)-fusion protein, beta-galactosidase fusions, yeast two-hybrid GAL fusions, poly-His fusions, Ig fusions and the like). Thus, a MUC1 core repeat peptide is optionally operatively linked, at either its N-terminus or C-terminus, to a heterologous polypeptide having an amino acid sequence not substantially homologous to the MUC1 core repeat. "Operatively linked" indicates that the MUC1 core repeat peptide and the heterologous polypeptide are both in-frame. Such a fusion protein alters (e.g., enhances, dampens) the ability of the MUC1 core repeat, or a functional variant thereof, to induce an immunological reaction from a host system.

Carbohydrate Epitopes

Human cancers present several carbohydrate epitopes. These include the lacto series type 1 and type 2 chains, cancer associated ganglio chains, and neutral glycosphingolipids. Examples of the lacto series Type 1 and Type 2 chains include and are not limited to: Lewis a, dimeric Lewis a, Lewis b, Lewis b/Lewis a, Lewis x, Lewis, y, Lewis a/Lewis x. dimeric Lewis x, Lewis y/Lewis x, trifucosyl Lewis y, trifucosyl Lewis b, sialosyl Lewis x, sialosyl Lewis y, sialosyl dimeric Lewis x, Tn, sialosyl Tn, sialosyl TF, TF and the like. Examples of cancer-associated ganglio chains include and are not limited to GM3. GD3, GM2, GM4, GD2, GM1, GD-1a, GD-1b and the like. Neutral sphingolipids include globotriose, globotetraose, globopentaose, isoglobotriose, isoglobotetraose, mucotriose, mucotetraose, lactotriose, lactotetraose, neolactotetraose, gangliotriose, gangliotetraose, galabiose, 9-O-acetyl-GD3 and the like.

Another group of such antigens comprises the tumor-associated glycosylated mucins. Generally, mucins are glycoproteins found in saliva, gastric juices, etc., that form viscous solutions and act as lubricants or protectants on external and internal surfaces of the body. Cancerous tissues produce aberrant mucins which are relatively less glycosylated and/or overexpressed than their normal counterparts. Due to functional alterations of the protein glycosylation machinery in cancer cells, tumor-associated mucins typically contain short, incomplete glycans. Thus, by way of example, normal mucin associated with human milk fat globules consists primarily of the tetrasaccharide glycan, gal β 1-4 glcNAcp1-6(gal β 1-3) gal NAc-α and its sialylated analogs. But the tumor-associated Tn hapten consists only of the monosaccharide residue, α-2-acetamido-3-deoxy-D-galactopyranosyl, and the T-hapten consists only of the disaccharide β-D-galactopyranosyl-(1-3)-α-acetamido-2-deoxy-D-galactopyranos-yl. Other haptens of tumor-associated mucins, such as the sialyl-Tn and the sialyl-(2-6)T haptens, include haptens from the attachment of terminal sialyl residues to the short Tn and T glycans.

The T and Tn antigens are found in immunoreactive form on the external surface membranes of most primary carcinoma cells and their metastases (>90% of all human carcinomas). As cancer markers, T and Tn permit early immunohistochemical detection and prognostication of the invasiveness of certain carcinomas. The extent of expression of T and Tn often correlates with the degree of differentiation of cancers including certain carcinomas.

A variety of carbohydrates are suitable for incorporation into a synthetic glycolipopeptide immunogen present in a liposomal vaccine formulation described herein. Various carbohydrate epitopes are described in Wong, U.S. Pat. No. 6,013,779, which is incorporated herein by reference for such disclosure. The Tn, T, TF, sialyl Tn and sialyl (2->6)T haptens are examples of tumor-associated carbohydrate epitopes which are highly expressed in common human cancers; such carbohydrate epitopes are conjugated to aminated compounds and/or amino acids using suitable methods.

In some embodiments, carbohydrate epitopes suitable for glycosylation of a core tandem repeat of SEQ ID NO: 1 include and are not limited to:

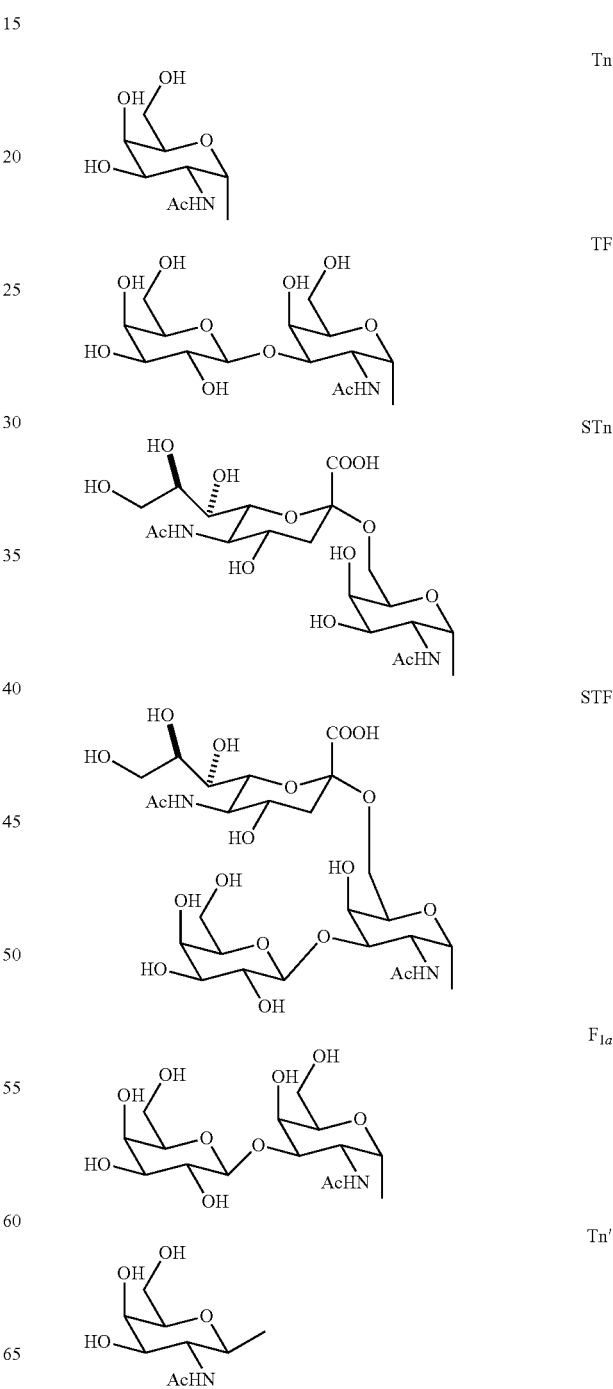

the T-hapten, and the like.

In natural human 20-mer MUC1 mucin, there are five typical O-linked glycosylation sites per repeat. In normal MUC1, an average of 2.6 of these five sites is occupied. Contemplated within the scope of embodiments presented herein are vaccine formulations comprising MUC1 glycoproteins wherein the average number of glycosylated amino acids per repeat is less than, the same as, or greater than the "natural" value. In some of such embodiments, one or more of the Serine or Threonine residues of SEQ ID NO: 1 are O-glycosylated.

As used herein, a glycosylated amino acid or peptide is one whose side chain comprises at least one carbohydrate monomeric unit. Optionally, a glycosylated amino acid or peptide incorporates an aliphatic and/or aromatic moiety. A simply glycosylated amino acid or peptide is one whose side chain consists of a linker selected from the group consisting of —O—, —S—, and one or more carbohydrate units. A glycosylated amino acid or peptide comprises monomer units selected from galactose, mannose, glucose, N-acetylglucosamine, N-acetylgalactosamine, sialic acids, fucose, xylose and the like. The number of sugar units varies, from about 1 to 20; or 1 to 10, or 1 to 5, or 1-3 or 1-2. If an oligosaccharide chain (i.e., a chain of two or more sugar units) is attached, the chain is linear or branched.

In one embodiment, a glycosylated amino acid or peptide comprises —O-glycosylated and —N-glycosylated residues. O-glycosylation is e.g., of hydroxy-containing amino acids such as serine or threonine. Tyrosine, hydroxylysine, and hydroxyproline are also optionally O-glycosylated. In other embodiments, a glycosylated amino acid or peptide comprises N-glycosylated residues. N-glycosylation is e.g., of amide-containing amino acid side chains, such as Asn, or of the amino terminal of a protein. In an N-glycosylated linkage, the nitrogen is optionally unsubstituted (—NH—) or substituted (—NZ—). In other embodiments, a glycosylated amino acid or peptide comprises S-glycosylated residues. S-glycosylation is e.g., of the thiol group of cysteine.

Accordingly, in some embodiments, the vaccine formulations described herein comprise immunogens wherein one of the Serine or Threonine residues of SEQ ID NO: 1 is glycosylated. In some embodiments, the vaccine formulations described herein comprise immunogens wherein two of the Serine or Threonine residues of SEQ ID NO: 1 is glycosylated. In some embodiments, the vaccine formulations described herein comprise immunogens wherein three of the Serine or Threonine residues of SEQ ID NO: 1 is glycosylated. In some embodiments, the vaccine formulations described herein comprise immunogens wherein four of the Serine or Threonine residues of SEQ ID NO: 1 is glycosylated. In some embodiments, the vaccine formulations described herein comprise immunogens wherein five of the Serine or Threonine residues of SEQ ID NO: 1 is glycosylated.

In some embodiments, the vaccine formulations described herein comprise two or more copies of the core tandem repeat sequence of SEQ ID NO: 1. In some of such embodiments, the vaccine formulations described herein comprise immunogens having two or more copies of the core tandem repeat sequence of SEQ ID NO: 1 wherein one of the Serine or Threonine residues of SEQ ID NO: 1 is glycosylated. In some embodiments, the vaccine formulations described herein comprise immunogens having two or more copies of the core tandem repeat sequence of SEQ ID NO: 1 wherein two of the Serine or Threonine residues of SEQ ID NO: 1 is glycosylated. In some embodiments, the vaccine formulations described herein comprise immunogens having two or more copies of the core tandem repeat sequence of SEQ ID NO: 1 wherein three of the Serine or Threonine residues of SEQ ID NO: 1 is glycosylated. In some embodiments, the vaccine formulations described herein comprise immunogens having two or more copies of the core tandem repeat sequence of SEQ ID NO: 1 wherein four of the Serine or Threonine residues of SEQ ID NO: 1 is glycosylated. In some embodiments, the vaccine formulations described herein comprise immunogens having two or more copies of the core tandem repeat sequence of SEQ ID NO: 1 wherein five of the Serine or Threonine residues of SEQ ID NO: 1 is glycosylated. In some embodiments, the vaccine formulations described herein comprise immunogens having two or more copies of the core tandem repeat sequence of SEQ ID NO: 1 wherein six of the Serine or Threonine residues of SEQ ID NO: 1 is glycosylated. In some embodiments, the vaccine formulations described herein comprise immunogens having two or more copies of the core tandem repeat sequence of SEQ ID NO: 1 wherein seven of the Serine or Threonine residues of SEQ ID NO: 1 is glycosylated. In some embodiments, the vaccine formulations described herein comprise immunogens having two or more copies of the core tandem repeat sequence of SEQ ID NO: 1 wherein eight of the Serine or Threonine residues of SEQ ID NO: 1 is glycosylated. In some embodiments, the vaccine formulations described herein comprise immunogens having two or more copies of the core tandem repeat sequence of SEQ ID NO: 1 wherein nine of the Serine or Threonine residues of SEQ ID NO: 1 is glycosylated. In some embodiments, the vaccine formulations described herein comprise immunogens having two or more copies of the core tandem repeat sequence of SEQ ID NO: 1 wherein ten of the Serine or Threonine residues of SEQ ID NO: 1 is glycosylated. Depending on the number of copies of the core tandem repeat sequence of SEQ ID NO: 1, additional Serine or Threonine residues are optionally glycosylated and are contemplated as being within the scope of embodiments presented herein.

In some embodiments for immunogens having two or more copies of the core tandem repeat sequence of SEQ ID NO: 1, the glycosylation pattern of a given core tandem repeat sequence of SEQ ID NO: 1 is the same for each residue in the other core tandem repeat(s). For example, in an immunogen having a core tandem repeat having glycosylation on two Threonine residues and one Serine residue, the other core tandem repeat(s) would have the same glycosylation on the corresponding residues, i.e., two Threonine residues and one Serine residue.

In some embodiments for immunogens having two or more copies of the core tandem repeat sequence of SEQ ID NO: 1, the glycosylation pattern of a core tandem repeat sequence of SEQ ID NO: 1 is not the same for each residue in the other core tandem repeat(s). That is, a core tandem repeat is glycosylated differently than the other core tandem repeat(s) in some embodiments. It is contemplated that these differences include different glycosylation occurrences (e.g., 4 glycosylations on a first core tandem repeat and 2 glycosylations on a second core tandem repeat), different amino acid residues for glycosylation and different glycosyl groups between core tandem repeats.

In any of the above embodiments, each glycosyl residue present on a core tandem repeat sequence of SEQ ID NO: 1, or SEQ ID NO: 18, or SEQ ID NO: 19, or any other peptide sequence described herein is independently selected at each occurrence. Accordingly, a glycosylated peptide in a vaccine formulation described herein comprises one or more carbohydrate epitopes (e.g., glycosyl residues described herein such as cancer-associated Tc carbohydrate epitopes) that are all same, or different, or any combination of various glycosyl residues (e.g., Tc residues).

In some embodiments, the vaccine formulations described herein comprise immunogens having two or more copies of the core tandem repeat sequence of SEQ ID NO: 1 wherein Threonine-6, Serine-12 and Threonine-13 are glycosylated for each core tandem repeat. In some embodiments, the vaccine formulations described herein comprise immunogens having two or more copies of the core tandem repeat sequence of SEQ ID NO: 1 which do not have Serine-12 and Threonine-13 glycosylated for a first core tandem repeat and Threonine-6 glycosylated for a second or additional core tandem repeat.

Lipids

In some embodiments, a core tandem repeat of SEQ ID NO: 1 is covalently attached to one or more lipidated amino acids. As used herein, a "lipid" is a palmitoyl, lauryl, myristoyl, stearoyl or decanoyl group or, more generally, any $C_2$-$C_{30}$ saturated, monounsaturated or polyunsaturated, branched or straight chain fatty acyl group that is attached to amino acids that possess functional oxygen, nitrogen, or sulfur groups. Such amino acids include, but are not limited to, threonine, serine, lysine, arginine, and cysteine.

A "monolipopeptide" is a peptide to which only one lipid is attached. Similarly, a "dilipopeptide" is a peptide that has two lipids attached to either one or two amino acids. If the two lipids are attached to two amino acid residues, those residues are spaced any number of amino acids apart. In cases where more than one lipid is attached, the lipids are either the same lipid or are different lipids. Similarly, if more than two lipids are attached, two or more of the lipids are the same or all of the lipids are dissimilar.

Accordingly, the lipidated peptides provided herein are incorporated into a liposome because the lipid portion of that peptide spontaneously integrates into the lipid bilayer of a liposome. Thus, in one embodiment, a lipopeptide is presented on the "surface" of a liposome. In an alternate embodiment, a peptide is encapsulated within a liposome.

A glycolipopeptide comprises one or more glycosylated amino acids wherein at least one of the glycosylated amino acids comprises a disease-associated carbohydrate epitope, such as a tumor-associated carbohydrate epitope, and one or more lipidated amino acids.

In some embodiments, a glycolipopeptide present in a liposomal vaccine formulation described herein is a glycosylated dilipopeptide. In some of such embodiments, the dilipopeptide attached to a glycosylated core tandem repeat of SEQ ID NO: 1 comprises the sequence

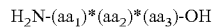

$$H_2N\text{-}(aa_1)^*(aa_2)^*(aa_3)\text{-}OH$$

wherein
aa₁ is independently, at each occurrence, selected from S, T, K, R or C;
aa₂ is independently, at each occurrence, selected from S, T, K, R or C;
aa₃ is independently, at each occurrence, selected from L or G;
* independently, at each occurrence, represents a lipid covalently attached to an amino acid residue.

As used herein, the lipid represented by "*" is covalently attached to the amino acid preceding the "*". Thus K*C*L represents a dilipidated sequence wherein the K and C residues are covalently attached to a lipid. Examples of dilipidated sequences include and are not limited to S*S*L, S*S*G, S*K*L, T*S*L, R*S*L, C*T*G and the like. Other analogous permutations are also contemplated as being within the scope of embodiments presented herein.

In some of such embodiments, the dilipidated sequence is attached to the N terminal of a core tandem repeat of SEQ ID NO: 1. In some other such embodiments, the dilipidated sequence is attached to the C terminal of a core tandem repeat of SEQ ID NO: 1.

In some embodiments, a glycolipopeptide present in a liposomal vaccine formulation described herein comprises, at its C-terminal region, the sequence SSL, where both serines are lipidated.

Accordingly, provided herein are vaccine formulations comprising MUC1 glycolipopeptides. In some embodiments, such synthetic MUC1 glycolipopeptides comprise one or more copies of a core tandem repeating peptide of SEQ ID NO: 1 that mimic MUC1 peptide epitopes present on cancer cells.

Provided herein, in some embodiments, are MUC1 glycolipopeptides comprising a peptide comprising at least two copies of a core tandem repeat:

(SEQ ID NO: 1)
TSAPDTRPAPGSTAPPAHGV or a sequence at least 85% identical to SEQ ID No: 1, or linear permutation thereof;
wherein
S and T are independently, at each occurrence, optionally substituted with a cancer-associated carbohydrate epitope Tc; and
a lipopeptide covalently attached to (a) having the formula:

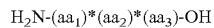

$$H_2N\text{-}(aa_1)^*(aa_2)^*(aa_3)\text{-}OH$$

wherein
aa₁ is independently, at each occurrence, selected from S, T, K, R or C;
aa₂ is independently, at each occurrence, selected from S, T, K, R or C;
aa₃ is independently, at each occurrence, selected from L or G;

* independently, at each occurrence, represents a lipid covalently attached to an amino acid residue.

Provided herein, in some embodiments, are MUC1 glycolipopeptides comprising:
(a) a peptide comprising at least two copies of a core tandem repeat:

```
                                            SEQ ID NO: 18
T(Te)S(Te)APDT(Te)RPAPGS(Te)T(Te)APPAHGV,
``` or a sequence at least 85% identical to SEQ ID NO: 18, or linear permutations thereof;
wherein
Te represents a cancer-associated carbohydrate epitope;
(b) a lipopeptide covalently attached to (a) having the formula:

$H_2N—S*S*L-OH$ wherein
* independently, at each occurrence, represents a lipid covalently attached to a Serine residue.

Provided herein, in some embodiments, are MUC1 glycolipopeptides comprising a peptide comprising at least two copies of a core tandem repeal

```
                                  (SEQ ID NO: 19)
TSAPDT(Te)RPAPGS(Te)T(Te)APPAHGV
``` or a sequence at least 85% identical to SEQ ID No: 19, or linear permutation thereof;
wherein
Te is a cancer-associated carbohydrate epitope; and
a lipopeptide covalently attached to (a) having the formula:

$H_2N-(aa_1)*(aa_2)*(aa_3)-OH$ wherein
 aa$_1$ is independently, at each occurrence, selected from S, T, K, R or C;
 aa$_2$ is independently, at each occurrence, selected from S, T, K, R or C;
 aa$_3$ is independently, at each occurrence, selected from L or G;
 * independently, at each occurrence, represents a lipid covalently attached to an amino acid residue;

In specific embodiments, a liposomal vaccine formulation described herein is a synthetic glycolipopeptide containing 43 amino acids, with two copies of SEQ ID NO: 1, and a dilipidated tripeptide sequence attached to the C-terminus as shown below:

```
                                                              (SEQ ID NO: 2)
TSAPDT(Tn)RPAPGS(Tn)T(Tn)APPAHGVTSAPDT(Tn)RPAPGS(Tn)T(Tn)APPAHGVS*S*L-OH
``` wherein
Tn is GalNAcα1.

There are six alpha-glycosylated serine and threonine moieties as indicted by the (Tn) designations. Tn is the abbreviation for N-acetylgalactosamine (GalNAc) linked by alpha glycosidic bond (GalNAcα1). There are two C-terminal myristylserine residues designated by S* which serve to anchor the peptide in the liposomes of the drug product and enhance immune recognition. All amino acids are natural L isomers and the O-linked GalNAc modified serines and threonines are all linked by alpha glycosidic bonds. There are no cysteines present in the sequence and thus no potential for disulfide bond tertiary structure in the peptide or cross-linking between peptides.

In some embodiments, a vaccine formulation provided herein comprises a salt of SEQ ID NO: 2. Examples of such salts include and are not limited to acetate, citrate, tartarate, mesylate, besylate, tosylate, maleate, fumarate, oxalate, triflate, triethylamine, diisopropylethylamine salts and the like. Further examples of such salts include and are not limited to hydrochloride, hydrobromide, phosphate, sulfate and the like. In other embodiments, a salt of SEQ ID NO: 2 is a trifluoroacetic acid salt. In specific embodiments, a salt of SEQ ID NO: 2 is an acetate salt having the formula:

$C_{248}H_{407}N_{59}O_{90}.XC_2H_3O_2$.

Adjuvants

The glycolipopeptides comprising core tandem repeats of SEQ ID NO: 1 are optionally administered in conjunction with an adjuvant to enhance a specific response to an antigen. In one embodiment, Lipid-based adjuvants, such as Lipid A and derivatives thereof, are suitable for use with the glycolipopeptide vaccine formulations described herein. Monophosphoryl lipid A (MPLA), for example, is an adjuvant that causes increased presentation of liposomal antigen to specific T Lymphocytes. In another embodiment, a muramyl dipeptide (MDP) is also a suitable adjuvant for use in conjunction with the vaccine formulations described herein.

In a further embodiment, an adjuvant suitable for use with the liposomal vaccine formulations provided herein includes stimulatory cytokines, such as interleukin-2 (IL-2). In some embodiments, IL-2 is beneficially formulated with liposomes. In some embodiments, an adjuvant is a modulator of a toll like receptor. Examples of modulators of toll-like receptors include TLR-9 agonists and are not limited to small molecule modulators of toll-like receptors such as imiquimod. Other examples of adjuvants that are used in combination with an adjuvant of Formula I or Formula II include and are not limited to saponin, CpG ODN and the like.

Synthetic mimics of Lipid A are also contemplated for use with vaccine formulations described herein. In some of such embodiments, an adjuvant is a compound of the Formula I:

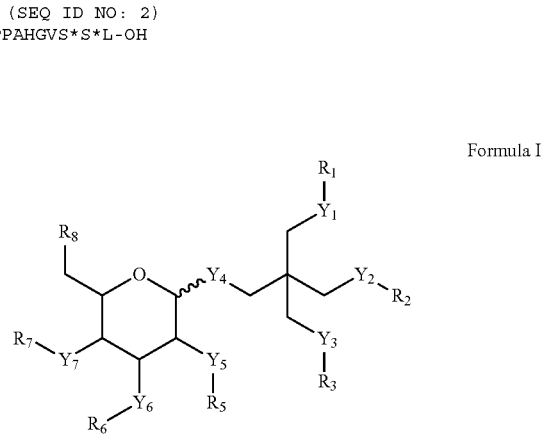

Formula I wherein at least one of $R_1$, $R_2$, $R_3$, $R_5$, $R_6$, and $R_7$ is a strongly lipophilic group selected from the group consisting of

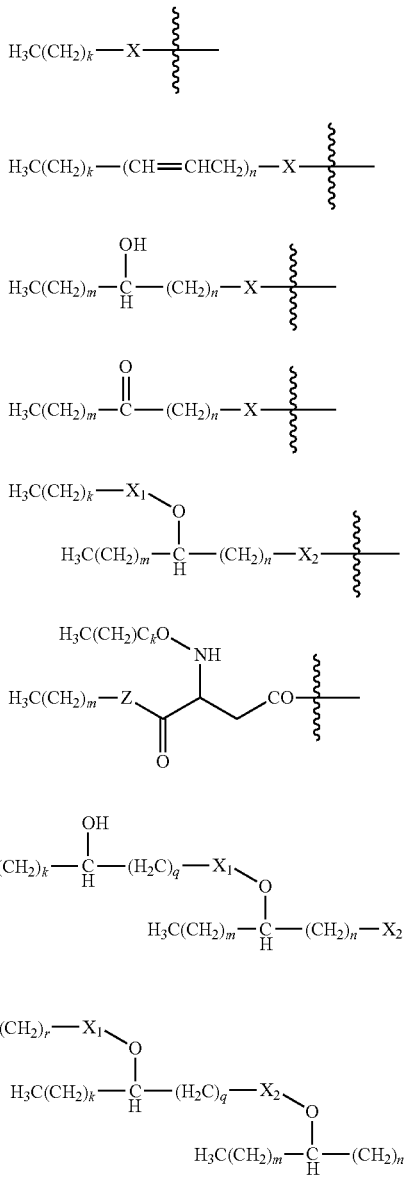

wherein X, $X_1$, $X_2$, and $X_3$ are independently —CO— or —CH$_2$—;

Z is —NH— or —O—;

k, m, and r are independently an integer of 0 to 30 inclusive, n and q are independently an integer of 0 to 6 inclusive;

wherein $Y_4$ is a spacer selected from the group consisting of —O—, —S—, and —NH— wherein, at least one of $Y_1R_1$, $Y_2R_2$, $Y_3R_3$, $Y_5R_5$, $Y_6R_6$ and $Y_7R_7$ is a monovalent phosphate equivalent (MPE), wherein each monovalent phosphate equivalent is, independently, (a) —R'—C(O)OH where R' is a substituted or unsubstituted alkyl group of 1-4 carbons, or (b) selected independently from the group consisting of —OB(OH)OR, —OP(O)(OH)OR, —OS(O)(0)(OH)OR, and —OP(=O)(OH)—O—P(=O)(OH)OR, where R is hydrogen, or a substituted or unsubstituted alkyl group of 1-4 carbons, and if R is a substituted alkyl group, the substitutions are —OH or —NH$_2$, wherein $R_8$ is selected from the group consisting of H, OH, OR$_9$, a moiety which in combination with $Y_8$ forms a monovalent phosphate equivalent as previously defined, and a group (i)-(viii) as defined above; wherein $R_9$ is an alkyl or acyl group of 1 to 10 carbon length; and wherein the glycosidic linkage is α or β;

or a compound which is a compound of Formula II:

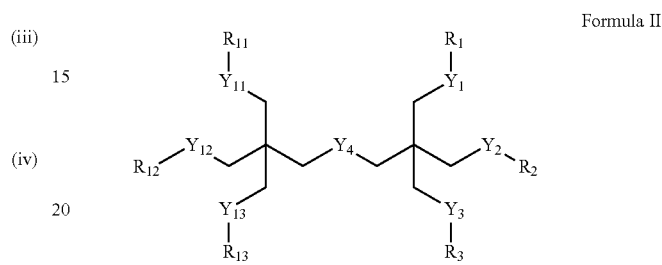

Formula II wherein at least one of $R_1$, $R_2$, $R_3$, $R_{11}$, $R_{12}$ and $R_{13}$ is a strongly lipophilic group selected from the group consisting of (i)-(viii) above;

wherein $Y_4$ is a spacer selected from the group consisting of —O—, —S—, and —NH— and wherein at least one of $Y_1R_1$, $Y_2R_2$, $Y_3R_3$, $Y_{11}R_{11}$, $Y_{12}R_{12}$ and $Y_{13}R_{13}$ is independently a monovalent phosphate equivalent as previously defined;

wherein the following limitations apply to both (I) and (II) above:

$Y_1$, $Y_2$, $Y_3$, $Y_5$, $Y_6$, $Y_7$, $Y_{11}$, $Y_{12}$ and $Y_{13}$ are spacers independently selected from the group consisting of —O—, —S—, and —NH—;

$R_1$, $R_2$, $R_3$, $R_5$, $R_6$, $R_7$, $R_{11}$, $R_{13}$ and $R_{13}$ are independently hydrogen, a moiety which with the commonly numbered Y group forms monovalent phosphate equivalent as previously defined, or a strongly lipophilic group selected from the group consisting of (i)-(viii) above.

the strongly lipophilic groups of said compound collectively provide at least two major carbon chains, and the major carbon chains of said strongly lipophilic groups collectively provide at least 30 carbon atoms;

or which compound is a pharmaceutically acceptable salt of I or II.

In some embodiments, an adjuvant suitable for a liposomal vaccine formulation described herein is a compound of Formula I, or a pharmaceutically acceptable salt thereof In some embodiments, an adjuvant suitable for a liposomal vaccine formulation described herein is a compound of Formula II, or a pharmaceutically acceptable salt thereof In some embodiments, $Y_4$ is —O—. In some embodiments, at least one strongly lipophilic group satisfies (i) and for at least one such group, k is an integer 4-30. In some embodiments, at least one strongly lipophilic group satisfies (ii), and for at least one such group, and 2k+3n is an integer 4-30. In some embodiments, at least one strongly lipophilic group satisfies (iii), and for at least one such group, and m+n+1 is 4-30. In some embodiments, at least one strongly lipophilic group satisfies (iv), and for at least one such group, m+n+1 is 4-30. In some embodiments, at least one strongly lipophilic group satisfies (v), and for at least one such group, m+n+k+1 is 4-30. In some embodiments, at least one strongly lipophilic group satisfies (vi), and for at least one such group, k+m+2 is 4-30. In some embodiments, at least one strongly lipophilic group satisfies (vii), and for at least one such group, k+q+m+n is 4-30. In some embodiments, at least one strongly lipophilic group satisfies (viii), and for at least one such group, r+k+q+m+n is 5-30.

In some embodiments, $Y_1, Y_2, Y_3, Y_4, Y_5, Y_6, Y_7, Y_{11}, Y_{12}$ and $Y_{13}$ are independently 0 or —NH—. In some embodiments, $Y_1, Y_2, Y_3, Y_4, Y_5, Y_6$ and $Y_7$, are independently consisting of —O— or —NH—. In some embodiments, $Y_1, Y_2, Y_3, Y_4, Y_{11}, Y_{12}, Y_{13}$ are independently —O— or NH—.

In some embodiments, each monophosphate equivalent is —OP(O)(OH)(OH).

In some embodiments, an adjuvant of Formula I is a compound wherein $Y_4$ is —O—;

$Y_1, Y_2$, and $Y_7$ are —O—;

$Y_3, Y_5$ and $Y_6$ are independently —O— or —NH—;

$R_1, R_3, R_5$ and $R_6$ are independently hydrogen or a strongly lipophilic group selected from (i)-(viii);

at least one of $R_1, R_3, R_5$, and $R_6$ is not hydrogen;

$R_2$ and $R_7$ are independently selected from the group consisting of H, —P(O)(OH)$_2$, —SO$_3$H, —P(O)(OH)(OCH$_2$CH$_2$NH$_2$), and —CH$_2$COOH; and $R_8$ is selected from the group consisting of H, OH, OSO$_3$H, and OR$_9$, wherein R$_9$ is an alkyl or acyl group of 1 to 10 carbon length.

In some embodiments of Formula I, $Y_4$ is —Oβ;

$Y_2$ and $Y_{12}$ are —O—;

$Y_1, Y_3, Y_{11}$, and $Y_{13}$ are independently chosen from the group consisting of —O—, —NH— and —S—;

$R_1, R_3, R_{11}$, and $R_{13}$ are independently hydrogen, or a strongly lipophilic group selected from (i)-(viii);

at least one of $R_1, R_3, R_5$, and $R_6$ is not hydrogen; and $R_2$ and $R_{12}$ are independently selected from the group consisting of H, —P(O)(OH)$_2$, —P(O)(OH)(OCH$_2$CH$_2$NH$_2$), and —CH$_2$COOH.

In some embodiments, $R_1, R_3, R_5$ and $R_6$ are independently hydrogen or a strongly lipophilic group elected from the group consisting of (i)-(viii), at least one $R_1, R_3, R_5$ and $R_6$ is not hydrogen, and $R_2$ and $R_7$ are independently selected from the group consisting of H, —P(O)(OH)$_2$, —P(O)(OH)(OCH$_2$CH$_2$NH$_2$), and —CH$_2$COOH; and R$_8$ is selected from the group consisting of H, OH, OSO$_3$H, and OR$_9$ wherein R$_9$ is an alkyl or acyl group of 1 to 10 carbon length.

In some embodiments, $R_1, R_3, R_{11}$, and $R_{13}$ are independently hydrogen, or a strongly lipophilic group selected from (i)-(viii); at least one of $R_1, R_3, R_5$, and $R_6$ is not hydrogen; and $R_2$ and $R_{12}$ are independently selected from the group consisting of —P(O)(OH)$_2$, —P(O)(OH)(OCH$_2$CH$_2$NH$_2$), and —CH$_2$COOH.

In some embodiments, each monophosphate equivalent is —OP(O)(OH)(OH).

In some embodiments, the strongly lipophilic groups of compounds described above collectively provide at least three major carbon chains, and wherein the major carbon chains of said strongly lipophilic groups collectively provide at least 40 carbon atoms, said compound having immunostimulatory activity. In some embodiments, the strongly lipophilic groups of compounds described above collectively provide at least four major carbon chains and wherein the major carbon chains collectively provide at least 50 carbon atoms, said compound having immunostimulatory activity.

In some embodiments, the strongly lipophilic groups collectively provide six major carbon chains. In some embodiments, each major carbon chain is characterized by 10, 12, 14, 16, 18 or 20 carbon atoms in said chain.

In some embodiments, $Y_3$ and $Y_5$ are —NH— and $Y_6$ is —O—. In some embodiments, $R_3, R_5$ and $R_6$ are strongly lipophilic groups according to (v), with independently chosen values for k, $X_1$, m, n, and $X_2$. In some embodiments, k and m for $R_3, R_5$ and $R_6$ are independently 8-18. In some embodiments, $X_1$ is —CO—, $X_2$ is —CO— and n=1. In some embodiments, k and m are independently 8, 10, 12, 14, 16 or 18. In some embodiments, k and m are 12. In some embodiments, $R_8$ is OH. In some embodiments, $Y_7$ is —O— and $R_7$ is —P(=O)(OH)(OH). In some embodiments, $Y_2$ is —O— and $R_2$ is H. In some embodiments, $Y_2$ is —O— and $R_2$ is —P(=O)(OH)(OH). In some embodiments, $R_1$-$R_3$ are hydrogen. In some embodiments, $Y_1$-$Y_3$ are —O— and $R_1$-$R_3$ are hydrogen. In some embodiments, $R_1$-$R_3$ are hydrogen, and two of $Y_1$-$Y_3$ are —O— and the other is —NH—. In some embodiments, two of $R_1$-$R_3$ are hydrogen. In some embodiments, two of —Y$_2$R$_2$, and —Y$_3$R$_3$ are —OH. In some embodiments, one of —Y$_1$R$_1$, —Y$_2$R$_2$, and Y$_3$R$_3$ is —OH and one of —Y$_1$R$_1$, —Y$_2$R$_2$, and Y$_3$R$_3$ is —NH$_2$.

In some embodiments, one of $R_1$-$R_4$ is hydrogen. In some embodiments, none of $R_1$-$R_3$ is hydrogen. In some embodiments, one of $R_1$-$R_3$ is a strongly lipophilic group. In some embodiments, at least two of $R_1$-$R_3$ comprise strongly lipophilic groups. In some embodiments, two of $R_1$-$R_3$ are strongly lipophilic groups. In some embodiments, three of $R_1$-$R_4$ are strongly lipophilic groups.

In some embodiments, each of spacers $Y_1$-$Y_4$ and $Y_{11}$-$Y_{13}$ is —O—. In some embodiments, three of spacers $Y_1$-$Y_4$ are —O— and the remaining spacer is —NH—.

In some embodiments, a compound of Formula I or Formula II provides one phoshate equivalent. In some embodiments, a compound of Formula I or Formula II provides two phosphate equivalents.

In some embodiments, (b) applies and R is hydroxyl. In some embodiments, (b) applies and said phosphate-equivalent comprises —OP(=O)(OH)O—. In some embodiments, (b) applies and R is a substituted or unsubstituted alkyl group of 1-4 carbons.

In some embodiments, R is CH$_2$CH$_2$NH$_2$. In some embodiments, (a) applies. In some embodiments, R' is —CH$_2$—. In some embodiments, the sugar is an amino sugar. In some embodiments, the sugar is a glucosamine.

In some embodiments, at least one phosphate equivalent is $Y_5R_5$, $Y_6R_6$, $Y_7R_7$, or $Y_8R_8$. In some embodiments, at least one phosphate equivalent is connected to said sugar unit. In some embodiments, at least one phosphate equivalent is $Y_1R_1$, $Y_2R_2$ or $Y_3R_3$. In some embodiments, at least one of $R_5$-$R_8$ comprises a strongly lipophilic group. In some embodiments, two or more of $R_5$-$R_7$ comprises a strongly lipophilic group.

In some embodiments, at least one strongly lipophilic group comprises only one major carbon chain. In some embodiments, at least one strongly lipophilic group comprises only two major carbon chains. In some embodiments, at least one strongly lipophilic group comprises only three major Carbon chains. In some embodiments, strongly lipophilic groups collectively provide three major carbon chains. In some embodiments, strongly lipophilic groups collectively provide four major carbon chains. In some embodiments, strongly lipophilic groups collectively provide five major carbon chains. In some embodiments, strongly lipophilic groups collectively provide six major carbon chains. In some embodiments, strongly lipophilic groups collectively provide seven major carbon chains. In some embodiments, strongly lipophilic groups collectively provide eight major carbon chains.

In some embodiments, each major carbon chain is 10-20 carbons. In some embodiments, each major carbon chain is 12-16 carbons. In some embodiments, the major carbon chains of the strongly lipophilic groups collectively provide at least 40 carbon atoms. In some embodiments, the major carbon chains of the strongly lipophilic groups collectively provide at least 50 carbon atoms. In some embodiments, the major carbon chains of the strongly lipophilic groups collectively provide at least 60 carbon atoms. In some embodiments, the major carbon chains of the strongly lipophilic groups collectively provide at least 70 carbon atoms. In some embodiments, the major carbon chains of the strongly lipophilic groups collectively provide at least 80 carbon atoms. In some embodiments, the major carbon chains of the strongly lipophilic groups collectively provide at least 90 carbon atoms. In some embodiments, the major carbon chains of the strongly lipophilic groups collectively provide not more than 90 carbon atoms. In some embodiments, the major carbon chains of the strongly lipophilic groups collectively provide not more than 80 carbon atoms. In some embodiments, the major carbon chains of the strongly lipophilic groups collectively provide not more than 70 carbon atoms. In some embodiments, the major carbon chains of the strongly lipophilic groups collectively provide not more than 60 carbon atoms.

In some embodiments, at least one strongly is lipophilic group is selected from the group consisting of

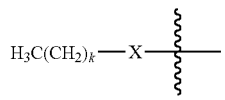
(i)

where X is —CO— or —CH$_2$—, k is an integer 4-30;

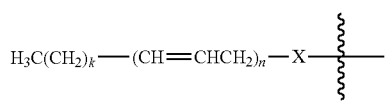
(ii)

where n is an integer 0-6, k is an integer 0-30 and 2k+3n is an integer 4-30;

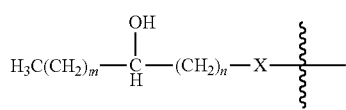
(iii)

where m and n are integers (0-6 for n and 0-30 for m), and m+n+1 is 4-30;

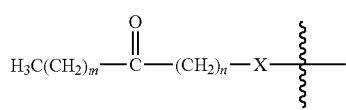
(iv)

where m+n+1 is 4-30;

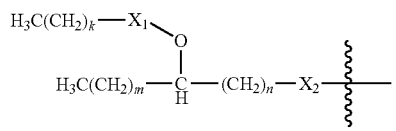
(v)

where $X_1$ and $X_2$ are independently —CO— or —CH$_2$— and m+n+k+1 is 4-30;

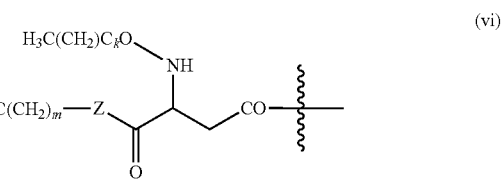
(vi)

where Z is —NH— or —O—, and k+m+2 is 4-30;

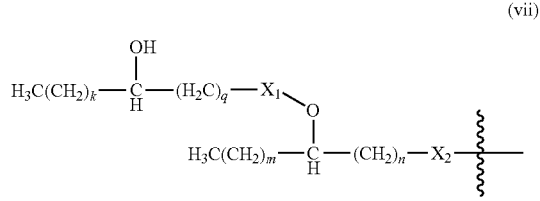
(vii)

where q is an integer 0-6, and k+q+m+n is 4-30; and

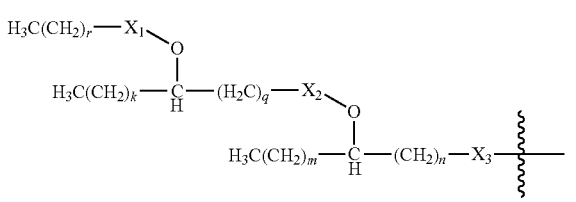
(viii)

where $X_1$, $X_2$, and $X_3$ are independently —CO— or —CH$_2$—CO$_2$—, r is an integer 0-6, and r+k+q+m+n is 5-30.

In some embodiments, all of the strongly lipophilic groups are selected from the group consisting of structures (i)-(viii). In some embodiments, at least one strongly lipophilic group is structure (i). In some embodiments, at least one strongly lipophilic group is structure (ii). In some embodiments, at least one strongly lipophilic group is structure (iii). In some embodiments, at least one strongly lipophilic group is structure (iv). In some embodiments, at least one strongly lipophilic group is structure (v). In some embodiments, at least one strongly lipophilic group is structure (vi). In some embodiments, at least one strongly lipophilic group is structure (vii). In some embodiments, at least one strongly lipophilic group is structure (viii).

In some embodiments, at least one strongly lipophilic group is one of the structures set forth below

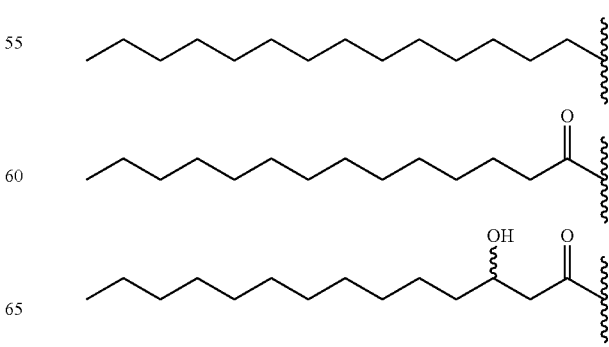

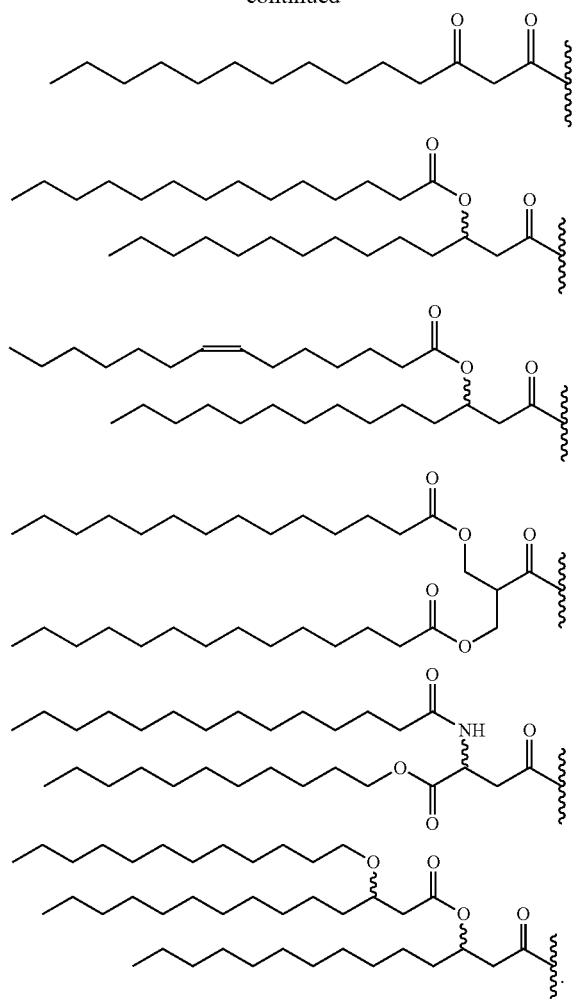
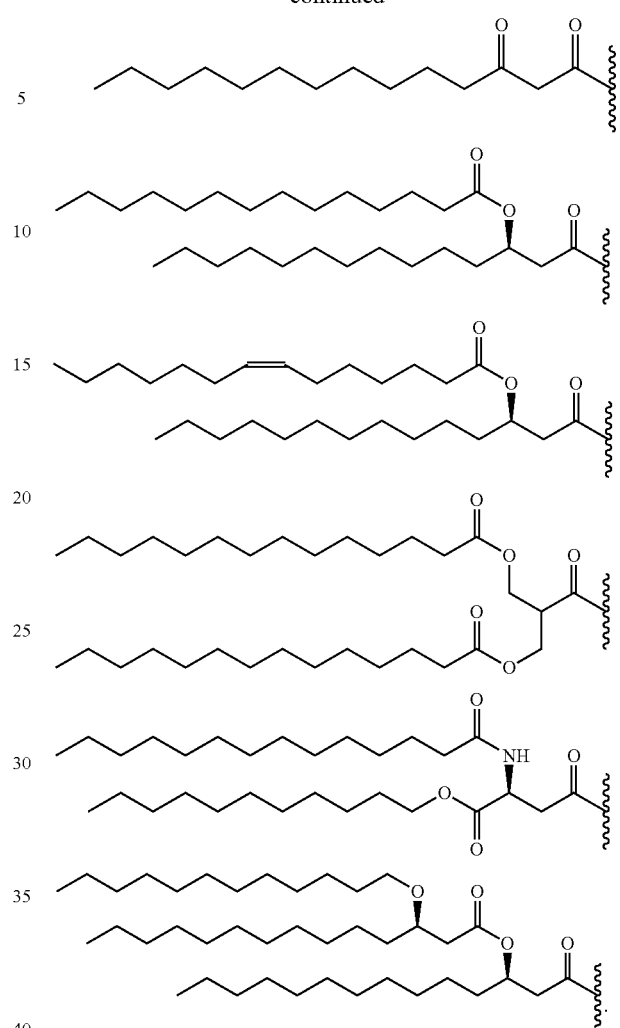

In some embodiments, the at least one strongly lipophilic group comprises an R enantiomer. In some embodiments, the at least one strongly lipophilic group comprises an S enantiomer. In some embodiments, the at least one strongly lipophilic group is a racemate. In some embodiments, the at least one strongly lipophilic group comprises an RR, an RS, and SR or an SS diastereomer. All racemates, enantiomers or diastereomers are contemplated as being within the scope of embodiments presented herein. In some embodiments, the at least one strongly lipophilic group is one of the structures set forth below:

In some embodiments, the at least one strongly lipophilic group is one of the structures set forth below:

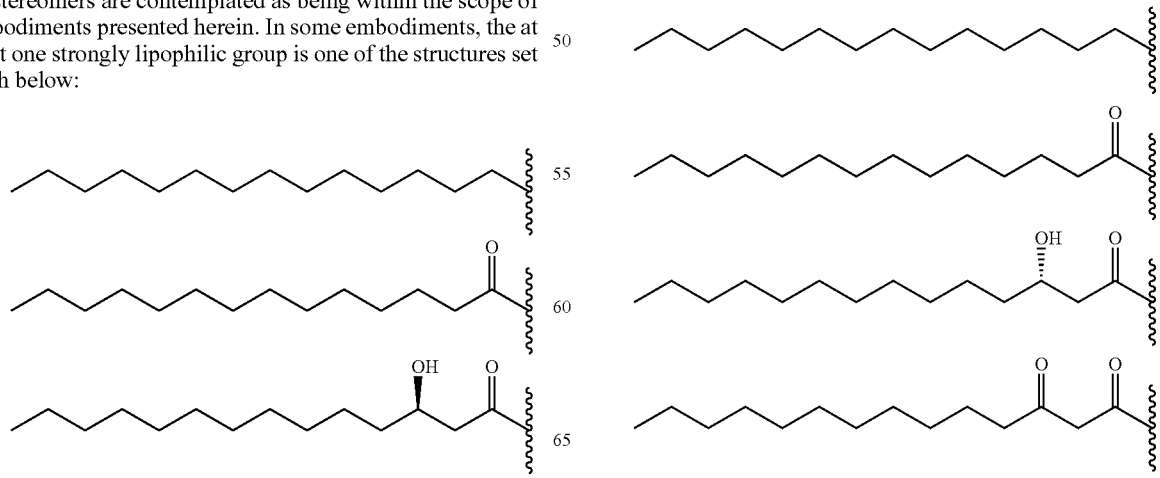

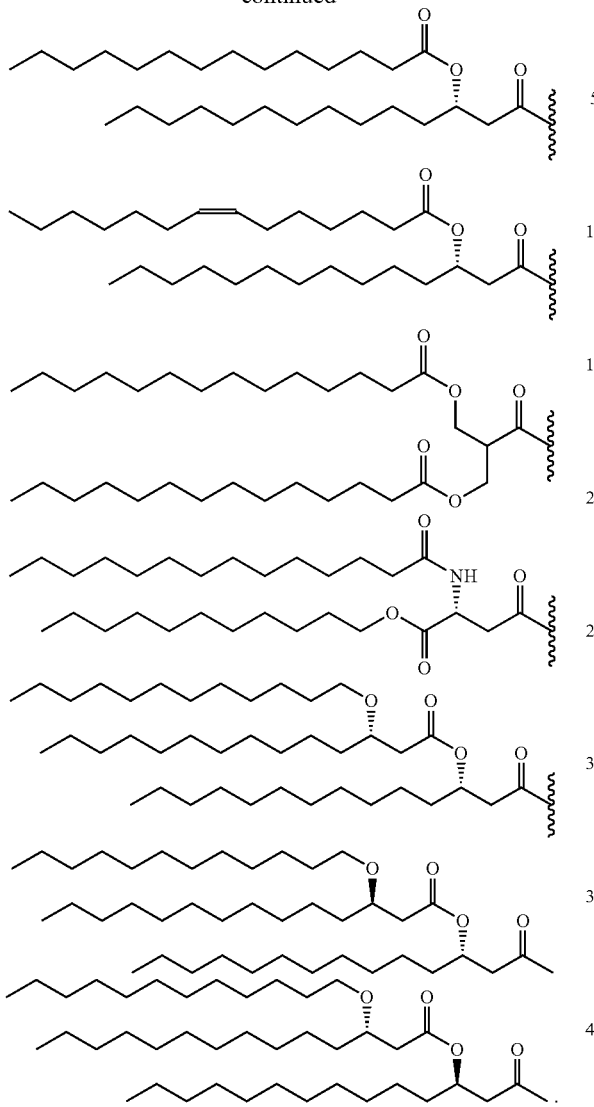

In some embodiments, each strongly lipophilic group is independently one of the structures set forth above.

In some embodiments, the adjuvant is a compound as defined below:

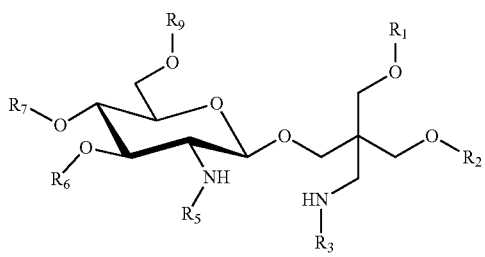

wherein $R_1$, $R_3$, $R_5$ and $R_6$ are independently hydrogen or a lipophilic group selected from the group consisting of (i)

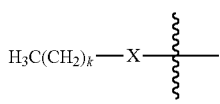

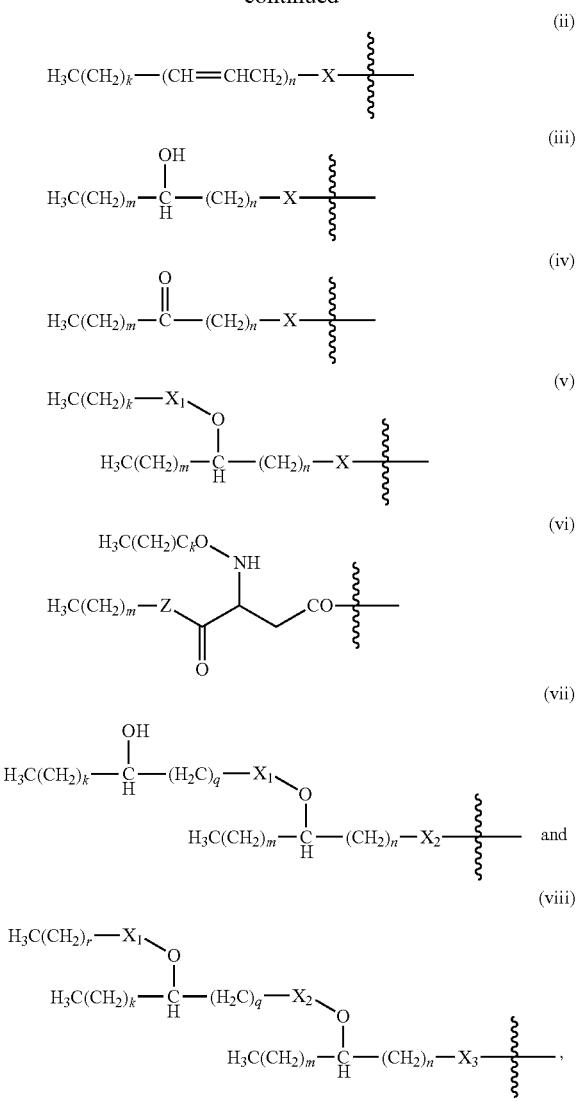

wherein X, $X_1$, $X_2$, and $X_3$ are independently —CO— or —CH$_2$—;
Z is —NH— or —O—;
k, m, and r are independently an integer of 0 to 30 inclusive,
n and q are independently an integer of 0 to 6 inclusive;
at least one of $R_1$, $R_3$, $R_5$ and $R_6$ is not hydrogen;
$R_2$ and $R_7$ are independently selected from the group consisting of H, —P(O)(OH)$_2$, —SO$_3$H, —P(O)(OH)(OCH$_2$CH$_2$NH$_2$), and —CH$_2$COOH; and
$R_9$ is H, or an alkyl or acyl group of 1 to 10 carbon length.

In some embodiments, $R_1$ and $R_9$ are hydrogen; $R_2$ is a hydrogen or the phosphono group —P(O)(OH)$_2$; $R_7$ is the phosphono group —P(O)(OH)$_2$; and $R_3$, $R_5$ and $R_6$ are the same or different acyl groups of the following structure

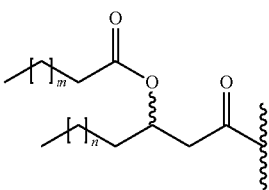

wherein m and n are independently chosen from an integer between 6 to 10 inclusive.

In some embodiments, $R_3$, $R_5$ and $R_6$ are identical.
In some embodiments, an adjuvant is
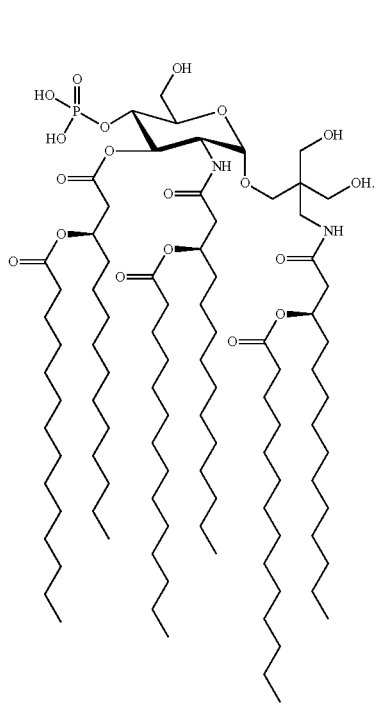
In some embodiments, an adjuvant has the following structure
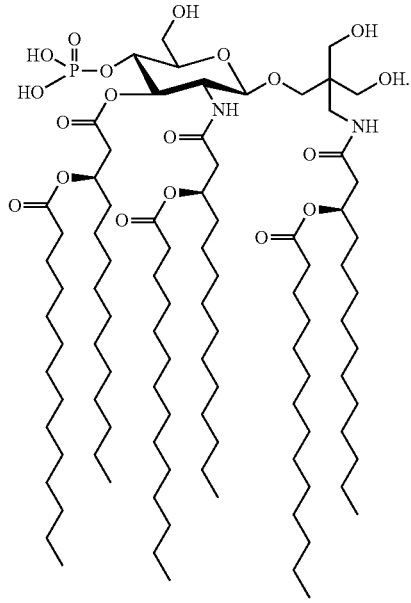
(PET Lipid A)
In some embodiments, an adjuvant is:
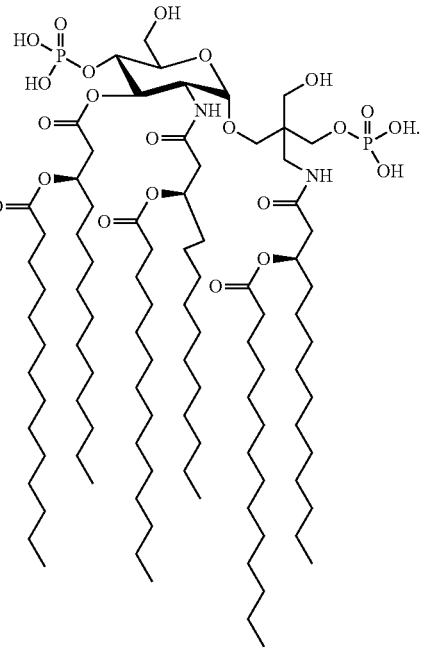
In some embodiments an adjuvant has the following structure
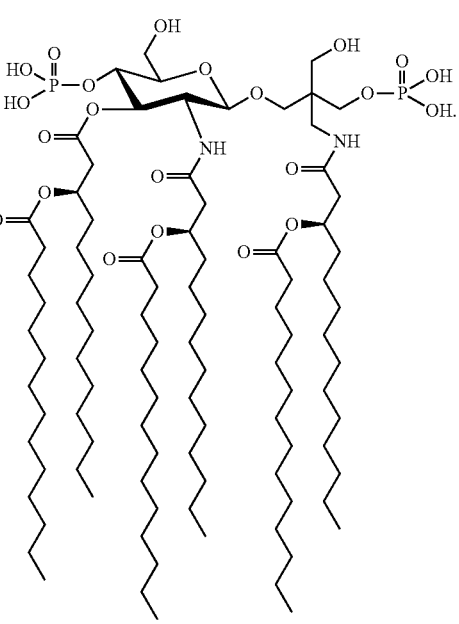

In some embodiments, an adjuvant is a compound defined by the following structure:

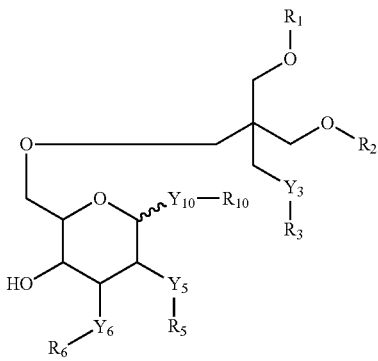

wherein $Y_3$, $Y_5$ and $Y_6$ are independently —O— or —NH—;
$Y_{10}$ is selected from the group consisting of —O—, —NH— and —S—;
$R_1$, $R_3$, $R_5$ and $R_6$ are independently hydrogen or a lipophilic group selected from the group consisting of

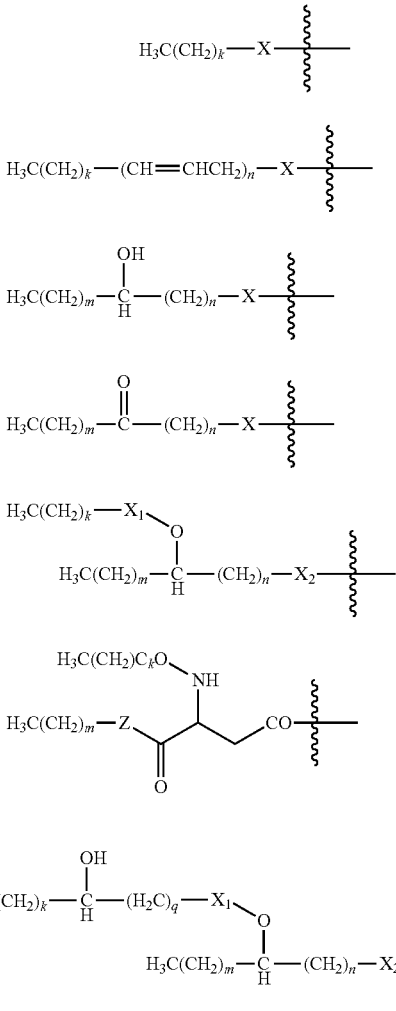

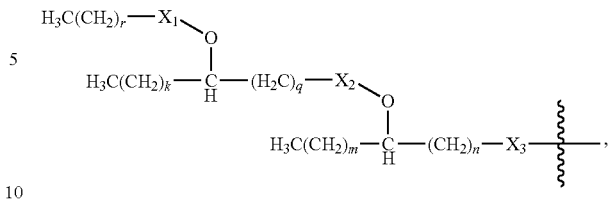

wherein X, $X_1$, $X_2$, and $X_3$ are independently CO or $CH_2$;
Z is NH or O;
k, m, and r are independently an integer of 0 to 30 inclusive,
n and q are independently an integer of 0 to 6 inclusive;
and at least one of $R_1$, $R_3$, $R_5$ and $R_6$ is not a hydrogen atom;
$R_2$ is selected from the group consisting of H, —P(O)(OH)$_2$, —SO$_3$H, —P(O)(OH)(OCH$_2$CH$_2$NH$_2$), and —CH$_2$COOH; and
$R_{10}$ is selected from the group consisting of H, O(O)(OH)$_2$, —SO$_3$H, —P(O)(OH)(OCH$_2$CH$_2$NH$_2$)—CH$_2$COOH, and an alkyl group of 1 to 10 carbon length, or a pharmaceutically acceptable salt thereof.

In some embodiments, the adjuvant has the following structure

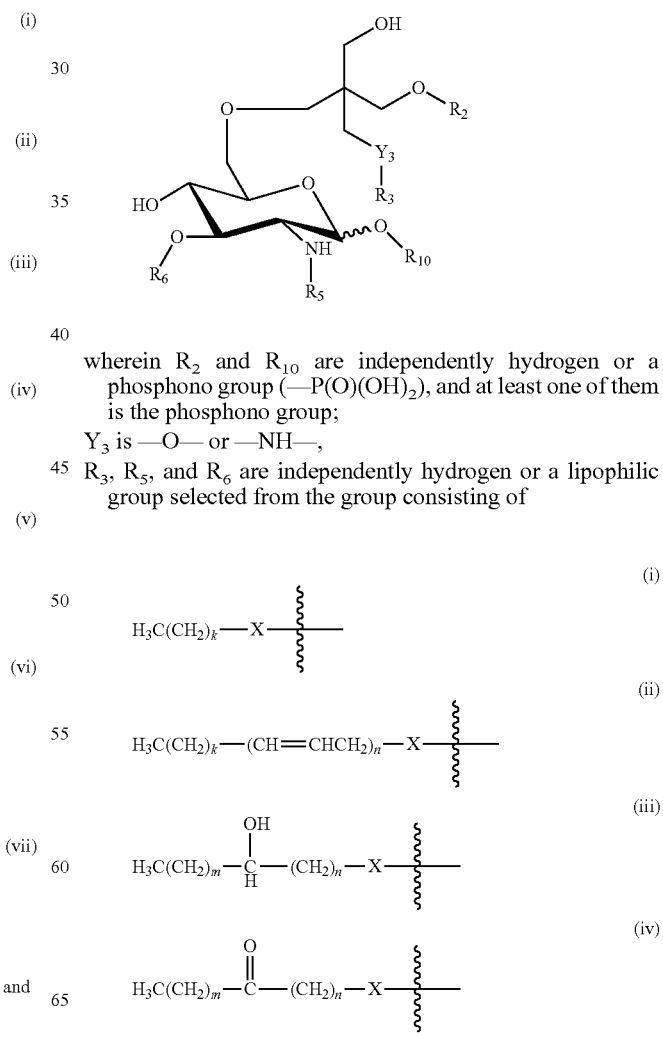

wherein $R_2$ and $R_{10}$ are independently hydrogen or a phosphono group (—P(O)(OH)$_2$), and at least one of them is the phosphono group;
$Y_3$ is —O— or —NH—,
$R_3$, $R_5$, and $R_6$ are independently hydrogen or a lipophilic group selected from the group consisting of -continued

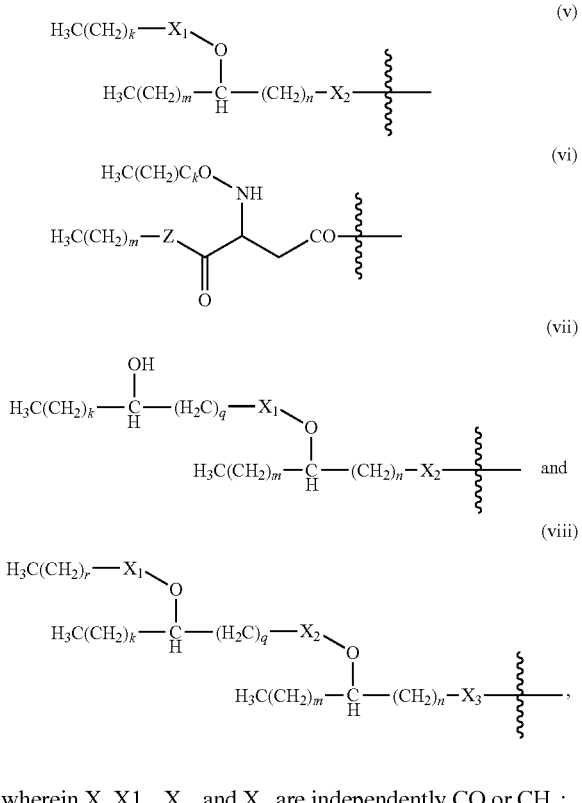

wherein X, X1$_1$, X$_2$, and X$_3$ are independently CO or CH$_2$;
Z is NH or O;
k, m, and r are independently an integer of 0 to 30 inclusive,
n and q are independently an integer of 0 to 6 inclusive;
and at least one of R$_3$, R$_5$, and R$_6$ is not hydrogen.

In some embodiments, the adjuvant has the following structure

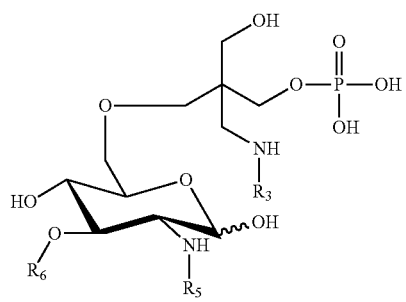

wherein R$_3$, R$_5$ and R$_6$ are the same or different substitution group(s) of the following structure

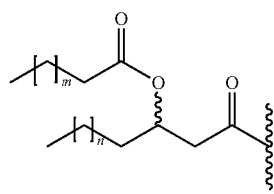

wherein m and n are independently chosen from an integer between 6 to 10 inclusive.

In some embodiments, the adjuvant has the following structure

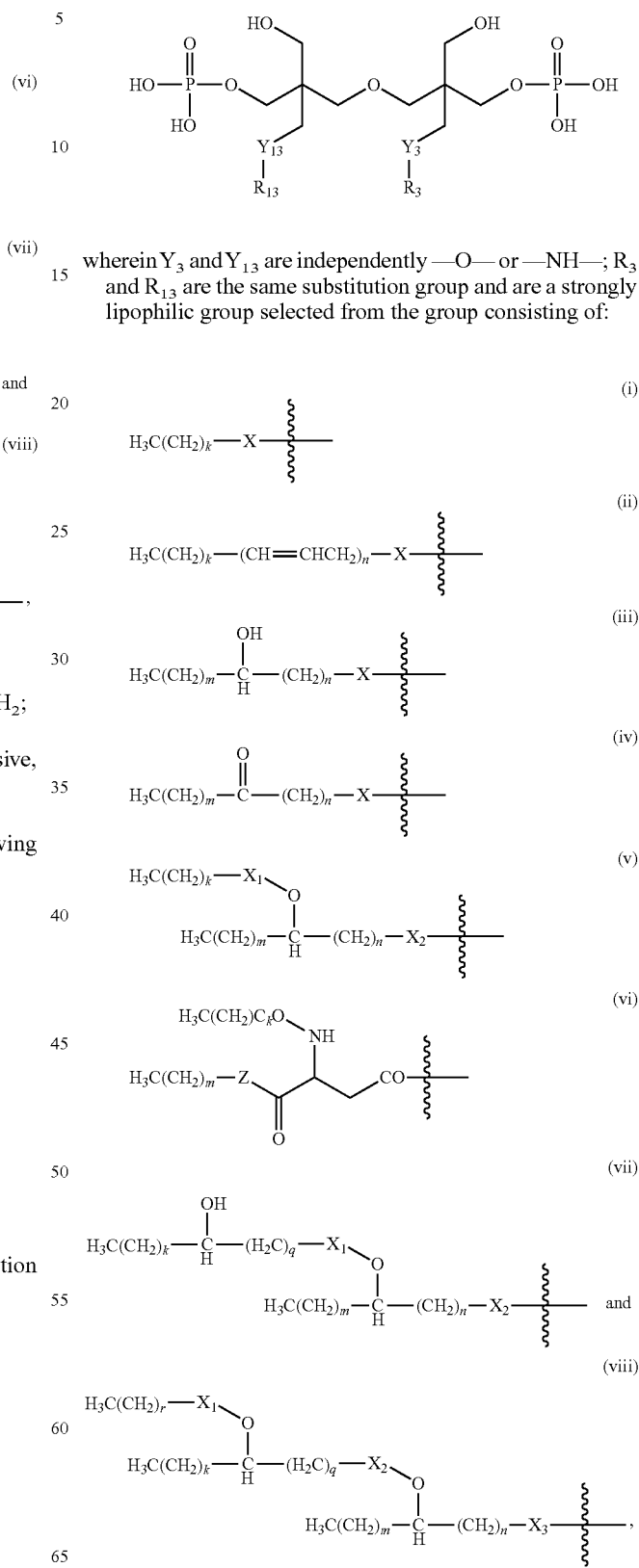

wherein Y$_3$ and Y$_{13}$ are independently —O— or —NH—; R$_3$ and R$_{13}$ are the same substitution group and are a strongly lipophilic group selected from the group consisting of:

wherein X, X₁, X₂, and X, are independently CO or CH₂; Z is NH and O; k, m, and r are independently an integer of 0 to 30 inclusive, n and q are independently an integer of 0 to 6 inclusive.

In some embodiments, the adjuvant has the following structure

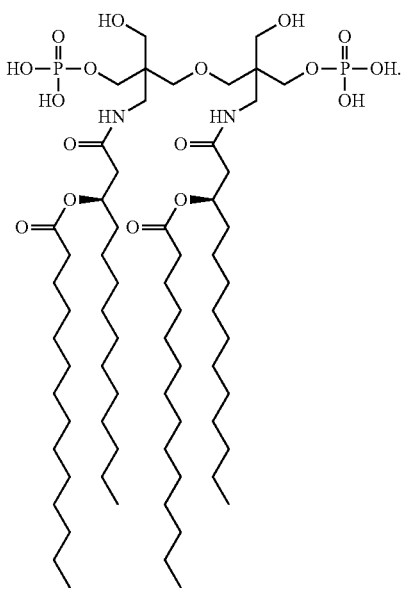

In some embodiments, the adjuvant has the following structure

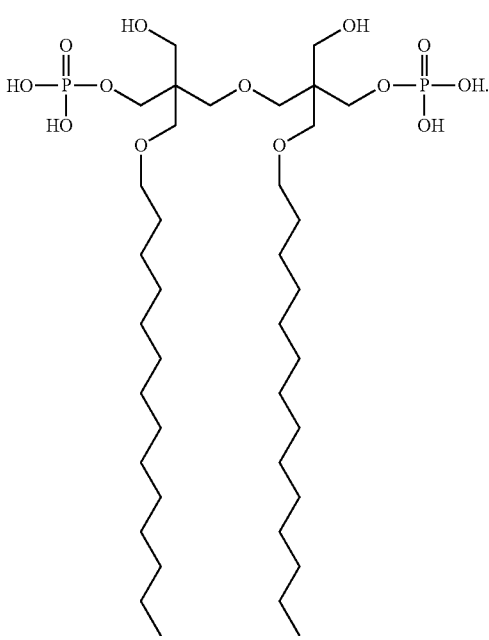

In some embodiments, the strongly lipophilic groups of said compound collectively provide at least three major carbon chains, and wherein the major carbon chains of said strongly lipophilic groups collectively provide at least 40 carbon atoms. In some embodiments, the strongly lipophilic groups of said compound collectively provide at least four major carbon chains and wherein the major carbon chains collectively provide at least 50 carbon atoms. In some embodiments, the strongly lipophilic groups of said compound collectively provide at least four major carbon chains and wherein the major carbon chains collectively provide at least 50 carbon atoms.

In some embodiments, a compound of Formula I or Formula II comprises a Pentaerythritol (PET) unit or a derivative of a PET unit. In some of such embodiments, a PET unit has the structure:

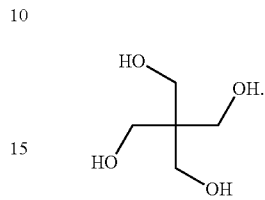

In some embodiments, Lipid A is modified by ring-opening of a sugar unit to provide a PET group; the PET group is optionally modified (e.g., to yield an ether derivative, an amide derivative, an ester derivative and the like).

In some embodiments, of Formula II, at least two major carbon chains are connected, without any intermediate PET unit, to the first PET unit, and at least two major carbon chains are connected, without any intermediate PET unit, to the second PET unit. In some embodiments, at least two major carbon chains are connected, without any intermediate PET unit, to the sugar unit, and at least two major carbon chains are connected, without any intermediate sugar unit, to the PET unit. In some embodiments, the strongly lipophilic groups collectively provide six major carbon chains. In some embodiments, the strongly lipophilic groups collectively provide six major carbon chains.

In some embodiments, each major carbon chain is characterized by 10, 12, 14, 16, 18 or 20 carbon atoms in said chain. In some embodiments, each major carbon chain is characterized by 10, 12, 14, 16, 18 or 20 carbon atoms in said chain. In some embodiments, each major carbon chain is 10, 12, 14, 16, 18 or 20 carbons. In some embodiments, each major carbon chain is 10, 12, 14, 16, 18 or 20 carbons. In some embodiments, each major carbon chain is 10, 12, 14, 16, 18 or 20 carbons.

In some embodiments, any adjuvant described above has lipid A antagonist activity.

In some embodiments, adjuvants described above are present as salts in the liposomal vaccine formulations provided herein. Examples of such salts include and are not limited to triethylamine or diisopropylethylamine salts, other ammonium salts, triethanolamine salts, acetate, citrate, tartarate, mesylate, besylate, tosylate, maleate, fumarate, oxalate, triflate, hydrochloride, hydrobromide, phosphate, sulfate salts and the like. Other such salts include and are not limited to NaOH, KOH, MgOH, CaOH, ZnOH, ethylenediamine, ethanolamine (2-aminoethanol), 1H-Imidazole, diethylamine, piperazine, deanol, choline salts and the like.

In specific embodiments, a liposomal vaccine formulation described herein comprises PET Lipid A, i.e., a phosphoglycolipid adjuvant pentaerythritol-6-chain-C14-glucosamine-mono-phosphate. In specific embodiments, a liposomal vaccine formulation described herein comprises a triethylamine salt of PET Lipid A. The IUPAC name for PET Lipid A TEA salt is triethylammonium (2R,3S,4R,5R,6R)-6-(3-hydroxy-2-(hydroxymethyl)-2-(((R)-3-(tetradecanoyloxy) tetradecanamido)methyl)propoxy)-2-(hydroxymethyl)-5-((R)-3-(tetradecanoyloxy)tetradecanamido)-4-((R)-3-(tetradecanoyloxy)tetradecanoyloxy)tetrahydro-2H-pyran-3-yl hydrogenphosphate. Certain physical properties of PET Lipid A are shown below:

| Parameter | Characteristic |
|---|---|
| Molecular weight (free acid) | 1686.43 g/mol |
| Molecular weight (TEA salt) | 1787.62 g/mol |
| Molecular formula (free acid) | $C_{95}H_{181}N_2O_{19}P$ |
| Molecular formula (TEA salt) | $C_{95}H_{180}N_2O_{19}P \cdot C_6H_{16}N$ |

Liposomes

The vaccine formulations described herein are liposomal vaccine formulations. Exemplary liposomes suitable for incorporation in the formulations include and are not limited to multilamellar vesicles (MLV), oligolamellar vesicles (OLV), unilamellar vesicles (UV), small unilamellar vesicles (SUV), medium-sized unilamellar vesicles (MUV), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV). Techniques for preparing liposomes are described in, for example, COLLOIDAL DRUG DELIVERY SYSTEMS, vol. 66 (J. Kreuter ed., Marcel Dekker, Inc. (1994)).

Depending on the method of preparation, liposomes are unilamellar or multilamellar, and vary in size with diameters ranging from about 0.02 μm to greater than about 10 μm.

Liposomes adsorb to many types of cells and then release an incorporated agent (e.g., a glycolipopeptide comprising one or more copies of a core tandem repeat of SEQ ID NO: 1). In some cases, the liposomes fuse with the target cell, whereby the contents of the liposome then empty into the target cell. Alternatively, a liposome is endocytosed by cells that are phagocytic. Endocytosis is followed by intralysosomal degradation of liposomal lipids and release of the encapsulated agents. Scherphof et al., Ann. N.Y. Acad. Sci., 446: 368 (1985).

The liposomes provided herein also comprise carrier lipids. In some embodiments the carrier lipids are phospholipids. Carrier lipids capable of forming liposomes include, but are not limited to dipalmitoylphosphatidylcholine (DPPC), phosphatidylcholine (PC; lecithin), phosphatidic acid (PA), phosphatidylglycerol (PG), phosphatidylethanolamine (PE), phosphatidylserine (PS). Other suitable phospholipids further include distearoylphosphatidylcholine (DSPC), dimyristoylphosphatidylcholine (DMPC), dipalmitoylphosphatidyglycerol (DPPG), distearoylphosphatidyglycerol (DSPG), dimyristoylphosphatidylglycerol (DMPG), dipalmitoylphosphatidic acid (DPPA); dimyristoylphosphatidic acid (DMPA), distearoylphosphatidic acid (DSPA), dipalmitoylphosphatidylserine (DPPS), dimyristoylphosphatidylserine (DMPS), distearoylphosphatidylserine (DSPS), dipalmitoylphosphatidyethanolamine (DPPE), dimyristoylphosphatidylethanolamine (DMPE), distearoylphosphatidylethanolamine (DSPE) and the like, or combinations thereof. In some embodiments, the liposomes further comprise a sterol (e.g., cholesterol) which modulates liposome formation. In some embodiments, the carrier lipids are any known non-phosphate polar lipids.

In some embodiments, a liposome described herein comprises one or more copies of a glycosylated core tandem repeat of SEQ ID NO: 1 attached to a dilipidated amino acid sequence. In some other embodiments, a liposome described herein comprises one or more copies of a glycosylated core tandem repeat of SEQ ID NO: 1 attached to a dilipidated amino acid sequence, and also an adjuvant. In yet further embodiments, a liposome described herein comprises one or more copies of a glycosylated core tandem repeat of SEQ ID NO: 1 attached to a dilipidated amino acid sequence, an adjuvant and carrier lipids. In any of the aforementioned embodiments, a liposome described herein comprises a mixture of adjuvants (e.g., an adjuvant of Formula I and CpG ODN, synthetic TLR-9 agonists, saponin, or the like).

In specific embodiments, a vaccine formulation described herein is produced using a simultaneous mixing step where there is controlled—mixing of organic and aqueous phases. In some embodiments, an organic phase comprises an organic solvent. In some embodiments, an organic phase comprises an organic solvent and up to about 20% v/v water. In some embodiments, an organic phase comprises an organic solvent and up to about 15% v/v of water. In some embodiments, an organic phase comprises an organic solvent and up to about 10% v/v of water. In some embodiments, an organic phase comprises an organic solvent and up to about 5% water. In some embodiments, an organic phase comprises an organic solvent and less than about 5% v/v of water. In some of such embodiments, the presence of water in the organic phase allows for improved dissolution of a solute (e.g., a glycolipopeptide). In some of such embodiments, the organic phase comprises an organic solvent which is miscible with water.

In some embodiments, an aqueous phase optionally comprises up to about 20% v/v of an organic solvent. In some embodiments, an aqueous phase optionally comprises up to about 15% v/v of an organic solvent. In some embodiments, an aqueous phase optionally comprises up to about 10% v/v of an organic solvent. In some embodiments, an aqueous phase optionally comprises up to about 5% v/v of an organic solvent.

By way of example, the carrier lipids and glycolipopetide (e.g., a glycolipopeptide of SEQ ID NO: 2) and adjuvant (e.g., PET Lipid A, PET Lipid A triethylamine salt) are fully solubilized in an organic phase which optionally contains up to 5% v/v water (e.g., t-BuOH containing up to 5% v/v water). Liposome size is controlled through the use of simultaneous mixing of the two phases using a controlled ratio of flow rates. The ratio of flow rates of the aqueous to the organic phases is held constant at about 3:1 to yield liposomes with a population distribution of about 90% (d90)≤0.22 μm allowing for filtration through an aseptic filter. In some embodiments, the liposomes have a population distribution of about 90% (d90) ≤0.4 μm. In some embodiments, the liposomes have a population distribution of about 90% (d90)≤0.30 μm. In some embodiments, the liposomes have a population distribution of about 90% (d90)≤0.25 μm. In some embodiments, the liposomes have a population distribution of about 90% (d90) ≤0.20 μm.

Certain parameters that are optionally modified in the liposome preparation include the aqueous/organic mixing ratio, temperatures as well as cooling rate to obtain liposomes that are suitable for incorporation in vaccine formulations described herein. FIG. 1 illustrates an exemplary procedure for manufacture of liposomal vaccine formulations described herein.

Ratio of Flow Rates Between Lipid Solution and Water

Providing that the start and stop of water and organic phase flow are simultaneous, ratio of water to organic solution flow rate determines solvent concentration and, consequently, liposome size. The higher the solvent concentration is, the larger the formed liposomes will be. Accordingly, in some embodiments, the ratio of water flow rate to organic solution flow rates is at least 2:1 (yielding an organic solvent concentration of not more than about 33⅓%), at least 3:1 (yielding an organic solvent concentration of not more than about 25%). In some embodiments, the ratio of water flow rate to organic solution flow rates is at least 5.67:1 (yielding an organic solvent concentration of not more than about 15%), The ratio of water flow rate to organic solution flow rate is typically not more than 19:1. In some embodiments, the ratio of water flow rate to organic solution flow rate is between about 19:1 (achieving an organic solvent concentration of about 5%) and 3⅓:1 (achieving an organic solvent concentration of about 30%), between about 9:1 (achieving an organic solvent concentration of about 10%), and 5:1 (achieving an organic solvent concentration of about 20%), or between about 9:1 and 4:1 (achieving an organic solvent concentration of about 25%). By way of example, a 15% v/v concentration of t-Butanol in water is obtained by flowing 85 mL/min water to 15 mL/min organic phase to provide liposome particle size of substantially uniform d90. In any of the aforementioned embodiments, an organic phase is any organic phase described herein.

Accordingly, flow rate is adjusted as practical for a given desired liposome size, as long as ratio is kept constant. Thus, for example, if it is desired to produce a liposome preparation where more than about 99% of liposomes are of a size less than about 200 nm, and the concentration of organic solution concentration is about 20%, then flow rates are adjusted, while keeping a ratio of water flow rate to lipid solution flow rate of about 4-to-1, according to practical considerations such as practical mixing time and volume of solutions to be used.

Temperature of the Liquids

The liquids are optionally heated whilst in their respective holding tanks, which can be insulated with jackets to reduce heat loss. The temperature of either liquid is held between about 40° C.-45° C., about 45° C.-50° C., about 50° C.-55° C., or about 55° C.-60° C. In some embodiments, the temperature of either liquid is held at about 42° C.±2° C., 44° C.±2° C., 47° C.±2° C., 50° C.±2° C., 53° C.±2° C., 55° C. 2° C., 57° C.±2° C., or 60° C.±2° C. In some embodiments, the temperature of either liquid is held at about 53° C.±2° C.

Cooling

In some embodiments, rapid cooling, made feasible by the use of a heat exchanger immediately following formation of liposomes, allows for control of liposome size and removes an obstacle to batch size independence and variability in liposome size. In order to maintain liposome size cooling temperature and time should not exceed about 20° C. in 5 hours, e.g. cooling from about 55° C. to about 35° C. in less than 5 hours, or from about 55° C. to about 30° C. in less than 2 hours, or from about 55° C. to about 30° C. in less than 30 minutes. The mixture is optionally cooled to lower temperatures if desired; however the bulk solution is kept above freezing temperature.

An apparatus for manufacture of liposomes using procedures described above is described in U.S. Ser. No. 13/140,786 (published as U.S. Pat. Application No. 2012/0034294), which disclosure is incorporated herein by reference.

In one embodiment, a lyophile (i.e., a suspension comprising liposomes) obtained from the controlled mixing step described above is sterile filtered, transferred to vials and subjected to freeze drying to provide a lyophilized cake or powder comprising liposomes. Such a cake or powder is reconstituted in saline (e.g., 0.9% w/v sterile saline) prior to administration to an individual in need thereof. In another embodiment, a lyophile (i.e., a suspension comprising liposomes) obtained from the controlled mixing step described above is sterile filtered and is directly administered to an individual in need thereof. In yet other embodiments, a lyophile (i.e., a suspension comprising liposomes) obtained from the controlled mixing step described above is sterile filtered, placed in vials and evaporated and/or concentrated (e.g., under reduced pressure) to provide a dried thin-film or powder which is then reconstituted prior to administration to an individual in need thereof.

In some embodiments a liquid used for reconstitution of a liposomal thin film or powder or lyophilized cake or solid described above is saline (e.g., 0.9% w/v saline). In some embodiments, a liquid used for reconstitution of a liposomal thin film or powder or lyophilized cake or solid described above is any other parenterally acceptable diluents (e.g, D5W, lactated Ringers solution, dextrose solution and the like). In some embodiments, a liquid used for reconstitution of a liposomal thin film or powder or lyophilized cake or solid described above is an oil. In some of such embodiments, contemplated within the scope of embodiments presented herein is the use of a pharmaceutically acceptable oil as diluent for preparation of sustained release vaccine formulations. In some of such embodiments, vaccine formulations that are suspensions in oil allow for formation of a sustained release depot (e.g., a subcutaneous or intramuscular pocket of suspension in oil) upon administration, thereby allowing extended release. Examples of such diluents used for formulating suspensions in oil comprising liposomes described herein include, and are not limited, to soybean oil, oleic acid and its glyceride derivatives, olive oil, castor oil, and the like. In some of such embodiments, a liposomal vaccine formulation provided herein is an emulsion. In some of such embodiments, a liposomal vaccine formulation provided herein is a suspension in oil.

In some embodiments, a liposomal vaccine formulation described herein comprises a weight to weight ratio of glycodilipidated peptide (e.g., SEQ ID NO: 2) to adjuvant (e.g., PET Lipid A, TEA salt) of from about 10:1 to about 1:10. In some embodiments, a liposomal vaccine formulation described herein comprises a weight to weight ratio of glycodilipidated peptide (e.g., SEQ ID NO: 2) to adjuvant (e.g., PET Lipid A, TEA salt) of from about 8:1 to about 1:8. In some embodiments, a liposomal vaccine formulation described herein comprises a weight to weight ratio of glycodilipidated peptide (e.g., SEQ ID NO: 2) to adjuvant (e.g., PET Lipid A, TEA salt) of from about 5:1 to about 1:5. In some embodiments, a liposomal vaccine formulation described herein comprises a weight to weight ratio of glycodilipidated peptide (e.g., SEQ ID NO: 2) to adjuvant (e.g., PET Lipid A, TEA salt) of from about 2:1 to about 1:2. In some embodiments, a liposomal vaccine formulation described herein comprises a weight to weight ratio of glycodilipidated peptide (e.g., SEQ ID NO: 2) to adjuvant (e.g., PET Lipid A, TEA salt) of 1:1. In some specific embodiments, a liposomal vaccine formulation described herein comprises about 300 µg glycodilipidated peptide (e.g., SEQ ID NO: 2) and about 150 µg of adjuvant (e.g., PET Lipid A, TEA salt). In some embodiments, a liposomal vaccine formulation described herein comprises about 600 µg glycodilipidated peptide (e.g., SEQ ID NO: 2) and about 300 µg of adjuvant (e.g., PET Lipid A, TEA salt). In some embodiments, a liposomal vaccine formulation described herein comprises about 900 µg glycodilipidated peptide (e.g., SEQ ID NO: 2) and about 450 µg of adjuvant (e.g., PET Lipid A, TEA salt). In some embodiments, a liposomal vaccine formulation described herein comprises about 1200 µg glycodilipidated peptide (e.g., SEQ ID NO: 2) and about 600 µg of adjuvant (e.g., PET Lipid A, TEA salt). In some of such embodiments, the liposomal formulation is a lyophilized solid powder or cake which is reconstituted in saline (e.g., 0.9% w/v sterile saline) to provide the vaccine formulation.

Any combination of one or more copies of a glycosylated core tandem repeat (SEQ ID NO: 1), a dilipidated amino acid sequence, and one or more adjuvants described above for the various variables is contemplated herein. Throughout the specification, glycolipopeptides, and compositions and meth-

Methods of Treatment

Provided herein, in some embodiments, are methods for stimulating the immune system of an individual in need thereof comprising administration of a liposomal vaccine formulation described herein (e.g., a glycolipopeptide formulation comprising one or more copies of SEQ ID NO: 1 and an adjuvant (e.g., PET Lipid A). In some instances, the administration of a liposomal vaccine formulation described herein induces and/or sustains a cellular response. In other instances, the administration of a liposomal vaccine formulation described herein induces and/or sustains a humoral response. In further instances, the administration of a liposomal vaccine formulation described herein induces and/or sustains both a humoral and cellular response.

Also provided herein are methods for treatment of cancer in an individual in need thereof comprising administration of a liposomal vaccine formulation described herein. In some of such embodiments, the individual is suffering from cancer. In other embodiments, the individual is suspected to be suffering from cancer. In yet other embodiments, the individual is pre-disposed to cancer (e.g., an individual pre-disposed to breast cancer). In certain embodiments, the cancer is selected from the group consisting of breast cancer, lung cancer, adenocarcinoma of the lung, squamous cell lung cancer, small cell lung cancer, non-small cell lung cancer, head and neck cancer, brain cancer, abdominal cancer, colon cancer, colorectal cancer, esophageal cancer, parapharyngeal cancer, gastrointestinal cancer, glioma, liver cancer, oral cancer, tongue cancer, neuroblastoma, osteosarcoma, ovarian cancer, renal cancer, urinary bladder cancer, urinary tract cancer, pancreatic cancer, retinoblastoma, cervical cancer, uterine cancer, Wilm's tumor, multiple myeloma, skin cancer, lymphoma, leukemia, blood cancer, thyroid cancer, bone cancer, adenocystic tumor, chondrosarcoma, pancreatic islet cell tumor, neuroendocrine tumor, prostate cancer, ovarian cancer, glioblastoma, endometrial carcinoma, endometrial cancer, leiomyosarcoma, gall bladder cancer, hepatocellular cancer, hematological cancer, multiple myeloma, acute myelogenous leukemia, acute/chronic lymphoblastic leukemia, hairy-cell leukemia, follicular lymphoma, multiple myeloma, plasmacytoma, diffuse large B-cell lymphoma. In certain embodiments, the cancer is head and neck cancer, lung cancer, colon cancer or prostate cancer. In certain embodiments, the cancer is non-small cell lung cancer. In some embodiments, the cancer is a hematological cancer.

In some embodiments, the cancer is associated with expression of the MUC1 antigen including but not limited to breast, non-small cell lung, ovarian, colorectal, gastric, prostate, pancreatic, and renal cell cancers. In some embodiments, the cancer is associated with solid tumors. In certain instances, the solid tumors are advanced, e.g., stage 3 or 4. In some instances, the tumors are breast tumors, non-small cell lung tumors, ovarian tumors, colorectal tumors, gastric tumors, prostate tumors, pancreatic tumors, and renal cell cancer tumors. In certain instances, the solid tumors are histologically associated with the expression of the MUC1 antigen.

As used herein, in some embodiments, "treatment" or "treating" or "treated" refers to therapeutic treatment wherein the object is to slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. In other embodiments, "treatment" or "treating" or "treated" refers to prophylactic measures, wherein the object is to delay onset of or reduce severity of an undesired physiological condition, disorder or disease, such as, for example is a person who is predisposed to a disease (e.g., an individual who carries a genetic marker for a disease such as breast cancer).

The methods of treatment described herein treat various stages of cancer including stages which are locally advanced, metastatic and/or recurrent. In cancer staging, locally advanced is generally defined as cancer that has spread from a localized area to nearby tissues and/or lymph nodes. In the Roman numeral staging system, locally advanced usually is classified in Stage II or III. Cancer which is metastatic is a stage where the cancer spreads throughout the body to distant tissues and organs (stage IV). Cancer designated as recurrent generally is defined as the cancer has recurred, usually after a period of time, after being in remission or after a tumor has visibly been eliminated. Recurrence can either be local, i.e., appearing in the same location as the original, or distant, i.e., appearing in a different part of the body. In certain instances, a cancer treatable by combination therapies described herein is unresectable, or unable to be removed by surgery.

In some of such embodiments, the methods of treatment (e.g., immunotherapy) described herein provide adjunct therapy to any other cancer therapy prescribed for an individual. Accordingly, in some embodiments, liposomal vaccine formulations described herein are administered in combination with treatment with any other anti-cancer agent including and not limited to methotrexate (RHEUMATREX®, Amethopterin) cyclophosphamide (CYTOXAN®), thalidomide (THALIDOMID®), acridine carboxamide, Actimid®, actinomycin, 17-N-allylamino-17-demethoxygeldanamycin, aminopterin, amsacrine, anthracycline, antineoplastic, antineoplaston, 5-azacytidine, azathioprine, BL22, bendamustine, biricodar, bleomycin, bortezomib, bryostatin, busulfan, calyculin, camptothecin, capecitabine, carboplatin, cetuximab, chlorambucil, cisplatin, cladribine, clofarabine, cytarabine, dacarbazine, dasatinib, daunorubicin, decitabine, dichloroacetic acid, discodermolide, docetaxel, doxorubicin, epirubicin, epothilone, eribulin, estramustine, etoposide, exatecan, exisulind, ferruginol, floxuridine, fludarabine, fluorouracil, fosfestrol, fotemustine, ganciclovir, gemcitabine, hydroxyurea, IT-101, idarubicin, ifosfamide, imiquimod, irinotecan, irofulven, ixabepilone, laniquidar, lapatinib, lenalidomide, lomustine, lurtotecan, mafosfamide, masoprocol, mechlorethamine, melphalan, mercaptopurine, mitomycin, mitotane, mitoxantrone, nelarabine, nilotinib, oblimersen, oxaliplatin, PAC-1, paclitaxel, pemetrexed, pentostatin, pipobroman, pixantrone, plicamycin, procarbazine, proteasome inhibitors (e.g., obortezomib), raltitrexed, rebeccamycin, Revlimid®, rubitecan, SN-38, salinosporamide A, satraplatin, streptozotocin, swainsonine, tariquidar, taxane, tegafur-uracil, temozolomide, testolactone, thioTEPA, tioguanine, topotecan, trabectedin, tretinoin, triplatin tetranitrate, tris(2-chloroethyl)amine, troxacitabine, uracil mustard, valrubicin, vinblastine, vincristine, vinorelbine, vorinostat, zosuquidar, or the like.

In additional embodiments, the methods of treatment (e.g., immunotherapy) described herein i.e., liposomal vaccine formulations described herein are administered in combination with radiotherapy (e.g., γ-rays, X-rays, and/or the directed delivery of radioisotopes to tumor cells, microwaves, UV radiation and the like. In additional embodiments, the methods of treatment (e.g., immunotherapy) described herein i.e., liposomal vaccine formulations described herein are administered in combination with gene therapy. Therapeutic genes include an antisense version of an inducer of cellular proliferation (oncogene), an inhibitor of cellular proliferation (tumor suppressor), or an inducer of programmed cell death (pro-apoptotic gene). In some embodiments, the combination therapies described herein are administered with a surgery (e.g., resection).

In additional embodiments, the methods of treatment (e.g., immunotherapy) described herein i.e., liposomal vaccine formulations described herein are administered in combination with anti-diaarrheal agents, anti-emetic agents, analgesics, opioids and/or non-steroidal anti-inflamatory agents.

In further embodiments, a liposomal vaccine formulation described herein (e.g., a formulation comprising SEQ ID NO: 2 and PET Lipid A TEA salt) is administered to an individual who has been pre-treated with cyclophosphamide, or imitanib, or daclizumab and/or any other anti-cancer agent. In other embodiments, a liposomal vaccine formulation described herein is administered to an individual who has not been pre-treated with cyclophosphamide and/or any other anti-cancer agent.

In some of the above embodiments, treatment with a liposomal vaccine formulation described herein (e.g., a formulation comprising SEQ ID NO: 2) prolongs lifespan and/or increases survival rates for individuals suffering from cancer. In some of the above embodiments, treatment with a liposomal vaccine formulation described herein (e.g., a formulation comprising SEQ ID NO: 2) improves quality of life for an individual suffering from cancer (e.g., an individual needs a lower dose of an anti-cancer drug that causes side-effects when the individual is immunized with a vaccine formulation described herein).

In some of the above embodiments, treatment with a liposomal vaccine formulation described herein (e.g., a formulation comprising SEQ ID NO: 2) induces and/or sustains an immune response in an individual. Immune responses include humoral responses (i.e., the production of antibodies), cellular responses (i.e., proliferation and stimulation of T-lymphocytes), or both. Measurement of activation and duration of cellular responses are by any known method including, for example, cytotoxic T-lymphocyte (CTL) assays. Humoral responses are also measured by known methods including isolation and quantitation of antibody titers specific to the liposomal vaccine such as IgG or IgM antibody fractions.

Also provided herein are methods for treating a disease, disorder or condition associated with aberrantly glycosylated MUC1 in an individual comprising administering to an individual having aberrantly glycosylated MUC1 a liposomal vaccine formulation described herein. In some embodiments of the methods described herein, the methods include treatment of MUC1 with altered patterns of glycosylation including under- or hypoglycosylation with respect to normal MUC1 counterparts. In some embodiments, the altered patterns are from different glycosyl units (i.e., different saccharides) with respect to normal MUC1 counterparts. In yet other embodiments of the methods described herein, the methods include treatment of aberrantly glycosylated MUC1 that is due to over- or hyperglycosylation.

Diseases, conditions and disorders exhibiting hypoglycosylated forms of MUC1 include but are not limited to cancers such as those described herein, precursor lesions and neoplasia to cancers, e.g., prostatic or epithelial hyperplasia; pancreatitis; inflammatory bowel disease; events that induce inflammation in tissues that express MUC1, e.g., lactation and/or mastitis, pelvic surgery, mumps virus, and smoking; and other inflamed tissue phenotypes such as inflammation in the intestine and colon. Hyperglycosylated forms of MUC1 are found in certain cancers including, but not limited, to squamous cell carcinomas, Bowen's Disease and some breast cancers.

Dosages

When a liposomal vaccine formulation described herein, (e.g., a formulation comprising a glycolipopeptide having one or more copies of a core tandem repeat peptide of SEQ ID NO: 1), is being given to an individual, one of skill in the art understands that the dosage depends on several factors, including, but not limited to, the individual's weight, tumor size, or tumor progression. Generally, as used herein, an individual that receives a vaccine formulation described herein (e.g., a formulation comprising SEQ ID NO: 2 and PET Lipid A adjuvant), is a single organism. In certain embodiments, an individual will be a mammal. Specifically, an individual is a human, including being a male or a female. In many embodiments, the individual will be a patient, or an individual awaiting or under medical care and treatment.

An individual is optionally administered a dose of about 50 µg, about 100 µg, about 200 µg, about 300 µg, about 400 µg, about 500 µg, about 600 m, about 700 µg, about 800 µg, about 900 µg, about 1,000 µg, about 1,010 µg, about 1,020 µg, about 1,030 µg, about 1,040 µg, about 1,050 µg, about 1,060 µg, about 1,070 µg, about 1,080 µg, about 1,090 µg, about 1,100 µg, 1,200 µg, 1,300 µg, 1,400 µg, 1,500 µg, 1,600 µg, 1,700 µg, 1,800 µg, 1,900 µg, or about 2,000 µg of a MUC1-based glycolipopolypeptide liposomal vaccine formulation described herein (e.g., a formulation comprising SEQ ID NO: 2 and PET Lipid A adjuvant), in either single or cumulative applications. In specific embodiments, the dose given to the individual is about 1,000 µg of the vaccine formulation per week.

An individual will optionally receive a dose of the MUC1-based glycolipopolypeptide liposomal vaccine formulation described herein (e.g., a formulation comprising SEQ ID NO: 2 and PET Lipid A adjuvant), for example, multiple times daily, every day, every other day, once a week, or any other suitable dosing regimen. In one embodiment, routinely administering encompasses administering a dose of a liposomal vaccine described herein once a week for a period of time. Of course, the dosing regimen optionally comprises other permutations of MUC1 peptide delivery. That is, the vaccine is administered once, twice, three times, four times, five times, six times, or more times a week at a physician's discretion. In some embodiments, individuals will be given at least 5 doses over a period of time. In other embodiments, individuals will be given greater than or fewer than 5 doses. Thus, in one embodiment, an individual will receive a dose of about 1,000 µg of the MUC1 glycolipidated polypeptide every week. Alternatively, the individual will receive two doses of 500 µg, twice a week, or a daily 100 µg dose over five days.

These dosage examples are not limiting and only used to exemplify particular dosing regimens for administering about 1,000 µg of the MUC1 glycolipidated polypeptide. For instance, if the appropriate dose for a given situation is 1,000 µg per week, the doses is optionally broken down into any number of permutations, e.g., four injections of 250 µg per week. This also holds true if the appropriate dose for a particular situation is greater than or less than 1,000 µg.

The period of time that a MUC1-based glycolipopolypeptide liposomal vaccine formulation (e.g., a formulation comprising SEQ ID NO: 2 and PET Lipid A adjuvant), is administered to the individual is any suitable period as determined by the stage of the cancer, the patient's medical history and the attending physician's discretion. Examples of such suitable periods include, but are not limited to, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, or at least about 24 months or longer. The treatment period is optionally continued for longer than 24 months, if desired, such as for 30 months, 31 months, 32 months, 33 months, 34 months, 35 months, 36 months, or longer than 36 months.

In another embodiment, the period of time of dosing for any of the methods described herein is for at least about 2 weeks, at least about 4 weeks, at least about 8 weeks, at least about 16 weeks, at least about 17 weeks, at least about 18 weeks, at least about 19 weeks, at least about 20 weeks, at least about 24 weeks, at least about 28 weeks, at least about 32 weeks, at least about 36 weeks, at least about 40 weeks, at least about 44 weeks, at least about 48 weeks, at least about 52 weeks, at least about 60 weeks, at least about 68 weeks, at least about 72 weeks, at least about 80 weeks, at least about 88 weeks, at least about 96 weeks, or at least about 104 weeks.

Any liposomal vaccine formulation described herein (e.g., a formulation comprising SEQ ID NO: 2 and PET Lipid A adjuvant), is optionally administered in different phases of treatment. For example, the MUC1-based glycolipopolypeptide liposomal vaccine formulation is administered in both a treatment phase and a maintenance phase. In some embodiments, the treatment phase will comprise administration of the liposomal vaccine formulation in weekly dosages, whereas the maintenance phase is for longer time periods, such as about every 6 weeks, about every 7 weeks, about every 8 weeks, about every 9 weeks, about every 10 weeks, about every 11 weeks, about every 12 weeks, or longer. In some cases, the dosage given in the treatment phase will be greater than the dosage given in the maintenance phase. However, treatment and maintenance phases are designed to a particular individual so the time and dosages between the treatment and maintenance phases vary from the above examples. Generally, the maintenance phase begins at any time deemed appropriate. For example, in some embodiments, the treatment phase will be eight weeks and the maintenance phase will continue throughout the individual's lifetime. In other embodiments, only a treatment or a maintenance phase will be undertaken.

In yet further embodiments, a liposomal vaccine described herein (e.g., a formulation comprising SEQ ID NO: 2 and PET Lipid A adjuvant), is given prophylactically. In these embodiments, the administration of the liposomal vaccine formulation prevents onset of cancer in an individual (e.g., an individual genetically pre-disposed to developing cancer, such as breast cancer.

The amount of time that an individual should remain on a vaccine formulation described herein is determined by the attending physician. In some cases, it is advantageous to administer the vaccine formulation for the rest of an individual's lifetime. In some of such embodiments, a vaccine formulation is administered in four quadrants of the body, e.g., near lymph nodes, (e.g., in each armpit), in each buttock (e.g., subcutaneously) and the like. In some of such embodiments, a vaccine formulation is administered via a pump. In some embodiments, a pump and/or delivery device is implanted in an individual to allow chronic dosing. Examples of implantable pumps include and are not limited to Alzet® osmotic pumps.

Kits

Provided herein are kits for dispensing the liposomal vaccine formulations described herein. Such kits comprise a first drug product vial comprising glycolipopeptide comprising one or more copies of a core tandem repeat of SEQ ID NO: 1, and an adjuvant (PET Lipid A, triethylamine salt), and a second vial containing a suitable sterile liquid as described herein for reconstitution. In some embodiments For example, in one embodiment, such kits comprise a first vial, i.e., a drug product vial containing 300 µg of glycolipopeptide comprising one or more copies of a core tandem repeat of SEQ ID NO: 1, and 150 µg of adjuvant (PET Lipid A, triethylamine salt), which represents a 120% fill. This excess is intended to facilitate the withdrawal and administration of the specified dose. The kit further comprises a second vial containing up to 1 mL of 0.9% sodium chloride solution for injection. After reconstitution of the drug product with 0.6 mL of sodium chloride solution for injection (0.9% w/v), a drug product vial yields 0.5 mL for delivery corresponding to 250 µg of a glycolipopeptide comprising one or more copies of a core tandem repeat of SEQ ID NO: 1. By way of example, if the dose is 1 mg total, 4 vials are required per dose.

Certain Definitions

"Major carbon chains" as used herein refer to carbon chains which are a least six carbons in length. The carbon atoms of a carbon chain may be bonded to 3, 2, 1 or 0 hydrogens. In a major carbon chain, the —CH< and >C< carbons are usually branching points for the attachment (with or without a linker) of another carbon chain. They may, in some embodiments, be substituted with a side group, such as amino or hydroxyl. The carbon atoms of any major carbon chain may include one or more carbonyl or thiocarbonyl carbons, i.e., —C(=O)— or —C(=S)—.

"Strongly lipophilic Groups" refers to a lipophilic group comprising at least five atoms other than hydrogen, for which the log P, as predicted by the Meylan algorithm, is greater than 3. The lipophilicity of groups can be determined by measuring the partition coefficient of the molecule HZ (where Z is the side chain in question) between a nonpolar solvent (e.g., ethanol, dioxane, acetone, benzene, n-octanol) and water, at STP. The lipophilicity may be defined as the logarithm of this partition coefficient (log P); it will then be positive for molecules which prefer the nonpolar solvent. Thus, a lipophilic group is one for which log P is greater than zero.

The partition coefficient (P) is defined as the ratio of the equilibrium concentrations of a dissolved substance in a two-phase system consisting of two largely immiscible solvents. One such system is n-octanol:water; the octanol phase will contain about 20% water and the water phase about 0.008% octanol. Thus, the relevant partition coefficient (Pow) is the ratio of the molar concentration of the solute in octanol saturated with water to its molar concentration in water saturated with octanol. N-octanol is a useful surrogate for biological membranes because it, like many membrane components, is amphiphilic. (Reference hereafter to log P shall mean log Pow, unless otherwise stated.)

For more information on methods of determining Pow, see Sangster, J., Octanol-Water Partition Coefficients: Fundamentals and Physical Chemistry (April 1997) (ISBN 0-471-9739). For tabulations of octanol-water partition coefficients, see the EPA "Chemicals in the Environment: OPPT Chemicals Fact Sheets" the USDA Pesticide Properties Database, Sangster, J., "Octanol-Water Partition Coefficients of Simple Organic Compounds", J. Phys. Chem. Ref. Data, 18:1111-1230 (1989); Verbruggen, E. M. J., et al., "Physiochemical Properties of Higher Nonaromatic Hydrocarbons: Literature Study," J. Phys. Chem. Ref. Data, 29:1435-46 (2000). It should be noted that the Pow values compiled for different compounds may have been determined by different methodologies.

In Meylan's method, the predicted log Pow is obtained by adding weighted coefficients for each fragment (the raw coefficient multiplied by the number of copies of that fragment) to the constant 0.2290. The fragments considered include aliphatically attached —CH$_3$ (0.5473), —CH$_2$— (0.4911), —CH (0.3614), —OH (−1.4086), —NH$_2$ (−1.4148), —C(═O)N (−0.5236), (−0.0001), —NH—(−1.4962), N═C (−0.0010), —O-(−1.2566), —CHO (−0.9422), -tert C so 3+C attached (0.2676), C no H not tert (0.9723), —C(═O)O— (−0.9505), —C(═O)—(−1.5586), ═CH or C< (0.3836), #C (0.1334), —C(═O)N (−0.5236), —O—CO—C—N—CO (−0.5), —SO—O (−9), —O—P (−0.0162); —O—P (−2.4239), phosphate attached —OH (0.475); aromatic C (0.2940), aromatic N (5 membered ring) (−0.5262), and aromatically attached —OH (−0.4802).

For strongly lipophilic groups, the log P predicted by the Meylan algorithm is at least 3. In further embodiments, for strongly lipophilic groups, the log P is at least 4, at least 4, at least 5, at least 6, at least 7, at least 8, at least 9, at least 10, or more than 10.

Strongly lipophilic groups comprise one or more carbon chains, and in some embodiments, one or more major carbon chains. Strongly lipophilic groups include simple (unbranched, acyclic) lipids, or a complex (branched and/or cyclic, including partially aromatic) lipids.

In some embodiments, the strongly lipophilic group will comprise not more than 100 atoms other than hydrogen, not more than 80 such atoms, not more than 60 such atoms, or not more than 40 such atoms.

As noted previously, the strongly lipophilic group must comprise at least five atoms other than hydrogen. In some embodiments, it comprises at least six, more preferably at least 8, still more preferably at least 9, even preferably, it comprises at least 11 such atoms, still more preferably at least 13 such atoms, most preferably at least 21 such atoms In some embodiments, the strongly lipophilic group has an elemental composition limited to the elements carbon, silicon, hydrogen, oxygen, nitrogen, sulfur, and phosphorous. In some embodiments, the majority of the bonds within the side chain which do not involve hydrogen are carbon-carbon bonds.

Since the presence of oxygen, nitrogen, sulfur and phosphorous tends to reduce lipophilicity, in the strongly lipophilic group, in some embodiments, more than 50%, or more than 75%, of the non-hydrogen atoms are carbon atoms.

For the same reason, the strongly lipophilic group, in some embodiments, comprises at least 5, at least 6, at least 7, at least 8, at least 9, or at least 10 carbon atoms.

Additional reference to strongly lipophilic groups can be found in U.S. Pat. No. 7,820,627, which is incorporated by reference regarding its discussion and application of lipophilic and strongly lipophilic groups.

EXAMPLES

Example 1

Synthesis of a Liposomal Vaccine Formulation

Glycolipopeptide of SEQ ID NO: 2, (159 mg), PET lipid A (96 mg), DPPC (4.36 g), DMPG Na (0.54 g) and Cholesterol (2.60 g) were dissolved in 117 grams of t-butanol containing 5 mL of sterile water for irrigation.

The heated t-butanol solution and heated sterile water are pumped under separate motors that are set to desirable flow rates such that the ratio of flow rates of the aqueous to the organic phases is held constant at 5.9:1 to yield liposomes with a population distribution of 90% (d90)≦0.22 μm, allowing for filtration through at least one aseptic filter. Using the procedure described in FIG. 1, vials containing lyophilized solid are prepared. The following batch formula is used for a 1L Scale batch which represents 500 vials. The formula is used in fractions or multiples of the stated batch size.

| Component | Amount/vial | Function |
|---|---|---|
| Glycolipopeptide SEQ ID NO: 2 | 0.30 mg | Antigen |
| PET lipid A TEA salt | 0.15 mg | Adjuvant |
| Dipalmitoyl phosphatidylcholine (DPPC) | 8.72 mg | Structural lipid of liposome |
| Dimyristoyl phosphatidylglycerol, sodium salt (DMPG) | 1.09 mg | Structural lipid of liposome |
| Cholesterol | 5.20 mg | Structural lipid of liposome |
| t-BuOH, reagent grade[#] | q.s. | Solvent |
| Sterile water for irrigation[#] | q.s. | Solvent |

[#]Not in final formulation. Water and alcohol are removed during lyophilization The liposome mixture is sterile filtered and lyophilized. The lyophilized drug product is a sterile powder which, upon reconstitution, yields a milky suspension free of visible particles. The container closure system is comprised of a 5 mL Type 1 glass vial with a 13 mm Fluorotec® stopper and 13 mm aluminum seal. In alternate embodiments, the container closure system is comprised of a 3 mL Type 1 glass vial.

Each vial provides a lyophilized liposomal formulation intended for subcutaneous administration after reconstitution with sodium chloride solution for injection (0.9% w/v).

The above liposomal vaccine formulation was also scaled up to a 9 L scale batch. The batch formula is as follows:

| Component | Amount |
|---|---|
| Glycolipopeptide SEQ ID NO: 2 | 1.3508 g |
| PET Lipid A | 0.6754 g |
| 1,2-Dipalmitoyl-sn-glycero-3-phosphocholine (DPPC) | 39.2008 g |
| 1,2-Dimyristoyl-sn-glycero-3-phosphoglycerol, sodium salt (DMPG-Na) | 4.9089 |
| Cholesterol, NF | 23.3969 |
| tert-Butyl alcohol[#] | 1052.4 g |
| Sterile water for irrigation[#] | 7649.4 g |

Figure 2:
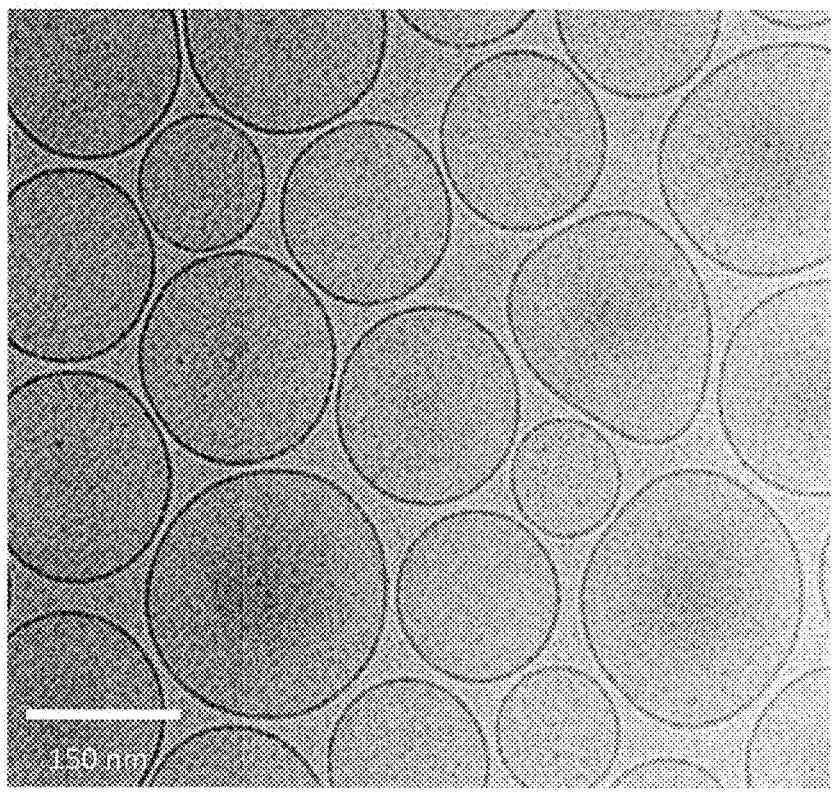
FIG. 2 illustrates images vitrified formulated liposomes by transmission electron microscopy (FIG. 2A) and reconstituted liposomal vaccine by light microscopy (FIG. 2B) and freeze-fracture electron microscopy (FIG. 2C) for a liposomal vaccine formulation described herein.
Figure 2:
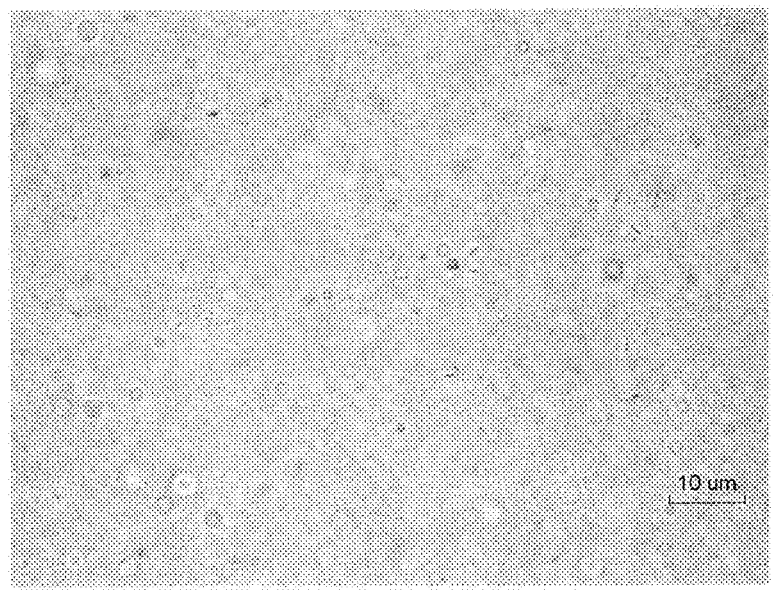
Figure 2:
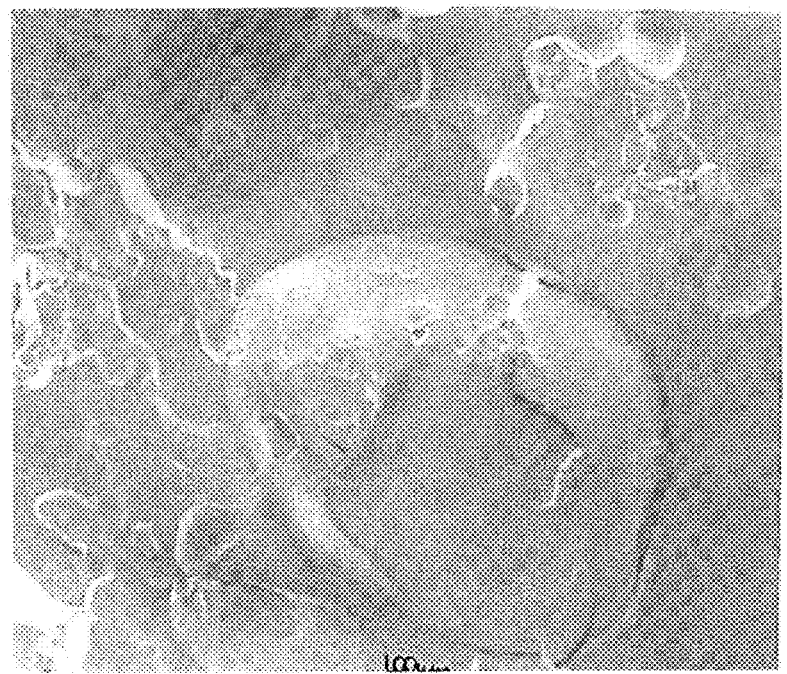

[#]Not in final formulation. Water and alcohol are removed during lyophilization FIG. 2 depicts exemplary images of the liposomal vaccine from the above processes. FIG. 2A shows a transmission electron micrograph of vitrified, formulated liposomes from the batch samples. FIG. 2B depicts an image of the liposomal vaccine reconstituted in saline under light microscopy. FIG. 2C depicts a freeze-fractured image of the reconstituted liposomal vaccine under electron microscopy.

Example 2

Induction of IFNγ in CD4+ and CD8+ T Lymphocytes by a Liposomal Vaccine Formulation of Example 1

C57Bl/6J female mice were injected with a liposomal vaccine formulation of Example 1 in concentrations of 5 μg/mouse, 25 μg/mouse or 100 μg/mouse. Controls included saline treatment and treatment of PET lipid A alone at 50 μg/mouse. After the immunization, splenocytes were isolated from the C57Bl/6 mice and stimulated ex vivo for 48 hours with a MUC1 peptide having SEQ ID NO: 2, a negative control peptide BP-1-109 having the sequence CTRPNNNTRKSIRIQRGPGRAFVTIGKIGNMRQAS*S*L (SEQ ID. NO: 20, S* are lipidated serines), saline vehicle or no treatment.

Figure 3:
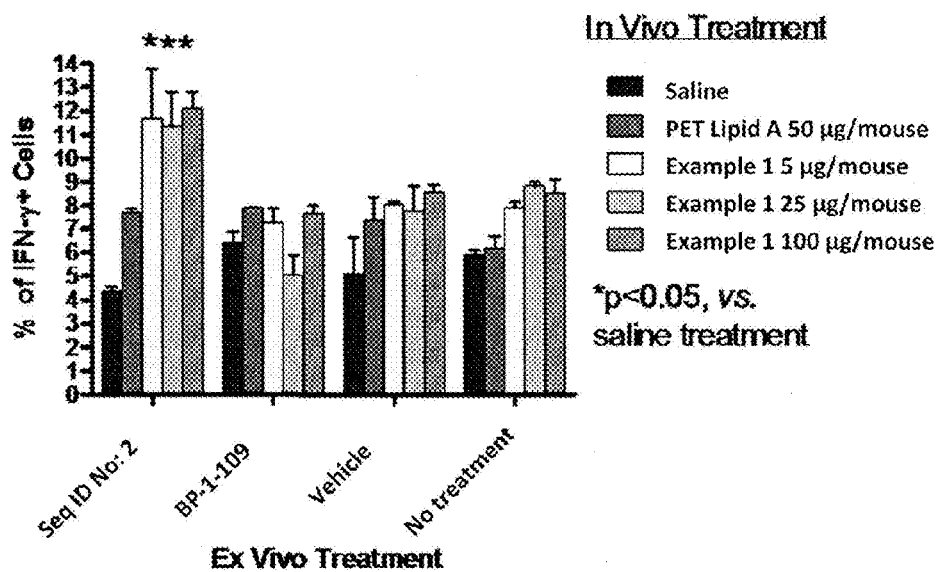
FIG. 3 illustrates ex vivo induction of IFNγ in CD8+ (FIG. 3A) and CD4+ (FIG. 3B) T Lymphocytes in C57BL/6J mice immunized with a vaccine formulation described herein.
Figure 3:
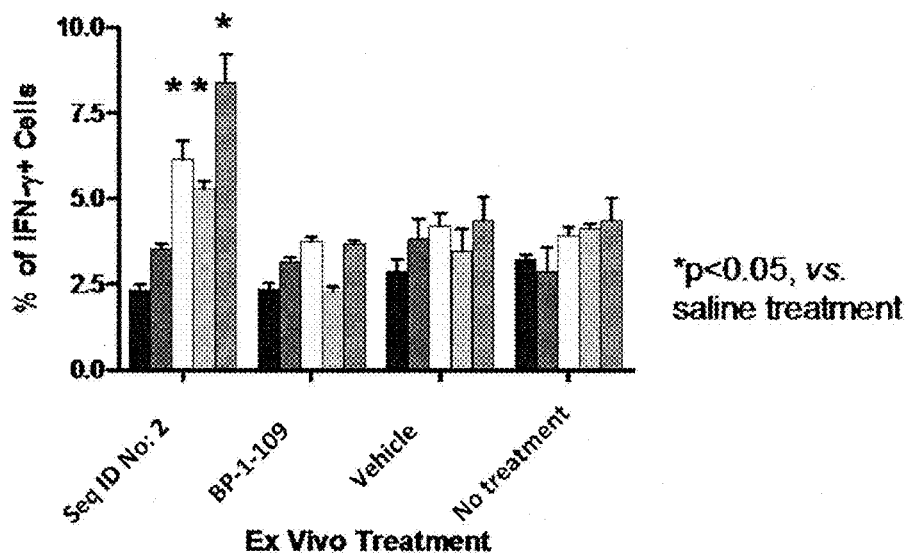

FIG. 3 depicts intracellular IFNγ concentrations in CD4−/CD8+ (FIG. 3A) or CD4+/CD8− (FIG. 3B) T lymphocytes stimulated ex vivo with the various antigens. Data is presented as % positive IFNγ cells relative to total CD4+ or CD8+ cell population. The T cells from mice with in vivo treatment to the various concentrations of a liposomal vaccine formulation of Example 1 had statistically significant (p<0.05) induction of IFNγ when challenged with a MUC1 peptide ex vivo with respect saline treatment.

Example 3

In Vivo Animal Model to Test Humoral Response of the Liposomal Vaccine Formulation of Example 1

Figure 4:
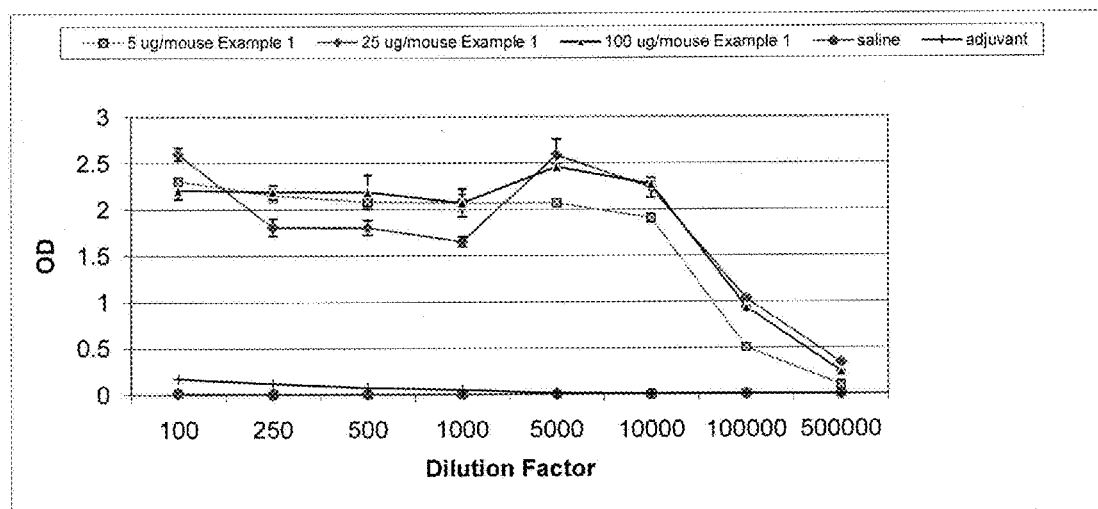
FIG. 4 illustrates a dose response of IgG binding to a MUC1 antigen from mice sera immunized with a vaccine formulation described herein.

C57Bl/6J mice were injected with a liposomal vaccine formulation of Example 1 in three different concentrations of vaccine (5, 25 and 100 μg). 50 μg dose of PET lipid A and saline were used as a negative control. Sera from the mice were isolated and subsequently serially diluted and incubated onto plates coated with MUC1 antigen having SEQ ID NO: 2. After incubation with sera, the plates were washed and a labeled anti-mouse IgG specific antibody was added. The antibody was washed off and the mouse IgG was measured via an ELISA reader. The ELISA analysis in FIG. 4 depicts that antibody levels were similar in all three dose groups, i.e., 5 μg/mouse, 25 μg/mouse, 100 μg/mouse. In contrast, saline and PET lipid A treated animals showed no antibody response.

Figure 5:
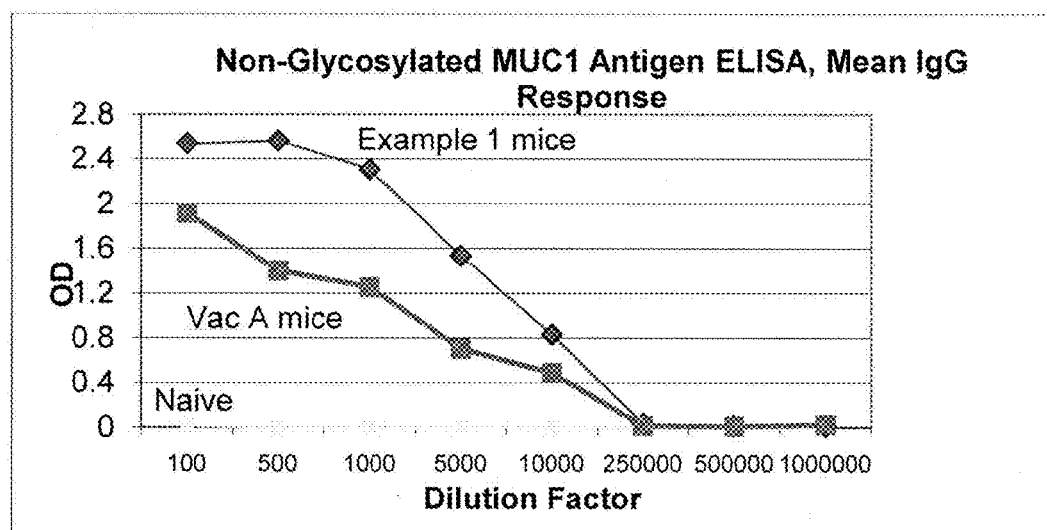
FIG. 5 illustrates a comparison of a liposomal vaccine formulation described herein comprising a SEQ ID NO: 2 versus a vaccine formulation BLP25 (Vaccine A or Vac A) in IgG binding to a glycosylated MUC1 antigen (top) and a non-glycosylated MUC1 antigen (bottom).
Figure 5:
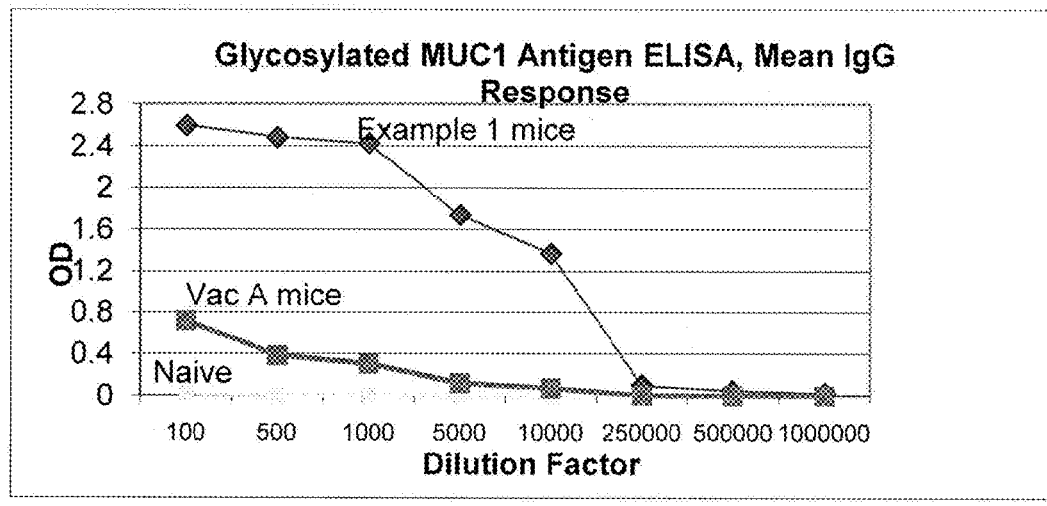

In a similar experiment, mice were injected with a liposomal vaccine formulation of Example 1 or a non-glycosylated MUC1 vaccine (Vaccine A). A naive group was used as a negative control. Sera was isolated, diluted and incubated with either a glycosylated MUC1 peptide having SEQ ID NO: 2 or a non-glycosylated MUC1 peptide, STAPPAHGVT-SAPDTRPAPGSTAPPAKG, SEQ ID NO: 21. FIG. 5 shows a comparison of IgG binding to the glycosylated peptide in either Example 1 liposomal vaccine treated mice or Vaccine A treated mice (top) relative to IgG binding to the non-glycosylated peptide in either Example 1 liposomal vaccine treated mice or Vaccine A treated mice (bottom).

Example 4

IFNγ and Antibody Induction of the Liposomal Vaccine Formulation of Example 1 in Transgenic Human MUC1 Animal Model Transgenic (Tg) mice expressing human MUC1 were derived according to Peat et al., Cancer Res., 52:1954-1960, 1992. The MUC1 Tg mice expressed a human MUC1 transgene in a pattern or level similar to human endogenous MUC1 expression.

In the following experiments, MUC1 Tg mice (N=5/group) were either (1) pre-treated with cyclophosphamide (day −3) and treated with 5, 25, or 100 μg of liposomal vaccine formulation of Example 1 weekly for eight weeks, (2) treated with saline control, or (3) 50 μg PET Lipid A adjuvant alone. At the end of the treatment session, the mice were evaluated for T cell response by IFNγ induction and antibody response by ELISA.

Figure 6:
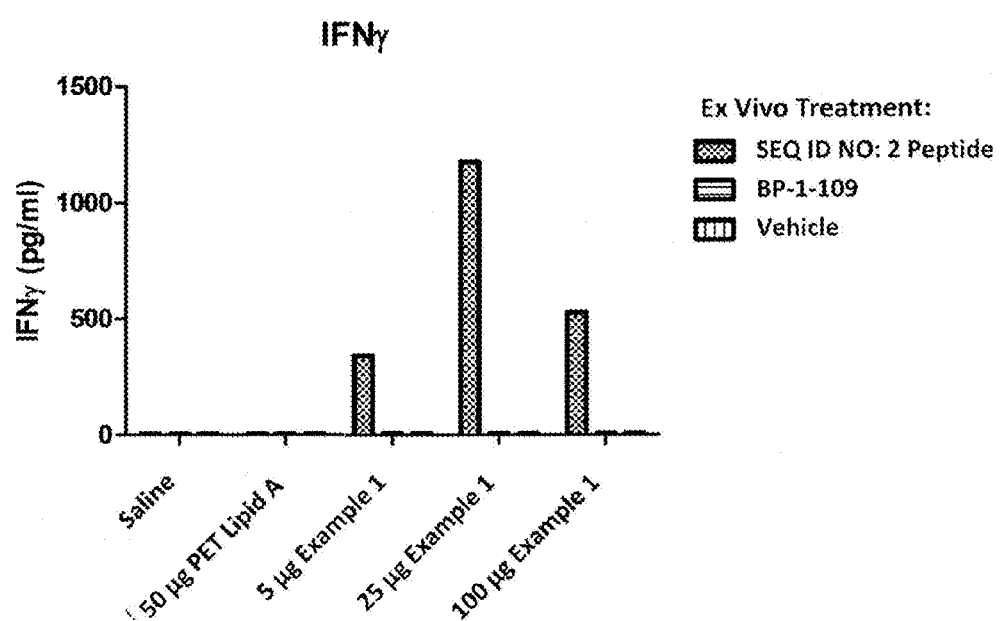
FIG. 6 illustrates ex vivo induction of IFNγ of splenocytes (FIG. 6A) and IgG antibody induction (FIGS. 6B and 6C) in human MUC1 transgenic mice immunized with a vaccine formulation described herein.
Figure 6:
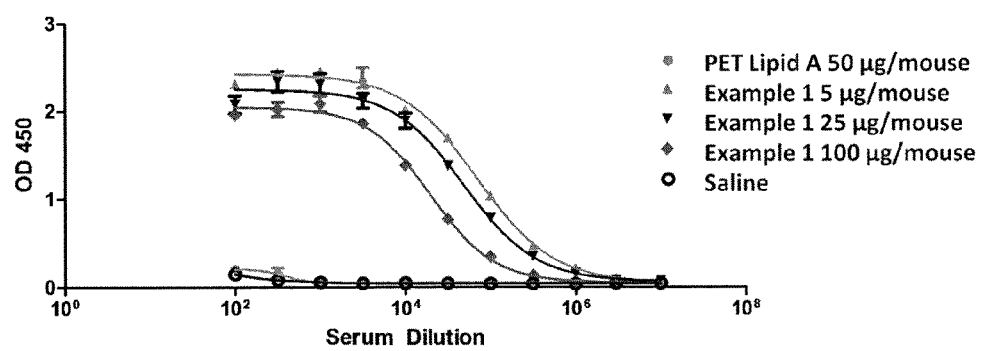
Figure 6:
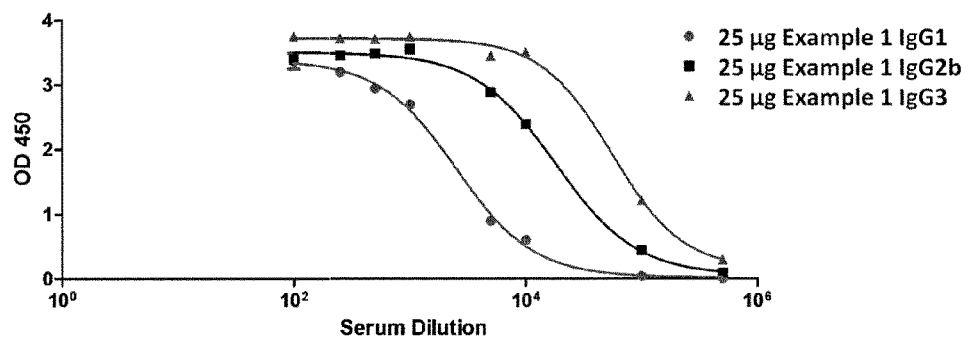

IFNγ Induction:
Pooled splenocytes were isolated from each of the saline treated, PET Lipid A treated, and the liposomal vaccine formulation treated MUC1 Tg mice groups and stimulated ex vivo for 48 hours with a MUC1 peptide having SEQ ID NO: 2, a negative control peptide BP-1-109 having the sequence CTRPNNNTRKSIRIQRGPGRAFVTIGKIGNMRQAS*S*L (SEQ ID. NO: 20, S* are lipidated serines) or vehicle. IFNγ expression or induction after the ex vivo treatment was measured in the cell culture supernatants using Luminex technology (FIG. 6A). The transgenic animals immunized with the liposomal vaccine formulation of Example 1 in all three concentrations showed IFNγ response with respect to ex vivo stimulation with the MUC1 peptide having SEQ ID NO: 2.

Antibody Induction:
Sera was collected from the above treated animals and subjected to ELISA analysis with a MUC1 peptide having SEQ ID NO: 2 similar to the previous examples. FIG. 6B shows total IgG levels from mice vaccinated with 5, 25 or 100 μg of the liposomal vaccine formulation of Example 1 or treated with 50 μg of liposomal PET Lipid A or saline. FIG. 6C shows the IgG isotypes from the mice vaccinated with 25 μg of the liposomal vaccine formulation of Example 1. Plotted data in FIGS. 6B and 6C represent the mean serum IgG levels from 5 individual mice.

Example 5

Liposomal Vaccine Formulation of Example 1 and Antibody Specificity for Human Tumor MUC1

Figure 7:
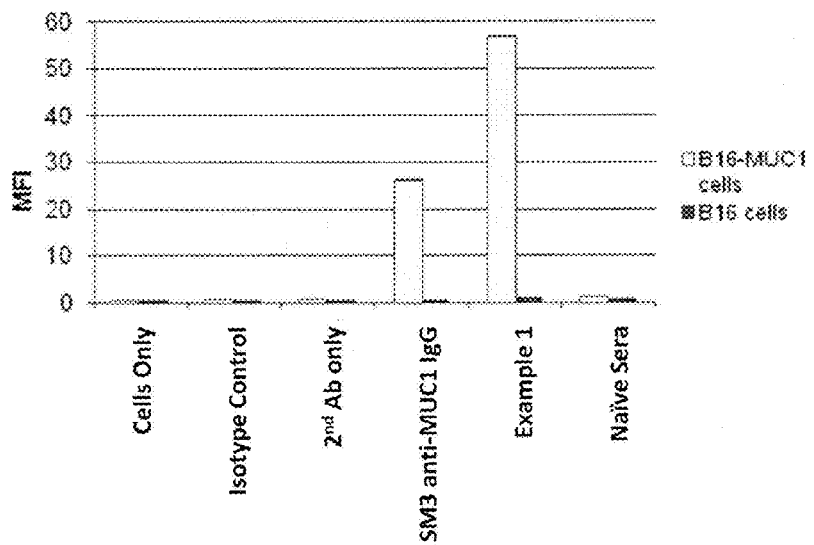
FIG. 7 illustrates FACS analysis of B16-MUC1 and B16 cells (FIG. 7A) or Breast epithelial and Breast carcinoma cells (FIG. 7B) with sera from mice vaccinated with a vaccine formulation described herein.
Figure 7:
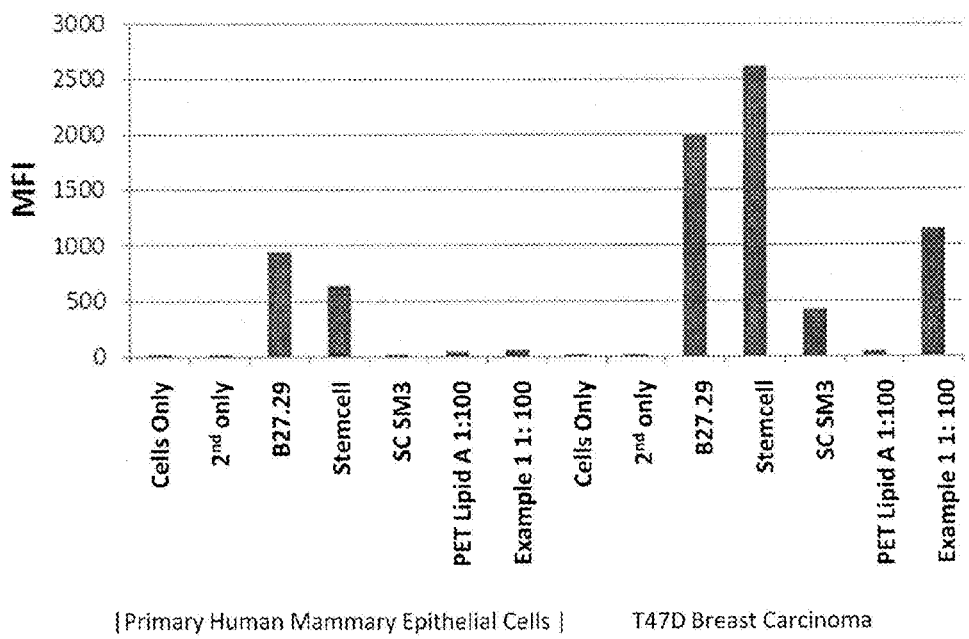

C57Bl/6J mice were vaccinated with 100 μg of liposomal vaccine formulation of Example 1. Sera from the treated mice or naive animals were used for FACS analysis of either 1316 or 1316-MUC1 mouse melanoma cell lines. An anti-MUC1 antibody SM3 (SCBT SC-53381) was used as a positive control for hypoglycosylated MUC1. FIG. 7A shows that IgG from mice immunized with the liposomal vaccine formulation of Example 1 selectively binds to cellular MUC1.

In a similar experiment, human breast epithelial cells and T47D breast carcinoma cells were stained using serum from human MUC1 transgenic mice vaccinated with either 100 μg of liposomal vaccine formulation of Example 1 or 50 μg of PET lipid A. Cell staining was detected by flow cytometry using a fluorescent conjugated anti-mouse secondary antibody. FIG. 7B shows that IgG from mice immunized with the liposomal vaccine formulation of Example 1 discriminate between normal and tumor MUC1. SM3 was again used as a positive control for hypoglycosylated MUC1 and MUC1 monoclonal antibodies B27.29 and Stemcell (Stem Cell Technologies) were used as positive controls for fully glycosylated normal MUC1.

Example 6

The Effect of a Liposomal Vaccine Formulation of Example 1 on Tumor Growth

C57Bl/6 mice were treated using a bi-weekly schedule with saline vehicle, 50 μg Liposomal PET Lipid A or 5 μg of liposomal vaccine formulation of Example 1 starting on day −42. On Day 0, mice were challenged with either $2 \times 10^6$ B16-MUC1, $0.5 \times 10^6$ B16, or $2 \times 10^6$ MC38-MUC1 tumor cells followed by two additional vaccinations on days +3 and +17. Tumor growth was recorded twice weekly.

In the B16-MUC1 model, animals treated with the Example 1 vaccine formulation had no tumors at Day 44. 9/12 animals were tumor free in the Example 1 vaccine formulation group at end of study. In contrast, the saline and PET lipid A groups exhibited similar tumor growth curves. Mean tumor volume in these two groups was about 200 mm$^3$ by Day 10. By Day 24, mean tumor volume was about 1200 mm$^3$ for the saline and PET lipid A groups.

In the MC38-MUC1 model, 3/12 animals were tumor free in the Example 1 vaccine formulation group at the end of the study. Tumor growth was also decreased as compared to the saline and PET lipid A groups. By Day 32, mean tumor volume was about 120 mm$^3$ for the Example 1 vaccine formulation group as compared to about 1200 mm$^3$ for the PET lipid A group and about 1700 mm$^3$ for the saline group.

In the B16 model where the tumors do not exhibit MUC1, tumor growth was similar among all three groups.

Example 7

Clinical Trial to Test Effect of Liposomal Vaccine Formulation for Immunotherapy of Non-small Cell Lung Cancer This is a prospective open label, controlled, randomized study to test the safety and efficacy of active specific immunotherapy a liposomal vaccine of Example 1 for the treatment of patients with stage IIIB or stage IV non-small cell lung cancer (NSCLC). To be eligible, patients entering the trial will have demonstrated either stable disease or a clinical response after first-line treatment (chemotherapy alone, or chemotherapy and radiotherapy) and have an ECOG performance status of 0, 1 or 2. Following a 3 week washout period, patients will be stratified by disease status (either stage IIIB locoregional disease or stage IIIB with malignant pleural effusion and stage IV), and randomized to either best supportive care (BSC) plus vaccine immunotherapy, or BSC alone.

Eight weekly subcutaneous vaccinations with 1,000 µg of Liposome vaccine of Example 1 will be administered at weeks 0, 1, 2, 3, 4, 5, 6 and 7.

Primary outcome measures will be documentation of safety profile of the liposome vaccine of Example 1, and comparison of survival rate of patients in the two arms of the trial. Secondary outcome measures will be to measure immune response elicited by the liposome vaccine of Example 1, and to evaluate quality of life for patients undergoing immunotherapy.

Example 8

Clinical Trial to Test Maximum Tolerated Dose and/or Recommended Dosage of Liposomal Vaccine Formulation in Patients with Advanced Solid Tumors This is an open label, Phase I dose escalation study to evaluate the safety and immunogenicity of repeat dose vaccination with the liposome vaccine of Example 1 in patients with previously treated Stage 3 or 4 solid tumors, with histologies that have been associated with expression of the MUC1 antigen including but not limited to: breast, non-small cell lung, ovarian, colorectal, gastric, prostate, pancreatic, and renal cell cancers.

Part 1 evaluates escalating dose levels of the liposome vaccine of Example 1 administered subcutaneously once every other week (Q2W) over 8 weeks (for a total of 4 doses) or once every week (QW) over 8 weeks (for a total of 8 doses), and uses a 3+3 dose escalation design to identify the maximum tolerated dose (MTD) and/or recommended dose (RD) for each dosing schedule, for further evaluation in Part 2 of the study. Part 2 evaluates the safety, immunogenicity, and potential anti-tumor activity of the liposome vaccine of Example 1 administered over 8 weeks at the Q2W and QW MTD/RD in cohorts of 15 patients each. After the 8 week administration period, patients are evaluated for safety, immune response and tumor response to Week 20.

The study population includes patients with previously treated Stage 3 or 4 solid tumors with histologies that are associated with expression of MUC1.

Inclusion Criteria:

18-70 years of age at time of consent

Life expectancy of at least 6 months, according to investigator's opinion

Have histologically confirmed breast, non-small cell lung, ovarian, colorectal, gastric, prostate, pancreatic, or renal cell cancer, or other tumor type Have evidence of persistent, recurrent, or progressive disease after at least one course of systemic therapy for locally advanced or metastatic disease, including chemotherapy, targeted therapy, or immunotherapy Clinical stage 3 or 4 disease ECOG 0 or 1

Adequate hematological, renal and hepatic function parameters

Exclusion Criteria:

Has received treatment with any systemic chemotherapy, radiation, or experimental agent within 4 weeks of study drug dosing Has a known history of autoimmune disease, arteritis, or vasculitis or recognized immunodeficiency disease (e.g., cellular immunodeficiencies, hypogammaglobulinemia, or dysgammaglobulinemia)

Has any preexisting medical condition requiring chronic steroid or immunosuppressive therapy HIV, hepatitis B or hepatitis C positive Receipt of any other vaccine $\leqq 4$ weeks prior to study enrollment Mode of Administration:

All subjects receive an initial intravenous injection of cyclophosphamide 250 mg/m$^2$ on Day −3. The liposome vaccine of Example 1 is administered subcutaneously, starting on Day 1 per cohort assignment. All patients receive doses of the liposome vaccine of Example 1 administered as four separate injections at four separate injection sites (one injection each in the right upper arm or thigh, left upper arm or thigh, and right and left lower abdomen). The starting dose is 250 µg of the liposomal vaccine with 125 µg PET. Lipid A adjuvant (2:1 ratio). Additional dose levels include 500 and 1000 µg of the liposomal vaccine in a 2:1 ratio with the adjuvant. The dose levels are selected using a dose-doubling design. An intermediate dose level, 750 µg, is considered when the MTD is less than 1000 µg.

In the Part 2 evaluation and assessment of the eight week administration, immune response measures include serum titers of MUC-1 specific antibodies using ELISA specific to the liposomal vaccine of Example 1 and MUC-1 specific ELIPSOT assays for IFN-gamma. Immune response measures also include but not be limited to: proportion of circulating CD4 and CD8 T cells, proportion of circulating myeloid suppressor cell population, levels of T cell cytokines, relative proportion of IgG and IgM antibodies directed against the liposomal vaccine of Example 1, and levels of circulating cytokines. Tumor response is assessed as defined by RECIST 1.1.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A liposomal vaccine formulation comprising:

(a) a glycolipopeptide of structure:

SEQ ID NO: 2
H₂N-TSAPDT(Tn)RPAPGS(Tn)T(Tn)APPAHGVTSAPDT(Tn)R
PAPGS(Tn)T(Tn)APPAHGVS*S*L-OH wherein Tn represents, independently at each occurrence, α-N-Acetylgalactosamine (GalNAcα1) covalently attached to a Serine or Threonine residue; and

*represents, independently at each occurrence, a C14 lipid covalently attached to a Serine residue;

(b) an adjuvant of structure:

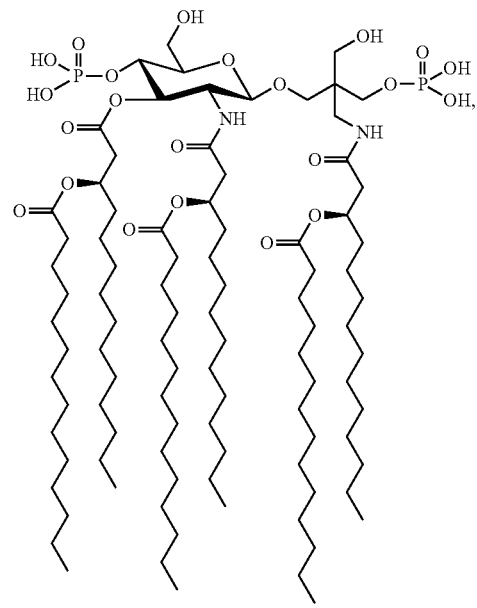

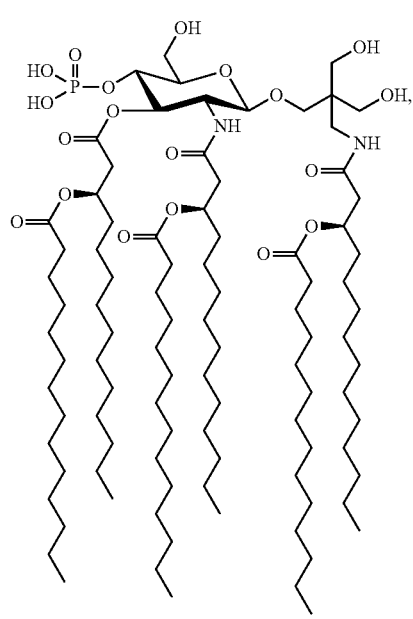

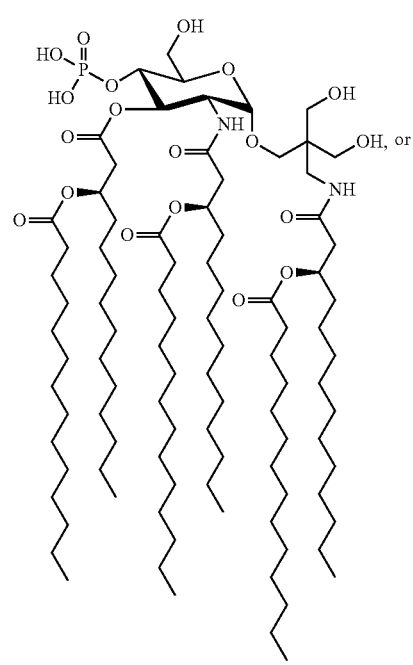

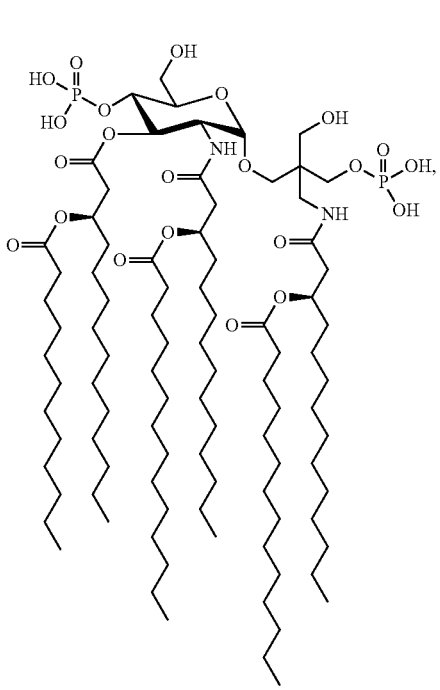

or a pharmaceutically acceptable salt thereof; and (c) a carrier lipid.

2. The formulation of claim 1, wherein the C14 lipid is a myristoyl chain.

3. The formulation of claim 1, wherein the adjuvant is

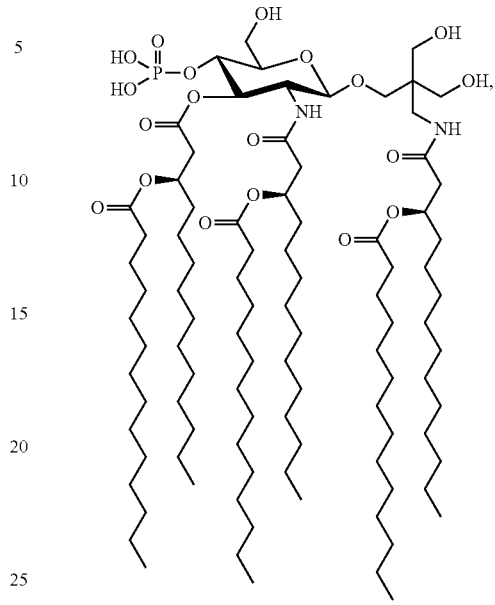

or pharmaceutically acceptable salt thereof.

4. The formulation of claim 3, wherein the adjuvant is a pharmaceutically acceptable triethylamine salt.

5. The formulation of claim 1, wherein the carrier lipid is selected from DMPG, DPPC or a pharmaceutically acceptable salt thereof, or combination thereof.

6. The formulation of claim 1, further comprising cholesterol.

7. The formulation of claim 1, wherein the formulation is lyophilized.

8. The formulation of claim 1, wherein the formulation is lyophilized and is further reconstituted.

* * * * *